United States Patent
Shimamoto et al.

(10) Patent No.: US 6,297,248 B1
(45) Date of Patent: Oct. 2, 2001

(54) 1-ARYL-1,8-NAPHTHYLIDIN-4-ONE DERIVATIVE AS TYPE IV PHOSPHODIESTERASE INHIBITOR

(75) Inventors: Tetsuo Shimamoto, Suita; Hidekazu Inoue, Takatsuki; Yasuhiro Hayashi, Osaka, all of (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 09/284,019

(22) PCT Filed: Aug. 6, 1998

(86) PCT No.: PCT/JP98/03510

§ 371 Date: Apr. 6, 1999

§ 102(e) Date: Apr. 6, 1999

(87) PCT Pub. No.: WO99/07704

PCT Pub. Date: Feb. 18, 1999

(30) Foreign Application Priority Data

Apr. 6, 1997 (JP) ................................. 9-212322

(51) Int. Cl.[7] ............... A61K 31/4375; A61K 31/497; A61K 31/506; C07D 471/04; C07D 239/32; C07D 241/20

(52) U.S. Cl. ................ 514/255.5; 514/256; 514/275; 514/300; 544/331; 544/405; 546/123

(58) Field of Search ................... 514/300, 275, 514/254, 255.05, 256; 546/123; 544/331, 405

(56) References Cited

U.S. PATENT DOCUMENTS

| | | | |
|---|---|---|---|
| 4,284,629 | * 8/1981 | Grohe | 424/246 |
| 5,631,256 | * 5/1997 | Demuth, Jr. | 514/252 |
| 5,753,666 | * 5/1998 | Beasley | 514/258 |
| 5,817,670 | * 10/1998 | Takayama | 514/300 |
| 5,910,498 | * 6/1999 | Yazaki | 514/255 |
| 5,998,436 | * 12/1999 | Yazaki | 514/312 |

FOREIGN PATENT DOCUMENTS

| | | |
|---|---|---|
| 0 779 292 A1 | * 6/1997 | (EP) . |
| 55164682 | * 12/1980 | (JP) . |
| WO 94/12499 | * 6/1994 | (WO) . |
| 95/28405 | 8/1995 | (WO) . |
| 96-12704 | * 5/1996 | (WO) . |
| 97-11068 | * 3/1997 | (WO) . |
| WO 97/04775 | * 3/1997 | (WO) . |

OTHER PUBLICATIONS

Masaru Tai et al., The Japanese Journal of Antibiotics, 42(4), pp. 868–875, Apr. 1989.

Hirokazu Narita et al., "Pyridonecarboxylic Acids as Antibacterial Agents. V[1a] Synthesis and Structure–Activity Relationship of 7–Amino–6–fluoro–1–(fluorophenyl)–4–oxo–1, 8–naphthyridine–3–carboxylic Acids", Yakugaku Zasshi, vol. 106 (9), pp. 802–807, 1986.

Stanislav Radl et al., "Syntéza a Antibakteriální Aktivita Některých 1–Aryl–1,4–Dihydro–4–Oxo–1, 8–Naftyridin–3–Karboxylových Kyselin", Ceskoslovenska Farmacie, 39(4), pp. 177–180, 1990.

Stanislav Radl et al., "Recent Advances in the Synthesis of Antibacterial Quinolones", Heterocycles, vol. 34, No. 11, pp. 2143–2177, 1992.

Matsuura et al, *Biol. Pharm. Bull.*, "Substituted 1,8–Naphthyridin–2(1H)–Ones as Selective Phosphodiesterase IV Inhibitors," vol. 17(4), pp. 498–503 (1994).*

* cited by examiner

*Primary Examiner*—Evelyn Mei Huang
(74) *Attorney, Agent, or Firm*—Burns, Doane, Swecker & Mathis, L.L.P.

(57) ABSTRACT

A 1-aryl-1,8-naphthylidin-4-one derivative having the formula (I):

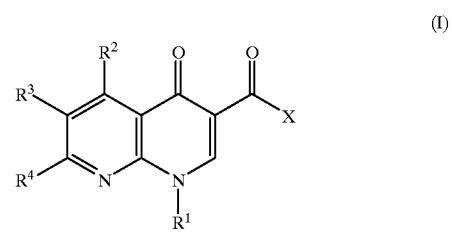

wherein $R^1$ indicates a substituted or unsubstituted aryl group or a substituted or unsubstituted heteroaryl group, $R^2$, $R^3$, and $R^4$ independently indicate a hydrogen atom, a substituted or unsubstituted lower alkyl group, or a halogen atom, X indicates a group $NR^5R^6$ or a group $OR^7$, wherein $R^5$ and $R^6$ independently indicate a hydrogen a atom, a substituted or unsubstituted lower alkyl group, a substituted or unsubstituted cycloalkyl group, a substituted or unsubstituted aryl group, or a substituted or unsubstituted heteroaryl group, and $R^7$ indicates a hydrogen atom, a substituted or unsubstituted lower alkyl group, or a substituted or unsubstituted cycloalkyl group or a salt or solvate thereof and a type IV phosphodiesterase inhibitor containing the same as an effective component.

34 Claims, No Drawings

1-ARYL-1,8-NAPHTHYLIDIN-4-ONE DERIVATIVE AS TYPE IV PHOSPHODIESTERASE INHIBITOR

This application is the national phase of PCT/JP98/03510, filed on Aug. 6, 1998.

TECHNICAL FIELD

The present invention relates to a 1-aryl-1,8-naphthylidin-4-one derivative as a selective type IV phosphodiesterase (i.e., "PDE") inhibitor and a salt, and solvate thereof and a pharmaceutical composition and a type IV phosphodiesterase inhibitor containing the same as an effective component as well as an agent of preventing or treating for cytokine related diseases.

BACKGROUND ART

The intracellular second messenger cAMP or cGMP is broken down and deactivated by phosphodiesterase (PDE), which is classified into at least types I to VII. PDE is widely distributed in the tissue and organs of the body. Among these, type IV phosphodiesterase selectively breaks down cAMP and is found in the central tissue and in the heart, lungs, kidneys, and other organs and in the various hemocyte components etc. Further, it is known to be involved in the derivation of IL-1 and IL-6, TNF-α, and other various cytokines.

Catechol type derivatives such as rolipram, known to be a selective inhibitor of this enzyme, quinazoline type derivatives such as nitraquazone, xanthine type derivatives such as theophylline and denbufylline, etc. are being used or developed as antidepressants, antiasthmatics, antiinflamatorics, etc. No drug has however yet been developed which solves the problems such as the selectivity with other isoenzymes and various side effects. There is no satisfactory medicine which has this enzyme inhibiting action as the main mechanism for achieving the medicinal effect.

On the other hand, as a compound having a PDE IV inhibiting action and a naphthylidinone skeleton, for example, as a compound having a carbonyl group at the 2-position in the 1,8-naphthylidine skeleton, there are known those described in JP-A-55-164682, WO-A-94-12499, WO-A-96-06843, etc.

Further, as a compound having a PDE IV inhibiting action and carbonyl group at the 4-position in a 1,8-naphthylidine skeleton, WO-A-97-04775 describes one where the 1-position substituent group is an ethyl group. Further, as the method of synthesis described in this publication, the method shown in the following formula was used, based on the method of Kaminsky et al. (J. Med. Chem. 1968, 11, 160). However, the 1-position substituent group disclosed in this method is only an alkyl group.

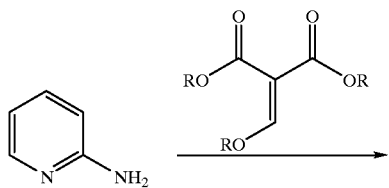

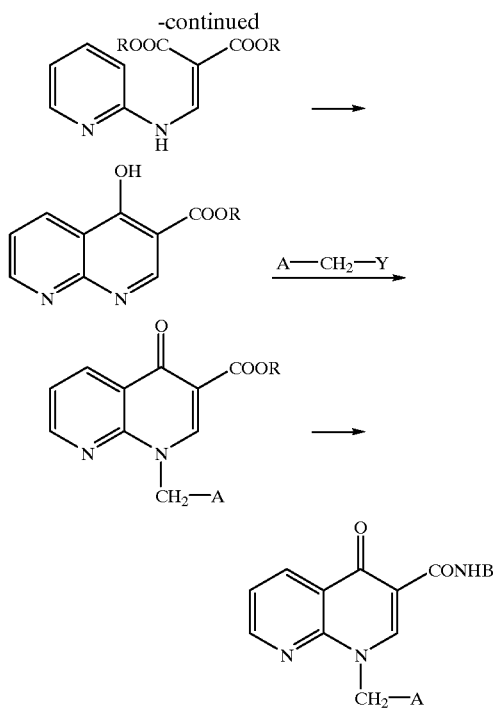

In the above reaction process, it is only possible to use a substitution reaction using a highly reactive alkyl halide (A—CH₂—Y), and therefore, the substituent groups which can be introduced to the 1-position are limited.

DISCLOSURE OF INVENTION

The objects of the present invention are to provide a compound or a salt or solvate thereof, useful as a medicine for the prevention or treatment of bronchial asthma, chronic bronchitis, and other respiratory diseases, diseases relating to abnormality of nervous system such as impaired learning, memory, and recognition relating to Alzheimer's disease, Parkinson's disease, and the like, diseases relating to mental abnormality such as maniac depression and schizophrenia, atopic dermitis, conjunctivitis, acquired immunity disorder syndrome and other inflammatory diseases, osteoarthritis, rheumatoid arthritis, and other general or local joint diseases, rheumatoid arthritis, sepsis, Crohn disease and other diseases which are related to various cytokines such as tumor necrosis factor (TNF-α), and the like by selectively inhibiting the type IV phosphodiesterase and further inhibiting the production of TNF-α.

In accordance with the present invention, there is provided a 1-aryl-1,8-naphthylidin-4-one derivative having the formula (I):

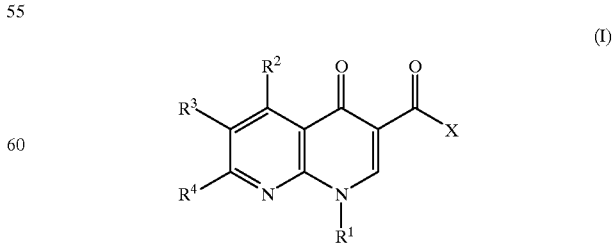

(I)

wherein $R^1$ indicates a substituted or unsubstituted aryl group or a substituted or unsubstituted heteroaryl group, $R^2$, $R^{3l}$ and $R^4$ independently indicate a hydrogen atom, a substituted or unsubstituted lower alkyl group, or a halogen atom, X indicates the group $NR^5R^6$ or group $OR^7$, wherein $R^5$ and $R^6$ independently indicate a hydrogen atom, a substituted or unsubstituted lower alkyl group, a substituted or unsubstituted cycloalkyl group, a substituted or unsubstituted aryl group, or a substituted or unsubstituted heteroaryl group, and $R^7$ indicates a hydrogen atom, a substituted or unsubstituted lower alkyl group, or a substituted or unsubstituted cycloalkyl group or a salt or solvate thereof.

In accordance with the present invention, there is also provided a 1-aryl-1,8-naphthylidin-4-one derivative having the formula (I'):

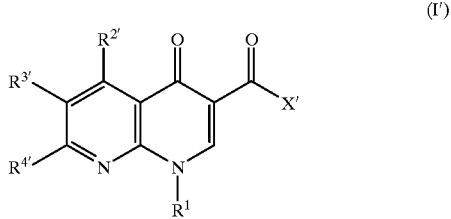

(I')

wherein $R^1$ indicates a substituted or unsubstituted aryl group or a substituted or unsubstituted heteroaryl group, $R^{2'}$, $R^{3'}$, and $R^{4'}$ independently indicate a hydrogen atom, or a substituted or unsubstituted lower alkyl group, X' indicates the group $NR^5R^6$, $R^5$ and $R^6$ independently indicate a hydrogen atom, a substituted or unsubstituted lower alkyl group, a substituted or unsubstituted cycloalkyl group, a substituted or unsubstituted aryl group, or a substituted or unsubstituted heteroaryl group or a salt or solvate thereof.

In accordance with the present invention, there is also provided a pharmaceutical composition and a type IV phosphodiesterase inhibitor as well as an agent of preventing or treating for cytokine related diseases, containing a 1-aryl-1,8-naphthylidin-4-one derivative as set forth in the above formula (I) or (I') or its pharmaceutically acceptable salt or solvate as the effective ingredient.

Further, according to the present invention, it is possible to provide a synthesis intermediate useful for the production of a 1-aryl-1,8-naphthylidin-4-one derivative as set forth in the above general formula (I) or (I').

BEST MODE FOR CARRYING OUT THE INVENTION

The inventors engaged in intensive research to develop a compound having a superior type IV phosphodiesterase inhibiting action and a process for producing the same and, as a result, found that a compound having the formula (I) or (I') with a carbonyl group at the 4-position in the 1,8-naphthylidine skeleton and an aryl group or heteroaryl group as the 1-position substituent group has a superior type IV phosphodiesterase inhibiting action, whereby the present invention was completed.

The preferable examples of the aryl group of the substituted or unsubstituted aryl group indicated by $R^1$ in the formula (I) and (I') according to the present invention are $C_6$ to $C_{14}$ aryl group, for example, a phenyl group, naphthyl group, indenyl group, anthryl group, etc. More preferable example is a phenyl group. Preferable examples of the substituents for the aryl group are a hydroxyl group, a lower alkyl group, a halogen atom such as a fluorine, chlorine, bromine or iodine atom, an oxygen atom, a sulfur atom, an alkoxy group, a cyano group, a nitro group, an amino group, an alkylamino group, an amide group, an acyl group, an acyloxy group, a carboxyl group, a lower alkoxycarbonyl group, an aralkyloxycarbonyl group, a carbamoyl group, a thiol group, an alkylthio group, a sulfonyl group, etc.

In the specification, "lower", unless otherwise alluded to, means 1 to 8 carbon atoms, preferably 1 to 6 carbon atoms.

Preferable examples of the heteroaryl group of the substituted or unsubstituted heteroaryl group indicated by $R^1$ in the formula (I) or (I') of the present invention are a monocyclic or polycyclic heteroaryl group having a 5- to 7-member ring including 2 to 8 carbon atoms and 1 to 4 hetero atoms of an oxygen atom, a nitrogen atom, or a sulfur atom, for example, a pyrrole group, a furyl group, a thienyl group, an imidazolyl group, a thiazolyl group, a pyridyl group, a pyrazinyl group, an indolyl group, a quinolyl group, an isoquinolyl group, etc. may be mentioned. The more preferable example is a pyridyl group. Examples of the preferable substituent groups of the heteroaryl group are a hydroxyl group, a lower alkyl group, a halogen atom such as a fluorine, chlorine, bromine or iodine atom, an oxygen atom, a sulfur atom, an alkoxy group, a cyano group, a nitro group, an amino group, an alkylamino group, an amide group, an acyl group, an acyloxy group, a carboxyl group, a lower alkoxycarbonyl group, an aralkyloxycarbonyl group, a carbamoyl group, a thiol group, an alkylthio group, a sulfonyl group, etc.

The preferable examples of the lower alkyl group indicated by $R^2$, $R^3$, or $R^4$ in the formula (I) or $R^{2'}$, $R^{3'}$ or $R^{4'}$ in the formula (I') are $C_1$–$C_6$ linear or branched alkyl group such as a methyl group, ethyl group, n-propyl group, iso-propyl group, isobutyl group, t-butyl group, etc. The preferable examples of the halogen atom indicated by $R^2$, $R^3$, or $R^4$, in the formula (I), fluorine, chlorine, bromine, and iodine. The preferable examples of a combination of $R^2$, $R^3$, and $R^4$, or a combination of $R^{2'}$, $R^{3'}$ and $R^{4'}$, are all hydrogen atoms.

The preferable examples of the alkyl group of the substituted or unsubstituted lower alkyl group indicated by $R^5$ or $R^6$ in formula (I) or (I') are $C_1$ to $C_6$ linear or branched alkyl group such as a methyl group, ethyl group, n-propyl group, isopropyl group, isobutyl group, t-butyl group, etc. The preferable examples of the substituent group of the lower alkyl group are preferably $C_3$ to $C_6$ cycloalkyl group such as a cyclopropyl group, a cyclobutyl group, a cyclopentyl group and a cyclohexyl group, $C_6$ to $C_{14}$ aryl group such as a phenyl group, lower alkenyl group such as a vinyl group, etc., a halogen atom such as a fluorine, chlorine, bromine or iodine atom, a hydroxyl group, an alkoxy group, a cyano group, a nitro group, an amino group, an alkylamino group, an amide group, an acyl group, an acyloxy group, a carboxyl group, a lower alkoxycarbonyl group, an aralkyloxycarbonyl group, a carbamoyl group, a thiol group, an alkylthio group, a sulfonyl group, etc.

The preferable examples of the cycloalkyl group of the substituted or unsubstituted cycloalkyl group indicated by $R^5$ or $R^6$ in formula (I) or (I') are $C_3$–$C_6$ cycloalkyl group such as a cyclopropyl group, a cyclobutyl group, a cyclopentyl group, a cyclohexyl group, etc. The preferable examples of the substituent group for the cycloalkyl group are a $C_6$ to $C_{14}$ aryl group such as a phenyl group, lower alkenyl group such as a vinyl group, etc. a hydroxyl group, a halogen atom such as a fluorine, chlorine, bromine or iodine atom, an alkoxy group, a cyano group, a nitro group, an amino group, an alkylamino group, an amide group, an acyl group, an acyloxy group, a carboxyl group, a lower alkoxycarbonyl group, an aralkyloxycarbonyl group, a carbamoyl group, a thiol group, an alkylthio group, a sulfonyl group, etc.

The preferable examples of the aryl group of the substituted or unsubstituted aryl group indicated by $R^5$ or $R^6$ in formula (I) or (I') are a $C_6$ to $C_{14}$ aryl group such as a phenyl group, a naphthyl group, an indenyl group, an anthryl group, etc. The more preferable example is a phenyl group. Further, preferable examples of the substituent group for the aryl group are $C_1$–$C_6$ linear or branched alkyl group such as a methyl group, an ethyl group, a n-propyl group, an isopropyl group, an isobutyl group and a t-butyl group, a $C_6$–$C_{14}$ aryl group such as a phenyl group and a naphthyl group, a halogen atom such as fluorine, chlorine, bromine or iodine atom, a hydroxy group, an alkoxy group, a cyano group, a nitro group, an amino group, an alkylamino group, an amido group, an acyl group, an acyloxy group, a carboxyl group, a lower alkoxycarbonyl group, an aralkyloxycarbonyl group, a carbamoyl group, a thiol group, an alkylthio group, a sulfonyl group, etc.

Further, preferable examples of the heteroaryl group of the substituted or unsubstituted heteroaryl group indicated by $R^5$ or $R^6$ in formula (I) or (I') are a monocyclic or polycyclic heteroaryl group having a 5- to 7-member ring including 1 to 4 hetero atoms including an oxygen atom, a nitrogen atom, or a sulfur atom such as a pyrrole group, a furyl group, a thienyl group, an imidazolyl group, a thiazolyl group, a pyridyl group, a pyrazinyl group, an indolyl group, a quinolyl group, an isoquinolyl group, a benzimidazolyl group, a benzthiazolyl group, etc. More preferable examples are a 4-pyridyl group, a 3-pyridyl group, a 2-pyridyl group, a thiazolyl group, etc. The examples of preferable substituent groups for the heteroaryl group are a $C_1$–$C_6$ linear of branched alkyl group such as a methyl group, an ethyl group, a n-propyl group, an isopropyl group, an isobutyl group, a t-butyl group, a $C_6$–$C_{14}$ aryl group such as a phenyl group, a naphthyl group, a halogen atom such as fluorine, chlorine, bromine or iodine atom, a hydroxy group, an alkoxy group, a cyano group, a nitro group, an amino group, an alkylamino group, an amide group, an acyl group, an acyloxy group, a carboxyl group, a lower alkoxycarbonyl group, an aralkyloxycarbonyl group, a carbamoyl group, a thiol group, an alkylthio group, a sulfonyl group, etc. The preferable examples of the substituted or unsubstituted heteroaryl group indicated by $R^5$ or $R^6$ are a 4-pyridyl group, a 3-pyridyl group, a 3,5-dichloropyridin-4-yl group, etc.

The preferable examples of the lower alkyl group of the substituted or unsubstituted lower alkyl group indicated by $R^7$ in formula (I) are a $C_1$–$C_6$ linear or branched alkyl group such as a methyl group, an ethyl group, a n-propyl group, an isopropyl group, an isobutyl group, a t-butyl group, etc. The preferable examples of the substituent group of the lower alkyl group are a $C_6$–$C_{14}$ aryl group such as a phenyl group, a halogen atom such as fluorine, chlorine, bromine or iodine atom, a lower alkenyl group such as a vinyl group, etc. a cyano group, a nitro group, an amino group, an amide group, an acyl group, an acyloxy group, a carboxyl group, a lower alkoxycarbonyl group, an aralkyloxycarbonyl group.

The preferable examples of the cycloalkyl group for the substituted or unsubstituted cycloalkyl group indicated by $R^7$ in formula (I) are a $C_3$–$C_6$ cycloalkyl group such as a cyclopropyl group, a cyclobutyl group, a cyclopentyl group, a cyclohexyl group, etc. The preferable examples of the substituent group for the cycloalkyl group are a $C_6$–$C_{14}$ aryl group such as a phenyl group, etc. a lower alkenyl group such as a vinyl group, etc. a halogen atom such as a fluorine, chlorine, bromine or iodine atom, a hydroxy group, an alkoxy group, a cyano group, a nitro group, an amino group, an alkylamino group, an amide group, an acyl group, an acyloxy group, a carboxyl group, a lower alkoxycarbonyl group, an aralkyloxycarbonyl group, a carbamoyl group, a thiol group, an alkylthio group, a sulfonyl group, etc.

The specific examples of the 1-aryl-1,8-naphthylidin-4-one derivative described in the above formula (I) or (I') of the present invention are as follows.

(a) a 1-aryl-1,8-naphthylidin-4-one derivative where all of $R^2$, $R^3$, and $R^4$ or $R^{2'}$, $R^{3'}$ and $R^{4'}$ are hydrogen atoms (b) a 1-aryl-1,8-naphthylidin-4-one derivative where $R^1$ is a phenyl group (c) a 1-aryl-1,8-naphthylidin-4-one derivative where $R^1$ is a tolyl group (d) a 1-aryl-1,8-naphthylidin-4-one derivative where $R^1$ is an anisil group (e) a 1-aryl-1,8-naphthylidin-4-one derivative where $R^1$ is a phenyl group substituted with a halogen atom (f) a 1-aryl-1,8-naphthylidin-4-one derivative where $R^1$ is a pyridyl group (g) a 1-aryl-1,8-naphthylidin-4-one derivative where $R^1$ is a thiazolyl group (h) a 1-aryl-1,8-naphthylidin-4-one derivative where one of $R^5$ or $R^6$ is a hydrogen atom (i) a 1-aryl-1,8-naphthylidin-4-one derivative where one of $R^5$ or $R^6$ is 4-pyridyl group and the other is a hydrogen atom (j) a 1-aryl-1,8-naphthylidin-4-one derivative where one of $R^5$ or $R^6$ is 3-pyridyl group and the other is a hydrogen atom (k) a 1-aryl-1,8-naphthylidin-4-one derivative where one of $R^5$ or $R^6$ is a 2-pyridyl group and the other is a hydrogen atom (l) a 1-aryl-1,8-naphthylidin-4-one derivative where one of $R^5$ or $R^6$ is a 2,6-dichlorophenyl group and the other is a hydrogen atom (m) a 1-aryl-1,8-naphthylidin-4-one derivative where one of $R^5$ or $R^6$ is a 3,5-dichloropyridin-4-yl group and the other is a hydrogen atom (n) a 1-aryl-1,8-naphthylidin-4-one derivative where X is a group $NR^5R^6$.

The compound of the present invention has one or more asymmetric carbon atoms. Based on this, there are (R)-isomers, (S)-isomers, and other optical isomers, racemics, diastereomers, etc. Further, depending on the type of the substituent group, there are double bonds, and therefore, there are also (Z)-isomers, (E)-isomers, and the other geometrical isomers. The present invention includes these isomers separated from each other or in mixtures.

The compounds of the present invention include those capable of forming salts with acids. As the salts, acid addition salts with a mineral acid such as hydrochloric acid, a hydrobromic acid, a hydroiodic acid, a sulfuric acid, a nitric acid, a phosphoric acid, and with an organic acid such as a formic acid, an acetic acid, a propionic acid, an oxalic acid, a malonic acid, a succinic acid, a fumaric acid, a maleic acid, a lactic acid, a malic acid, a citric acid, a tartaric acid, a picric acid, a methanesulfonic acid, a trichloroacetic acid, a trifluoroacetic acid, an asparatic acid, a glutamic acid. Further, the compounds of the present invention can be isolated as a hydrate, ethanol, isopropanol, or other solvate or various crystalline substance.

The compound of formula (I) or (I') according to the present invention may be synthesized by, for example, the following method.

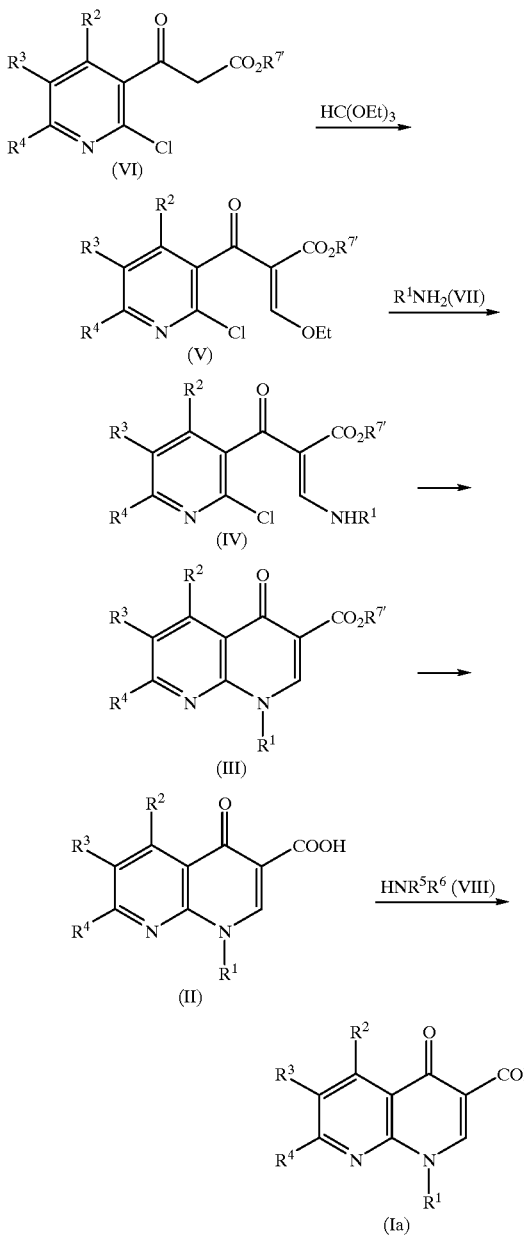

wherein, $R^1$, $R^2$, $R^3$, $R^4$, $R^5$ and $R^6$ are as defined above and $R^{7'}$ indicates $R^7$ as defined above except for a hydrogen atom or a protective group of the carboxylic acid such as a benzyl group, an allyl group, etc.

To carry out the present method, a compound (V) is obtained from the compound (VI) according to a known method (for example, J. Med. Chem. 1986, 29, 2363, ibid. 1985, 28, 1558). This reaction causes 1 to 3 equivalents, preferably 1.5 equivalents, based upon the compound (VI), of a trialkylformate such as triethylformate etc. to act on the compound (VI) in 10 to 20 equivalents of acetic anhydride at 100 to 140° C. and distills off the solvent after the end of the reaction so as to obtain the desired compound (V). If necessary, the resultant product may be purified by vacuum distillation, etc.

Note that the starting material, that is, the compound (VI), is either a known compound or is obtained from ethyl malonate magnesium salt, 2-chloronicotinic acid, 2,6-dichloronicotinic acid, 2-chloro-6-methylnicotinic acid, or the like in accordance with a known method (for example, J. Med. Chem. 1986, 29, 2363). It is possible to obtain the compound (IV) from the compound (V) obtained according to a known method (for example, J. Med. Chem. 1986, 29, 2363, ibid. 1985, 28, 1558). One equivalent, with respect to the compound (V), of a commercially available (or known) primary arylamine or heteroarylamine (VII) (for example, aniline, aminonaphthalene, aminopyridine, aminochloropyridine, aminofluoropyridine, nitroaniline, phenylenediamine, etc.) is used in halogenated hydrocarbon such as methylene chloride or aromatic hydrocarbon such as toluene, benzene, or ether such as diethyl ether, tetrahydrofuran, or a mixture thereof at 0° C. to room temperature. After the end of the reaction, the resultant product is diluted with an organic solvent, which is not miscible with water, then is successively washed with water and saturated saline. The solvent is then distilled off, whereupon it is possible to obtain the desired compound (IV). If necessary, the resultant product may be purified by column chromatography etc.

The compound (IV) obtained may be processed by a known method (for example, J. Med. Chem. 1986, 29, 2363, ibid. 1985, 28, 1558) to obtain a compound (III). 1 to 1.2 equivalents, based on the compound (IV), of an alkali metal hydride such as sodium hydride, potassium hydride, or lithium diisopropylamide, lithium hexamethyldisilazane, or other strong base, preferably sodium hydride, is used in a halogenated hydrocarbon such as methylene chloride, an aromatic hydrocarbon such as toluene, benzene or an ether such as diethyl ether, tetrahydrofuran, or a mixture thereof at 0° C. to room temperature. After the end of the reaction, the resultant product is diluted with an organic solvent, which is not miscible with water, then is successively washed with water and saturated saline. The solvent is then distilled off, whereupon it is possible to obtain the desired compound (III). If necessary, the resultant product may be purified by column chromatography etc.

The compound (III) thus obtained is hydrolyzed according to a known method to obtain a compound (II). The method differs depending on the $R^{7'}$, but normally can be performed under basic conditions (for example, J. Med. Chem. 1984, 27, 292) or acidic conditions (J. Med. Chem. 1986, 29, 2363).

Under basic conditions, 1 to 1.2 equivalents, based upon the compound (III), of alkali metal hydroxide such as sodium hydroxide, potassium hydroxide, is used in water or an alcohol such as ethanol, methanol, or ether such as diethyl ether, tetrahydrofuran, dioxane, or a mixture thereof at room temperature to 60° C. After the end of the reaction, the reaction solution is made weakly acidic, is diluted with an organic solvent, which is not miscible with water, and is successively washed with water and saturated saline. The solvent is then distilled off to obtain the desired compound (II). If necessary, the resultant product may be purified by recrystallization etc. Under acidic conditions, an acid catalyst such as sulfuric acid, hydrogen chloride, is made to act in water or an alcohol such as ethanol, methanol, or an ether such as diethyl ether, tetrahydrofuran, dioxane, or a mixture thereof at 60° C. to 100° C. After the end of the reaction, the solvent is distilled off to obtain the desired compound (II). If necessary, the resultant product may be purified by recrystallization etc.

When employing a special substituent group as a protective group of the carboxylic acid in $R^{7'}$ of formula (VI), it is also possible to convert the substance to the compound (II) by that substituent group under neutral conditions. For example, when employing a benzyl group in $R^7$, it is possible to convert the substance to the compound (II) by hydrolysis under neutral conditions. When an allyl group is employed in $R^{7'}$, it is possible to convert it to the compound (II) by formic acid in the presence of a Pd(O) complex. The compound (II) obtained can be used to obtain the compound (Ia) in the compounds having the formula (I) of the present invention where X is the group $NR^5R^6$ according to a known method (Fourth Experimental Chemical Seminar, vol. 22, p. 137, published by MARUZEN).

The reaction synthesizes an acid amide from a carboxylic acid (II) and commercially available or known amine component (VIII) (for example, methylamine, ethylamine, isopropylamine, benzylamine, phenylethylamine, aniline, toluidine, aminobenzoic acid, aminoacetophenone, dichloroaniline, aminonaphthalene, aminopyridine, aminodichloropyridine, aminofluoropyridine, phenylenediamine, diaminopyridine, nitroaniline, etc.). This may be done by various methods, but these may be roughly divided into three groups. The first are methods where a condensation agent such as dicyclohexyl carbodiimide, carbonyl diimidazole, is used to cause a reaction between a carboxylic acid (II) and amine component (VIII). The second are methods where a carboxylic acid (II) is converted to an acid halide, then allowed to react with an amine component (VIII). The third are methods where carboxylic acid (II) is converted to an acid anhydride, then allowed to react with an amine component (VIII).

For example, as a method going through an acid halide, 1 to 5 equivalents, based upon the carboxylic acid (II), of an acid halogenating agent such as thionyl chloride, oxalyl chloride, phosphorus pentachloride, is used a halogenated hydrocarbon such as methylene chloride, chloroform aromatic hydrocarbon such as toluene, benzene, an ether such as tetrahydrofuran, 1,4-dioxane, or a mixture thereof or without using a solvent at room temperature to 100° C. After the end of the reaction, the solvent is distilled off to obtain the acid halide. The acid halide may be used as it is, without purifying for the next reaction. 2 to 3 equivalents, based on the acid halide, of the amine component (VIII) is reacted in a halogenated hydrocarbon such as methylene chloride, aromatic hydrocarbon such as toluene, benzene, an ether such as diethyl ether, or a mixture thereof at 0° C. to room temperature, or 1 to 1.5 equivalents of the amine component (VIII) is reacted in the presence of 1 to 3 equivalents of an amine such as triethylamine, diisopropylethylamine, pyridine, or the amine component (VIII) may be reacted with the acid halide component after reacting with an alkali metal hydride such as sodium hydride or potassium hydride to form the corresponding amine metal salt. After the end of the reaction the substance is diluted with an organic solvent which is not miscible with water, then is successively washed with water and saturated saline. The solvent is then distilled off to obtain the desired compound (Ia). If necessary, the product may be purified by column chromatography, recrystallization, etc.

In the process of the present invention, it was possible to introduce $R^1$ substituent group, which was difficult to be introduced, by the use thereof in the form of the amine component (VII).

The type IV phosphodiesterase inhibiting activities of the compounds according to the present invention were confirmed by the following test:

(1) Method of Measurement of Type IV Phosphodiesterase Inhibiting Activity

The following assay was used to evaluate the ability of the compound of the present invention to suppress type IV phosphodiesterase, according to Biochemical. Pharmacol. 48 (6), 1219–1223 (1994).

1) Type IV phosphodiesterase activity fractions were prepared as follows. Human histiocytic lymphoma cell line U937 was cultured in an RPMI1640 medium containing 10% fetal calf serum to obtain 109 cells of U937. The cells were recovered by centrifugation and suspended in 40 ml of buffer A (20 mM bis-tris, 5 mM 2-mercaptoethanol, 2 mM benzamidine, 2 mM EDTA, 0.1 mM 4-(2-aminoethyl) benzensulfonyl hydrochloride, 50 mM sodium acetate, pH=6.5). The cells were broken by a sonication and centrifuged (4° C., 10,000G, 10 minutes) to obtain a supernatent. This was filtered by a 0.45 tm filter to obtain the soluble fraction.

The soluble fraction obtained was applied into a 1×10 cm DEAE Sepharose column equalibrated with the buffer A. 120 ml of the buffer A containing a linear gradient solution of 0.05 to 1 M sodium acetate was used to separate the phosphodiesterase and recover 24 5-ml fractions. Each of the fractions was measured for the cAMP phosphodiesterase activity. The fractions having cAMP phosphodiesterase activity which could be inhibited by 30 $\mu$M rolipram (selective type IV phosphodiesterase inhibitor) were collected and used as a stored solution for examination of the type IV phosphodiesterase inhibiting activity.

2) The test compound was reacted at a desired concentration in a reaction mixture containing 20 mM tris-HCl (pH7.5), 1 mM $MgCl_2$, 100 pM EDTA, 330 $\mu$g/ml calf serum albumin, 10 $\mu$g/ml 5'-nucleotidase, 0.4 $\mu$Ci $^3$H-cAMP (0.28 mM cAMP) and the type TV phosphodiesterase stored solution at 30° C. for 30 minutes. QAE-Sephadex suspended in 10 mM of hepes-Na (pH-7.0) was added to the reaction mixture which was then allowed to stand for 5 minutes, then the supernatant was obtained, QAE-Sephadex was further added, to the supernatant, and was allowed to stand for 5 minutes, then the supernatant was obtained and measured for radioactivity.

The $IC_{50}$ was measured for each compound as the concentration of the test compound inhibiting 50% of the type IV phosphodiesterase activity.

(2) Type IV Phosphodiesterase Inhibiting Activity of Various Compounds

The phosphodiesterase inhibiting activity $IC_{50}$ obtained by the above method of measurement is shown in the following Table I. As the typical control agent, Rolipram (Tocris) was used.

Further, as a Comparative Example, the compound N-(2-(4-pyridyl)ethyl)-1-ethyl-7-methyl-1,4-dihydro[1,8] naphthylidin-4-one-3-carboxyamide described in WO-A-97-04775 (1997), page 17, Example 1 was synthesized and measured similarly for inhibiting activity. The phosphodiesterase inhibiting activity $IC_{50}$ obtained is shown in Table I.

TABLE I

| Compound | PDE IV-$IC_{50}$ ($\mu$M) |
|---|---|
| Example 19 | 0.93 |
| Example 24 | 0.60 |
| Example 51 | 1.40 |
| Example 52 | 0.15 |
| Example 53 | 0.027 |
| Example 54 | 0.035 |
| Example 55 | 0.031 |
| Example 56 | 0.026 |
| Example 57 | 0.71 |
| Example 58 | 0.42 |
| Example 59 | 0.64 |
| Example 61 | 0.39 |
| Example 62 | 1.60 |

TABLE I-continued

| Compound | PDE IV-IC$_{50}$ ($\mu$M) |
|---|---|
| Example 63 | 1.20 |
| Example 64 | 0.12 |
| Example 65 | 0.27 |
| Example 67 | 0.060 |
| Example 69 | 0.013 |
| Example 70 | 0.61 |
| Example 72 | 0.18 |
| Example 73 | 0.81 |
| Example 74 | 0.42 |
| Example 75 | 0.10 |
| Example 76 | 0.50 |
| Example 77 | 0.18 |
| Example 79 | 0.055 |
| Example 80 | 0.11 |
| Example 81 | 0.11 |
| Example 85 | 0.55 |
| Example 86 | 0.032 |
| Example 87 | 0.072 |
| Example 90 | 0.096 |
| Example 91 | 0.052 |
| Example 92 | 0.14 |
| Example 93 | 0.016 |
| Example 94 | 0.35 |
| Example 97 | 0.47 |
| Example 98 | 0.16 |
| Example 99 | 0.0034 |
| Example 100 | 0.65 |
| Example 102 | 0.035 |
| Example 103 | 0.059 |
| Example 104 | 0.019 |
| Example 105 | 0.085 |
| Example 106 | 0.0004 |
| Example 107 | 0.52 |
| Example 108 | 0.0046 |
| Example 109 | 0.40 |
| Example 113 | 0.044 |
| Example 114 | 0.21 |
| Example 118 | 0.0002 |
| Example 119 | 0.25 |
| Example 120 | 0.099 |
| Example 121 | 0.0031 |
| Example 122 | 0.058 |
| Example 123 | 0.0006 |
| Example 124 | 0.11 |
| Example 125 | 0.0008 |
| Example 127 | 0.056 |
| Example 130 | 0.26 |
| Example 131 | 0.59 |
| Example 132 | 0.76 |
| Example 133 | 0.0064 |
| Example 134 | 0.47 |
| Example 135 | 0.13 |
| Example 136 | 0.0008 |
| Example 137 | 0.0049 |
| Example 138 | 0.044 |
| Example 139 | 0.070 |
| Example 140 | 0.036 |
| Example 141 | 0.0005 |
| Example 143 | 0.14 |
| Example 144 | 0.14 |
| Example 145 | 0.40 |
| Example 146 | 0.0017 |
| Example 147 | 0.0011 |
| Example 149 | 0.94 |
| Example 152 | 0.0059 |
| Rolipram | 0.46 |
| Comp. Ex. | 5.20 |

As a result of the test on the phosphodiesterase inhibiting activity, it was confirmed that the 1-aryl-1,8-naphthylidin-4-one derivative according to the present invention exhibited an excellent inhibitory effect.

The inhibitory activities of the compound of the present invention on TNF-α production by LPS stimulated macrophages were confirmed by the following test:

(1) Method of Measurement of TNF-α Production Inhibitory Activity by LPS Stimulated Macrophaaes The following assay was used to evaluate the ability of the compound of the present invention to suppress TNF-α production by LPS stimulated macrophages according to Immuno pharmacol. 29, 121–127 (1995).

1) 6 to 10 week old female BALB/c mice were used, 2 ml portions of thioglycolate were intraperitoneally administered, and the abdominal cavities were washed by 10 ml of PBS after 4 days, whereby 1 to 2×10$^7$ peritoneal cells were obtained per mouse. These were suspended in a hemocyte solution (0.75% ammonium chloride, 17 mM tris-hydrochlorate buffer, pH7.2), centrifuged, then resuspended in an RPMI1640 medium including 10% fetal calf serum and seeded in a 96-well cell culture plate at a density of 1×10$^5$ cells/50 $\mu$l/well. Since these cells adhered strongly to the tissue culture plate and were positive in nonspecific esterase staining, they were used for the test as mouse peritoneal macrophages. Mouse peritoneal macrophages were precultured overnight at 37° C. in 5% CO$_2$ for the experiment.

2) *E. Coli* (serum type 055: B5) derived LPS was dissolved in PBS in a concentration of 1 mg/ml, then sterilized by filtration. The test compound was dissolved in DMSO to make a 1000-fold concentration solution of the final concentration of use. 10 $\mu$l of the above LPS stock solution (final concentration 10 $\mu$g/ml) and 1 $\mu$l of the tested substance stock solution were added and mixed in 0.5 ml of RPMI1640 medium containing 10% fetal calf serum. This was added to the above cells at 50 $\mu$l/well and cultured for 8 hours. The cultured supernatant was recovered from each well and the TNF-α concentration was measured by the ELISA method (Cytoscreen® Immunoassay Kit Mouse TNF-α, BioSource International).

3) The IC$_{50}$ was calculated for each compound as the concentration of the test compound inhibiting 50% of the TNF-α production caused by LPS stimulus.

(2) TNF-α Production Inhibitory Activity by LPS Stimulated Macrophages

The IC$_{50}$ values for the TNF-α production inhibitory activity obtained by the above method are shown in the following Table II. The comparative example was the compound described in WO-A-97-04775, Example 1, mentioned above.

TABLE II

| Compound | TNF-α production inhibitory activity IC$_{50}$ ($\mu$M) |
|---|---|
| Example 51 | 0.40 |
| Example 53 | 0.010 |
| Example 54 | 0.10 |
| Example 55 | 0.10 |
| Example 56 | 0.004 |
| Example 57 | 1.0 |
| Example 58 | 0.42 |
| Example 61 | 1.0 |
| Example 64 | 0.10 |
| Example 65 | 0.60 |
| Example 67 | 0.70 |
| Example 69 | 0.10 |
| Example 70 | 1.0 |
| Example 72 | 0.01 |
| Example 73 | 1.0 |
| Example 74 | 0.40 |
| Example 75 | 0.20 |
| Example 77 | 0.10 |
| Example 79 | 0.30 |
| Example 80 | 0.10 |
| Example 81 | 0.50 |

TABLE II-continued

| Compound | TNF-α production inhibitory activity IC$_{50}$ ($\mu$M) |
| --- | --- |
| Example 86 | 0.40 |
| Example 87 | 0.20 |
| Example 90 | 0.50 |
| Example 91 | 0.10 |
| Example 92 | 0.20 |
| Example 93 | 0.030 |
| Example 94 | 0.50 |
| Example 98 | 1.0 |
| Example 99 | 0.025 |
| Example 102 | 0.10 |
| Example 103 | 0.10 |
| Example 104 | 0.003 |
| Example 105 | 0.40 |
| Example 106 | 0.01 |
| Example 107 | 1.0 |
| Example 108 | 1.0 |
| Example 109 | 0.40 |
| Example 113 | 0.06 |
| Example 114 | 0.10 |
| Example 118 | 0.0004 |
| Example 119 | 0.70 |
| Example 122 | 0.001 |
| Example 125 | 0.0005 |
| Example 127 | 0.30 |
| Example 132 | 1.0 |
| Example 133 | 0.004 |
| Example 134 | 0.80 |
| Example 135 | 0.50 |
| Example 136 | 0.003 |
| Example 137 | 0.004 |
| Example 138 | 0.40 |
| Example 139 | 0.10 |
| Example 140 | 0.005 |
| Example 141 | 0.001 |
| Example 143 | 0.15 |
| Example 144 | 0.70 |
| Example 146 | 0.010 |
| Example 147 | 0.020 |
| Example 150 | 0.40 |
| Example 152 | 0.030 |
| Rolipram | 0.10 |
| Comp. Ex. | 10.0 |

From the above results, it was confirmed that the compound of the present invention exhibits an excellent activity inhibiting the production of TNF-α.

The compound of the present invention is useful as a pharmaceutical composition for the prevention or treatment of bronchial asthma, chronic bronchitis, and other respiratory diseases, diseases relating to abnormality of the nervous system such as Alzheimer's Disease, Parkinson's Disease, diseases relating to mental abnormalities such as maniac depression, inflammatory diseases such as atopic dermitis, acquired immunity disorder syndrome general or local joint diseases such as osteoarthritis, rheumatoid arthritis, Crohn disease, sepsis, endotoxin shock and other diseases related to tumor necrosis factor (TNF-α) or other various cytokine (IL-1, IL-6, etc.), and the like by selectively inhibiting the type IV phosphodiesterase and further inhibiting the production of TNF-α.

The type IV phosphodiesterase inhibitor of the present invention is useful as an agent for the prevention or treatment of specifically respiratory diseases (for example, bronchial asthma, chronic bronchitis, pneumonia type diseases, adult respiratory distress syndrome, etc.), diseases relating to abnormality of the nervous system (for example, impaired learning, memory, and recognition relating to Alzheimer's Disease, Parkinson's Disease, and the like, multiple lateral sclerosis, senile dementia, amyotrophic lateral sclerosis, muscular distrophy, etc.), diseases relating to mental abnormalities (for example, maniac depression, schizophrenia, neurosis, etc.), inflammatory diseases (for example, atopic dermitis, conjunctivitis, acquired immunity disorder syndrome, keloids, etc.), general and local joint diseases (for example, osteoarthritis, rheumatoid arthritis, and other general or local joint diseases, gouty arthritis, rheumatoid arthritis, nodose rheumatism, etc.), tumor necrosis factor (TNF) and other cytokine (IL-1, IL-6, etc.) related diseases (for example, psoriasis, rheumatoid arthritis, Crohn disease, septicemia, sepsis, endotoxic shock, nephritis, pneumonia, bacterial or viral infection, cardiac incompetence, ateriosclerosis, cardiac infarction, etc.) etc.

For use of the effective ingredient of the present invention as a pharmaceutical or a type IV phosphodiesterase inhibitor, one or more types of the compound of the present invention may be formulated and formed into preparations suitable for the method of administration according to ordinary methods. For example, for oral administration, capsules, tablets, granules, powders, syrups, dry syrups, and other preparations may be mentioned, while for nonoral administration, injections and also rectal suppositories, vaginal suppositories, and other suppositories, sprays and other nasal agents, ointments, transdermal absorption type tapes, and other transdermal absorption agents may be mentioned.

The clinical dosage of the compound of the present invention differs depending on the symptoms, the severity of the disease, the age, and complications of the patient to which the compound is being administered and differs depending on the preparation as well, but in the case of oral administration is normally 1 to 1000 mg, preferably 1 to 500 mg, more preferably 5 to 100 mg. per adult per day as effective ingredient, and in the case of nonoral administration is one-tenth to one-half of the case of oral administration. The dosage may be suitably adjusted according to the age, symptoms, etc. of the patient.

The compound of the present invention is a selective inhibitor for type IV phosphodiesterase and has over 10-times the selectivity over other phosphodiesterase isoenzymes (i.e., PDE I–III, V and VII). Due to this, it is expected that there will be few side effects due to the action of inhibiting other phosphodiesterase isoenzymes. The compound of the present invention is low in toxicity. The compound is expected to be high in safety. For example, the compounds of Examples 99, 102, 103, 106, 139 and 141 exhibited no death when 10 mg/kg per day was administered for 28 days to mice.

The 1-aryl-1,8-naphthylidin-4-one derivative or its pharmaceutically acceptable salt or solvate of the present invention is useful as a pharmaceutical composition for the prevention or treatment of diseases involving type IV phosphodiesterase. As specific examples of diseases involving type IV phosphodiesterase, for example, respiratory diseases (for example, bronchial asthma, chronic bronchitis, pneumonia type diseases, adult respiratory distress, etc.), diseases relating to abnormality of the nervous system (for example, impaired learning, memory, and recognition relating to Alzheimer's Disease, Parkinson's Disease, and the like, multiple lateral sclerosis, senile dementia, amyotrophic lateral sclerosis, muscular distrophy, etc.), diseases relating to mental abnormalities (for example, maniac depression, schizophrenia, neurosis, etc.), inflammatory diseases (for example, atopic dermitis, conjunctivitis, acquired immunity disorder syndrome, keloids, etc.), general and local joint diseases (for example, osteoarthritis, rheumatoid arthritis, and other general or local joint diseases, gouty arthritis, rheumatoid arthritis, nodose rheumatism, etc.), tumor necrosis factor (TNF) and other cytokine (IL-1, IL-6, etc.) related diseases (for example, psoriasis, rheumatoid arthritis, Crohn disease, septicemia, sepsis, endotoxic shock, nephritis, pneumonia, bacterial or viral infection, cardiac incompetence, ateriosclerosis, cardiac infarction, etc.) etc. may be mentioned.

EXAMPLE

The present invention will now be further explained in detail by, but is by no means limited to, the following Examples.

Example 1

Synthesis of ethyl 3-(4-fluoroanilino)-2-(2-chloronicotinoyl)acrylate

A mixed solution of ethyl 2-chloronicotinoyl acetate (410 mg, 1.8 mmol) in triethylformate (449 µl, 2.7 mmol) and acetic anhydride (2.04 ml, 21.6 mmol) was heated and stirred at 130° C. for 1 hour. The solution was cooled, then the solvent was distilled off under vacuum to obtain an oily substance. This oily substance was dissolved in methylene chloride (7 ml), 4-fluoroaniline (188 µl, 1.98 mmol) was added at room temperature, and the solution was stirred at that temperature for 1.5 hours. Next, the solvent was distilled off under vacuum and the residue was purificated by silica gel column chromatography (hexane/ethyl acetate=2/1) to obtain the above-identified compound (510 mg, 81%) as a slightly yellow crystal.

MS(FAB) 348[M+1]$^+$. 1H-NMR(CDCl$_3$): δ 0.97(3H, t, J=7.1 Hz) 4.03(2H, q, J=7.1 Hz) 7.10–7.18(2H, m) 7.23–7.32(3H, m) 7.56–7.63(1H, m) 8.37–8.42(1H, m) 8.59 (1H, d J=13.6 Hz) 12.65–12.76(H, m).

Example 2

Synthesis of ethyl 1-(4-fluorophenyl)-1,4-dihydro[1,8]naphthylidin-4-one-3-carboxylate Sodium hydride (abt. 60% oil suspension 429 mg, 10.7 mmol) was added to a tetrahydrofuran (45 ml) solution of ethyl 3-(4-fluoroanilino)-2-(2-chloronicotinoyl) acrylate (3.56 g, 10.2 mmol) at 0° C. and the solution was stirred at that temperature for 5 minutes. It was further stirred at room temperature for 1 hour, then water (100 ml) was added and extraction was performed with ethyl acetate (200 ml). Next, the organic layer was washed with saturated saline (50 ml), then dried over anhydrous sodium sulfate, then the solvent was distilled off under vacuum. The precipitated crystal was washed with diethyl ether and the crystal was obtained by filtration to obtain the above-identified compound (2.84 g, 89%) as a colorless crystal.

IR(KBr)cm$^{-1}$: 2982, 1690, 1649, 1511. MS(FAB) 313 [M+1]$^+$. 1H-NMR(CDCl$_3$): δ 1.41(3H, t, J=7.1 Hz) 4.41(2H, q, J=7.1 Hz) 7.23–7.41 (2H, m) 7.48–7.56 (3H, m) 8.63(1H, dd, J=1.8 and 4.5 Hz) 8.67(1H, s) 8.82(1H, dd, J=1.8 and 7.8 Hz).

Example 3

Synthesis of 1-(4-fluorophenyl)-1,4-dihydro[1,8]naphthylidin-4-one-3-carboxylic acid 1N sodium hydroxide solution (5.3 ml, 5.3 mmol) was added to a mixed solution of ethyl 1-(4-fluorophenyl)-1,4-dihydro[1,8]naphthylidin-4-one-3-carboxylate (1.5 g, 4.8 mmol) in tetrahydrofuran (40 ml) and ethanol (50 ml) at room temperature and the solution was stirred at that temperature for 1.5 hours. Next, this was diluted by ethyl acetate (200 ml) and 1N hydrochloric acid (5.5 ml) was added. The organic layer was successively washed with water (30 ml) and saturated saline (30 ml), then dried over anhydrous sodium sulfate, then the solvent was distilled off under vacuum. The precipitated crystal was washed by diethyl ether, then the crystal was obtained by filtration to obtain the above-identified compound (1.2 g, 88%) as a colorless crystal.

IR(KBr)cm$^{-1}$: 3063, 1728, 1620, 1465 MS(FAB) 285[M+ 1]$^+$. 1H-NMR(CDCl$_3$): δ 7.26–7.34(2H, m) 7.40–7.47(2H, m) 7.57(1H, dd, J=4.5 and 8.1 Hz) 8.79 (1H, dd, J=2.0 and 4.5 Hz) 8.88(1H, dd, J=1.9 and 8.0 Hz) 8.99(1H, s).

Example 4

Synthesis of ethyl 1-phenyl-1,4-dihydro[1,8] naphthylidin-4-one-3-carboxylate

A mixed solution of ethyl 2-chloronicotinoyl acetate (455 mg, 2 mmol) in triethylformate (500 µl, 3.0 mmol) and acetic anhydride (2.4 ml) was heated and stirred at 130° C. for 1.5 hour. The solution was cooled, then the solvent was distilled off under vacuum to obtain an oily substance. This oily substance was dissolved in methylene chloride (7 ml), aniline (200 µl, 2.2 mmol) was added at room temperature, and the solution was stirred for 1.5 hours. Sodium hydride (abt. 90 mg of 60% oil suspension, 2.25 mmol) was added, after ice cooling, and the solution was stirred at that temperature for 5 minutes. This was further stirred at room temperature for 1 hour, then water (20 ml) was added and extraction was performed with ethyl acetate (20 ml). Next, the organic layer was washed with saturated saline (10 ml), then dried over anhydrous sodium sulfate and the solvent was distilled off under vacuum. The precipitated crystal was washed with diethyl ether, then the crystal was obtained by filtration to obtain the above-identified compound (411 mg, 70%) as a colorless crystal.

IR(KBr)cm$^{-1}$: 3053, 2984, 1732, 1693, 1639, 1597, 1433, 1247, 1131, 782, 702. MS(FAB) 295[M+1]$^+$. 1H-NMR (CDCl$_3$): δ 1.41(3H, t, J=7.1 Hz) 4.42(2H, q, J=7.1 Hz) 7.41(3H, m) 7.56(3H, m) 8.63(1H, dd, J=1.8 and 4.5 Hz) 8.70 (1H, s) 8.83(1H, dd, J=1.8 and 7.8 Hz).

Example 5

Synthesis of 1-phenyl-1,4-dihydro[1,8]naphthylidin-4-one-3-carboxylic acid

The same reaction was carried out as in Example 3, except for using ethyl 1-phenyl-1,4-dihydro[1,8]naphthylidin-4-one-3-carboxylate, instead of ethyl 1-(4-fluorophenyl)-1,4-dihydro[1,8]naphthylidin-4-one-3-carboxylate, to obtain the above-identified compound (348 mg, quantitative) as a colorless crystal.

MS(FAB) 267[M+1]$^+$. 1H-NMR(CDCl$_3$): δ 7.44(2H, m) 7.55–7.63(4H, m) 8.79(1H, dd, J=1.9 and 4.4 Hz) 8.88(1H, dd, J=1.9 and 8.0 Hz) 9.01(1H, s) 14.30 (1H, s).

Example 6

Synthesis of ethyl 3-(4-tolyl)-2-(2-chloronicotinoyl) acrylate

The same reaction was carried out as in Example 1, except-for using 4-toluidine, instead of 4-fluoroaniline, to obtain the above-identified compound (1.25 g, 83%) as a slightly yellow crystal.

IR(KBr)cm$^{-1}$: 1687, 1620, 1602, 1550, 1395, 1302, 1255, 825. MS(FAB) 345[M+1]$^+$. 1H-NMR(CDCl$_3$): δ 0.83 and 0.97(total 3H, t, J=7.1 Hz) 2.38(3H, s) 4.01 and 4.03(total 2H, q. J=7.1 Hz) 7.13–7.30(5H, m) 7.59 and 7.63(total 1H, dd, J=1.8 and 7.4 Hz) 8.40(1H, dd, J=1.8 and 4.8 Hz) 8.63–8.74(1H, m) 12.70–12.74(1H, m).

Example 7

Synthesis of ethyl 1-(4-tolyl)-1,4-dihydro[1,8]naphthylidin-4-one-3-carboxylate The same reaction was carried out as in Example 2, except for using ethyl 3-(4-tolyl)-2-(2-chloronicotinoyl)acrylate, instead of ethyl 3-(4-fluoroanilino)-2-(2-chloronicotinoyl)acrylate, to obtain the above-identified compound (1.00 g, 94%) as a slightly yellow crystal.

IR(KBr)cm$^{-1}$: 2938, 1727, 1625, 1601, 1511, 1475, 1424, 1204, 795. MS(FAB) 309[M+1]$^+$. 1H-NMR(CDCl$_3$): δ 1.40 (3H, t, J=7.1 Hz) 2.47(3H, s) 4.40(2H, q, J=7.1 Hz) 7.24–7.42(5H, m) 8.64(1H, dd, J=1.9 and 4.5 Hz) 8.67–8.69 (1H, m) 8.83(1H, dd, J=1.9 and 7.9 Hz).

Example 8

Synthesis of 1-(4-tolyl)-1,4-dihydro[1,8]naphthylidin-4-one-3-carboxylic acid

The same reaction was carried out as in Example 3, except for using, ethyl 1-(4-tolyl)-1,4-dihydro[1,8]naphthylidin-4-one-3-carboxylate, instead of ethyl 1-(4-fluorophenyl)-1,4-dihydro[1,8]naphtylidin-4-one-3-carboxylate, to obtain the above-identified compound (782,mg, 91%) as a colorless crystal.

IR(KBr)cm$^{-1}$: 1720, 1619, 1560, 1544, 1451, 1332, 796. MS(FAB) 281[M+1]$^+$. 1H-NMR(CDCl$_3$): δ 2.49(3H, s) 7.30–7.32(2H, m) 7.39–7.41(2H, m) 7.53–7.57(1H, m) 8.80 (1H, dd, J=1.9 and 4.5 Hz) 8.88(1H, dd, J=1.9 and 8.1 Hz) 9.00(1H, s) 14.34(1H, brs).

Example 9

Synthesis of ethyl 3-(4-methoxyphenyl)-2-(2-chloronicotinoyl)acrylate

The same reaction was carried out as in Example 1, except for using 4-anisidine, instead of 4-fluoroaniline, to obtain the above-identified compound (1.59 g, 84%) as a slightly yellow crystal.

IR(KBr)cm$^{-1}$: 1702; 1622,1513, 1391, 1297, 1243, 1112. MS(FAB) 361 [M+1]$^+$. 1H-NMR(CDCl$_3$): δ 0.83 and 0.96 (total 3H, t, J=7.1 Hz) 3.84(3H, s) 4.03(2H, q, J=7.1 Hz) 6.95–6.99(2H, m) 7.21–7.30(3H, m) 7.58(1H, dd, J=1.9 and 7.5 Hz) 8.40(1H, dd, J=1.9 and 4.8 Hz) 8.57–8.70(1H, m) 12.77–12.80(1H, m).

Example 10

Synthesis of ethyl 1-(4-methoxyphenyl)-1,4-dihydro[1,8]naphthylidin-4-one-3-carboxylate The same reaction was carried out as in Example 2, except for using ethyl 3-(4-methoxyphenyl)-2-(2-chloronicotinoyl)acrylate, instead of ethyl 3-(4-fluoroanilino)-2-(2-chloronicotinoyl)acrylate, to obtain the above-identified compound (1.16 g, 86%) as a slightly yellow crystal.

IR(KBr)cm$^{-1}$: 1725, 1627, 1627, 1604, 1514, 1428, 1357, 1248. MS(FAB) 325[M+1]$^+$. 1H-NMR(CDCl$_3$): δ 1.41(3H, t, J=7.1 Hz) 3.90(3H, s) 4.42(2H, q. J=7.1 Hz) 7.06–7.08 (2H, m) 7.33–7.41 (3H, m) 8.65(1H, dd, J=1.9 and 4.5 Hz) 8.68(1H, s) 8.82(1H, dd, J=1.9 and 8.0 Hz).

Example 11

Synthesis of 1-(4-methoxyphenyl)-1,4-dihydro[1,8]naphtylidin-4-one-3-carboxylic acid The same reaction was carried out as in Example 3, except-for using ethyl 1-(4-methoxyphenyl)-1,4-dihydro[1,8]naphtylidin-4-one-3-carboxylate, instead of ethyl 1-(4-fluorophenyl)-1,4-dihydro[1,8]naphtylidin-4-one-3-carboxylate, to obtain the above-identified compound (835 mg, 91%) as a colorless crystal.

IR(KBr)cm$^{-1}$: 1731, 1618, 1514, 1460, 1330, 1240, 1029, 799. MS(FAB) 297[M+1]$^+$. 1H-NMR(CDCl$_3$): δ 3.91(3H, s) 7.07–7.10(2H, m) 7.33–7.35(2H, m) 7.53–7.57(1H, m) 8.80 (1H, dd, J=1.9 and 4.5 Hz) 8.87(1H, dd, J=1.9 and 8.0 Hz) 9.00(1H, s) 14.33(1H, s).

Example 12

Synthesis of ethyl 3-(4-chlorophenyl)-2-(2-chloronicotinoyl)acrylate

The same reaction was carried out as in Example 1, except for using 4-chloroaniline, instead of 4-fluoroaniline, to obtain the above-identified compound (1.09 g, 87%) as a colorless crystal.

IR(KBr)cm$^{-1}$: 1728, 1626, 1586, 1474, 1424, 1205, 1089. MS(FAB) 329[M+1]$^+$. 1H-NMR(CDCl$_3$) 61.41(3H, t, J=7.1 Hz) 4.41(2H, q, J=7.1 Hz) 7.38–7.44(3H, m) 7.55–7.57(2H, m) 8.63(1H, dd, J=1.9 and 4.5 Hz) 8.66(1H, s) 8.82 (1H, dd, J=1.9 and 7.99 Hz).

Example 13

Synthesis of ethyl 1-(4-chlorophenyl)-1,4-dihydro[1,8]naphtylidin-4-one-3-carboxylate The same reaction was carried out as in Example 2, except for using ethyl 3-(4-chlorophenyl)-2-(2-chloronicotinoyl)acrylate, instead of ethyl 3-(4-fluoroanilino)-2-(2-chloronicotinoyl)acrylate, to obtain the above-identified compound (1.09 g, 87%) as a colorless crystal.

IR(KBr)cm$^{-1}$: 1728, 1626, 1586, 1474, 1424, 1205, 1089. MS(FAB) 329[M+1]$^+$. 1H-NMR(CDCl$_3$): δ 1.41(3H, t, J=7.1 Hz) 4.41(2H, q, J=7.1 Hz) 7.38–7.44(3H, m) 7.55–7.57(2H, m) 8.63(1H, dd, J=1.9 and 4.5 Hz) 8.66(1H, s) 8.82 (1H, dd, J=1.9 and 7.9 Hz).

Example 14

Synthesis of 1-(4-chlorophenyl)-1,4-dihydro[1,8]naphtylidin-4-one-3-carboxylic acid The same reaction was carried out as in Example 3, except for using ethyl 1-(4-chlorophenyl)-1,4-dihydro[1,8]naphtylidin-4-one-carboxylate, instead of ethyl 1-(4-fluorophenyl)-1,4-dihydro[1,8]napthylidin-4-one-3-carboxylate, to obtain the above-identified compound (960 mg, quantitative) as a colorless crystal.

IR(KBr)cm$^{-1}$: 3062, 1737, 1619, 1469, 1408, 1328, 795. MS(FAB) 301[M+1]$^+$. 1H-NMR(CDCl$_3$): δ 7.37–7.40(2H, m) 7.56–7.60(3H, m) 8.78(1H, dd, J=1.9 and 4.5 Hz) 8.88(1H, dd, J=1.9 and 8.0 Hz) 8.98(1H, s) 14.20(1H, s).

Example 15

Synthesis of ethyl 3-(3-tert-butyldimethylsilyloxymethylphenyl)-2-(2-chloronicotinoyl)acrylate The same reaction was carried out as in Example 1, except for using 3-tert-butyldimethylsilyloxymethylaniline, instead of 4-fluoroaniline, to obtain the above-identified compound (1.47 g, 88%) as a yellow oily product.

IR(neat)cm$^{-1}$: 3208, 1704, 1621, 1574, 1397, 1255. MS(FAB) 475[M+1]$^+$. 1H-NMR(CDCl$_3$): δ 0.13(6H, s) 0.84 and 0.99(total 3H, t, J=7.1 Hz) 0.97(9H, s) 4.05 and 4.12 (total 2H, q, 7.1 Hz) 4.76–4.78(2H, m) 7.12–7.31(4H, m) 7.36–7.41(1H, m) 7.59 and 7.65(total 1H, dd, J=1.9 and 7.5 Hz) 8.40–8.42(1H, m) 8.67–8.77(1H, m) 11.30–12.73(1H, m).

Example 16

Synthesis of ethyl 1-(3-tert-butyldimethylsilyloxymethylphenyl)-1,4-dihydro[1,8]naphtylidin-4-one-3-carboxylate The same reaction was carried out as in Example 2, except for using ethyl 3-(3-tert-butyldimethylsilyloxymethylphenyl)-2-(2-chloronicotinoyl)acrylate, instead of ethyl 3-(4-fluoroanilino)-2-(2-chloronicotinoyl)acrylate, to obtain the above-identified compound (1.14 mg, 88%) as a slightly yellow crystal.

IR(KBr)cm$^{-1}$: 2928, 1737, 1634, 1474, 1423, 1255, 1082, 786. MS(FAB) 439[M+1]$^+$. 1H-NMR(CDCl$_3$): δ 0.12(6H, s) 0.94(9H, S) 1.40(3H, t, J=7.1 Hz) 4.40(2H, q, J=7.1 Hz) 4.84(2H, s) 7.30–7.35(1H, m) 7.38–7.42(2H, m) 7.50–7.55 (2H, m) 8.62(1H, dd, J=1.9 and 4.5 Hz) 8.70(1H, s) 8.83(1H, dd, J=1.9 and 7.8 Hz).

Example 17

Synthesis of 1-(3-tert-butyldimethylsilyloxymethylphenyl)-1,4-dihydro[1,8]naphthyldin-4-one-3-carboxylic acid The same reaction was carried out as in Example 3, except for using ethyl 1-(3-tert-butyldimethylsilyloxymethylphenyl)-1,4-dihydro[1,8]naphthylidine-4-one-3-carboxylate, instead of ethyl 1-(4-fluorophenyl)-1,4-dihydro[1,8]naphthylidin-4-one-3-carboxylate, to obtain the above-mentioned compound (810 mg, 79%) as a slightly yellow. crystal.

IR(KBr)cm$^{-1}$: 3067, 2930, 1719, 1630, 1427, 1333, 786. MS(FAB) 411[M+1]$^+$. 1H-NMR(CDCl$_3$): δ 0.12(6H, s) 0.93 (9H, s) 4.85(2H, s) 7.28–7.60(5H, m) 8.77–8.80(1H, m) 8.87–8.90(1H, m) 9.01(1H, s) 14.29–14.33(1H, m).

Example 18

Synthesis of ethyl 3-(3-nitroanilino)-2-(2-chloronicotinoyl)acrylate

The same reaction was carried out as in Example 1, except for using 3-nitroaniline instead of 4-fluoroaniline, to obtain the above-identified compound (300 mg, 67%) as a slightly yellow crystal.

MS(FAB) 376[M+1]$^+$. 1H-NMR(CDCl$_3$): δ 0.85 and 1.00 (total 3H, t, J=7.1 Hz) 4.03 and 4.08(total 2H, q, J=7.1 Hz) 7.28–7.33(1H, m) 7.54–7.72(3H, m) 8.05–8.19 (2H, m) 8.4 2–8.4 7 (1H, m)8.66–8.74 (1H, m) 11.41–11.51(1H, m).

Example 19

Synthesis of ethyl 1-(3-nitroT[]henyl)-1,4dihydro[1,8]naphthylidin-4-one-3-carboxylate The same reaction was carried out as in Example 2, except for using ethyl 3-(3-nitroanilino)-2-(2-chloronicotinoyl)acrylate, instead of ethyl 3-(4-fluoroanilino)-2-(2-chloronicotinoyl)acrylate, to obtain the above-identified compound (190 mg, 76%) as a pink crystal.

IR(KBr)cm$^{-1}$: 3067, 1727, 1625, 1607, 1531, 1479, 1424, 1251, 1268, 1211, 1124, 1094, 930, 789. MS(FAB) 340[M+1]$^+$. 1H-NMR(CDCl$_3$): δ 1.42(3H, t, J=7.1 Hz) 4.42(2H, q, J=7.1 Hz) 7.46(1H, dd, J=4.6 and 8.0 Hz) 7.76–7.83(2H, m) 8.37–8.39(1H, m) 8.40–8.45(1H, m) 8.61 (1H, dd, J=1.9 and 4.6 Hz) 13.69(1H, s) 8.84(1H, dd, J=1.9 and 7.8 Hz).

Example 20

Synthesis of 1-(3-nitrophenyl)-1,4-dihydro[1,8]naphthylidin-4-one-3-carboxylic acid The same reaction was carried out as in Example 3, except for using ethyl 1-(3-nitrophenyl)-1,4-dihydro[1,8]naphthylidin-4-one-3-carboxylate, instead of ethyl 1-(4-fluorophenyl)-1,4-dihydro[1,8]naphthylidin-4-one-3-carboxylate, to obtain the above-identified compound (98 mg, 95%) as a slightly yellow crystal.

MS(FAB) 312[M+1]$^+$. 1H-NMR(CDCl$_3$): δ 7.61(1H, dd, J=4.5 and 7.9 Hz) 7.78–7.86(2H, m) 8.37–8.40(1H, m) 8.45–8.51(1H, m) 8.77(1H, dd, J=2.0 and 4.5 Hz) 8.90(1H, dd, J=2.0 and 8.0 Hz) 9.01(1H, s) 14.04(1H, brs).

Example 21

Synthesis of ethyl 3-(N-tert-butyloxycarbonylbenzamidine-3-yl)-2-(2-chloronicotinoyl)acrylate The same reaction was carried out as in Example 1, except for using N-tert-butyloxycarbonylbenzamidine, instead of 4-fluoroaniline, to obtain the above-identified compound (1.51 g, 99%) as a yellow crystal.

IR(KBr)cm$^{-1}$: 3296, 1633, 1575, 1281, 1255, 1161. MS(FAB) 473[M+1]$^+$. 1H-NMR(CDCl$_3$): δ 0.83 and 0.98 (total 3H, t, J=7.1 Hz) 1.56(9H, s) 3.98–4.15(2H, m) 7.27–7.32(1H, m) 7.41–7.68(4H, m) 7.84–7.90(1H, m) 8.40–8.43(1H, m) 8.68–8.77(1H, m) 11.38–12.75(1H, m).

Example 22

Synthesis of ethyl 1-(N-tert-butyloxycarbonylbenzamidine-3-yl)-1,4-dihydro[1,8]naphthylidin-4-one-3-carboxylate The same reaction was carried out as in Example 2, except for using ethyl 3-(N-tert-butyloxycarbonylbenzamidine-3-yl)-2-(2-chloronicotinoyl)acrylate, instead of ethyl 3-(4-fluoroanilino)-2-(2-chloronicotinoyl)acrylate, to obtain the above-identified compound (950 mg, 71%) as a slightly orange crystal.

IR(KBr)cm$^{-1}$: 3376, 1710, 1619, 1429, 1281, 1165, 792. MS(FAB) 437[M+1]$^+$. 1H-NMR(CDCl$_3$): δ 1.40(3H, t, J=7.1 Hz) 1.54(9H, s) 4.40(2H, q, J=7.1 Hz) 7.39–7.42(1H, m) 7.61–7.69(2H, m) 7.96–8.06(2H, m) 8.58–8.60(1H, m) 8.66(1H, s) 8.81(1H, dd, J=1.9 and 7.8 Hz).

Example 23

Synthesis of 1-(N-tert-butyloxycarbonylbenzamidine-3-yl)-1,4-dihydro[1,8]naphthylidin-4-one-3-carboxylic acid The same reaction was carried out as in Example 4, except for using ethyl 1-(N-tert-butyloxycarbonylbenzamidine-3-yl)-1,4-dihydro[1,8]naphthylidin-4-one-3-carboxylate, instead of ethyl 1-(4-fluorophenyl)-1,4-dihydro[1,8]naphthylidin-4-one-3-carboxylate to obtain the above-identified compound (620 mg, 95%) as an orange crystal.

IR(KBr)cm$^{-1}$: 3067, 2976, 1732, 1622, 1472, 1160, 793. MS(FAB) 409[M+1]$^+$. 1H-NMR(CDCl$_3$): δ 1.54(9H, s) 7.55–7.71(3H, m) 8.00–8.07(2H, m) 8.75 (1H, dd, J=1.9 and 4.5 Hz) 8.88(1H, dd, J=1.9 and 8.0 Hz) 8.98(1H, s) 14.22 (1H, brs).

Example 24

Synthesis of ethyl 1-(3-acetophenyl)-1,4-dihydro[1,8]naphthylidin-4-one-3-carboxylate The same reaction was carried out as in Example 4, except for using 3-aminoacetophenone, instead of 4-fluoroaniline, to obtain the above-identified compound (670 mg, 67%) as a colorless crystal.

IR(KBr)cm$^{-1}$: 3418, 2986, 1740, 1685, 1641, 1612, 1590, 1475, 1424, 1361, 1332, 1265, 1208, 1128, 1093, 1051, 927, 790. MS(FAB) 337[M+1]$^+$. 1H-NMR(CDCl$_3$): δ 1.41(3H, t, J=7.1 Hz) 3.02(3H, s) 4.42(2H, q, J=7.1 Hz) 7.61 (1H, dd,

J=4.5 and 7.9 Hz) 7.43(1H, m) 7.65–7.73(2H, m) 8.03(1H, d, J=1.5 Hz) 8.12(1H, d, J=7.9 Hz) 8.61(1H, dd, J=1.9 and 4.5 Hz) 8.68(1H, s) 8.84(1H, dd, J=1.9 and 8.0 Hz).

Example 25

Synthesis of 1-(3-acetophenyl)-1,4-dihydro[1,8]naphthylidin-4-one-3-carboxylic acid The same reaction was carried out as in Example 3, except for using ethyl 1-(3-acetophenyl)-1,4-dihydro[1,8]naphthylidin-4-one-3-carboxylate, instead of ethyl 1-(4-fluorophenyl)-1,4-dihydro[1,8]naphthylidin-4-one-3-carboxylate, to obtain the above-identified compound (551 mg, 90%) as a colorless crystal.

IR(KBr)cm$^{-1}$: 1733, 1683, 1617, 1467, 1427, 1407, 1329, 1268, 918, 799. MS(FAB) 309[M+1]$^+$. 1H-NMR(CDCl$_3$): δ 2.67(3H, s) 7.58(1H, dd, J=4.5 and 7.9 Hz) 7.65(1H, m) 7.73(3H, t, J=4.8 Hz) 8.04(1H, s) 8.16(1H, dd, J=1.0 and 7.6 Hz) 8.77(1H, dd, J=1.9 and 3.7 Hz) 8.89(1H, dd, J=1.9 and 8.0 Hz) 9.00(1H, s) 14.20(1H, brs).

Example 26

Synthesis of ethyl 3-(2-pyridylamino)-2-(2-chloronicotinoyl)acrylate

The same reaction was carried out as in Example 1, except for using 2-aminopyridine, instead of 4-fluoroaniline, to obtain the above-identified compound (1.0 g, 91%) as a slightly yellow crystal.

IR(KBr)cm$^{-1}$: 3063, 2981, 1694, 1629, 1557. MS (FAB) 332[M+1]$^+$. 1H-NMR(CDCl$_3$): δ 0.86 and 1.07(total 3H, t, J=7.1 Hz) 4.00–4.16(2H, m) 6.98 and 7.03(total 1H, d, J=8.1 Hz) 7.09–7.21(1H, m) 7.26–7.35(1H, m) 7.57–7.64 (0.8H, m) 7.68–7.79(1.2H, m) 8.40–8.50(2H, m) 9.32(0.2H, d, J=13.3 Hz) 9.37(0.8H, d, J=13.0 Hz) 11.28–11.39(0.2H, m) 12.55–12.67(0.8H, m).

Example 27

Synthesis of ethyl 1-(2-pyridyl)-1$^4$-dihydro[1,8]naphthylidin-4-one-3-carboxylate The same reaction was carried out as in Example 2, except for using ethyl 3-(2-pyridylamino)-2-(2-chloronicotinoyl)acrylate, instead of ethyl 3-(4-fluoroanilino)-2-(2-chloronictinoyl)acrylate, to obtain the above-identified compound (0.67 g, 82%) as a slightly yellow crystal.

IR(KBr)cm$^{-1}$: 3064, 2978, 1731, 1634, 1464, 1428. MS (FAB) 296[M+1]$^+$. 1H-NMR(CDCl$_3$): δ 1.41(3H, t, J=7.1 Hz) 4.41(2H, q, J=7.1 Hz) 7.44–7.51(2H, m) 7.71–7.76(1H, m) 7.91–7.98(1H, m) 8.64(1H, dd, J=2.0 and 4.6 Hz) 8.68–8.71(1H, m) 8.83(1H, dd, J=2.0 and 7.9 Hz) 9.05(1H, s).

Example 28

Synthesis of 1-(2-pyridyl)-1,4-dihydro[1,8]naphthylidin-4-one-3-carboxylic acid

The same reaction was carried out as in Example 3, except for using ethyl 1-(2-pyridyl)-1,4-dihydro[1,8]naphthylidin-4-one-3-carboxylate, instead of ethyl 1-(4-fluorophenyl)-1,4-dihydro[1,8]naphthylidin-4-one-3-carboxylate, to obtain the above-identified compound (345 mg, 64%) as a colorless crystal.

IR(KBr)cm$^{-1}$: 3082, 1740, 1629, 1427. MS (FAB) 268 [M+1]$^+$. 1H-NMR(CDCl$_3$): δ 7.54(1H, dd, J=4.9 and 7.4 Hz) 7.59(1H, dd, J=4.5 and 8.1 Hz) 7.69–7.74(1H, m) 7.97–8.02(1H, m) 8.68–8.73(1H, m) 8.79–8.83(1H, m) 8.89–8.93(1H, m) 9.31(1H, s) 14.17(1H, brs).

Example 29

Synthesis of ethyl 3-(3-pyridylamino)-2-(2-chloronicotinoyl)acrylate

The same reaction was carried out as in Example 1, except for using 3-aminopyridine, instead of 4-fluoroaniline, to obtain the above-identified compound (210 mg, 18%) as a brown crystal.

IR(KBr)cm$^{-1}$: 3052, 2982, 1698, 1626, 1567, 1394, 1265, 1134, 814. MS(FAB) 332[M+1]$^+$. 1H-NMR(CDCl$_3$): δ 0.84 and 0.98(total 3H, t, J=7.1 Hz) 4.00–4.09(2H, m) 7.30–7.43 (2H, m) 7.60–7.69(2H, m) 8.42–8.69(4H, m) 11.31–12.69 (1H, m).

Example 30

Synthesis of ethyl 1-(3-pyridyl)-1,4-dihydro[1,8]naphthylidin-4-one-3-carboxylate The same reaction was carried out as in Example 2, except for using ethyl 3-(3-pyridylamino)-2-(2-chloronicotinoyl)acrylate, instead of ethyl 3-(4-fluoroanilino)-2-(2-chloronicotinoyl)acrylate, to obtain the above-identified compound (161 mg, 99%) as a slightly yellow crystal.

IR(KBr)cm$^{-1}$: 3046, 2926, 1728, 1626, 1609, 1479, 1428, 1209. MS(FAB) 296[M+1]$^+$. 1H-NMR(CDCl$_3$): δ 1.41(3H, t. J=7.1 Hz) 4.42(2H, q, J=7.1 Hz) 7.43–7.46(1H, m) 7.43–7.46(1H, m) 7.82–7.85(1H, m) 8.61–8.62(1H, m) 8.67 (1H, s) 8.75–8.76(1H, m) 8.79(1H, dd, J=1.3 and 4.8 Hz) 8.83(1H, dd, J=1.9 and 8.0 Hz).

Example 31

Synthesis of 1-(3-pyridyl)-1,4-dihydro[1,8]naphthylidin-4-one-3-carboxylic acid

The same reaction was carried out as in Example 3, except for using ethyl 1-(3-pyridyl)-1,4-dihydro[1,8]naphthylidin-4-one-3-carboxylate, instead of ethyl 1-(4-fluorophenyl)-1,4-dihydro[1,8]naphthylidin-4-one-3-carboxylate, to obtain the above-identified compound (110 mg, 99%) as a colorless crystal.

IR(KBr)cm$^{-1}$: 3054, 1732, 1621, 1456, 1425, 1321, 792. MS(FAB) 268[M+1]$^+$. 1H-NMR(CDCl$_3$): δ 7.57–7.62(2H, m) 7.81–7.84(1H, m) 8.76–8.78(2H, m) 8.83–8.85(1H, m) 8.89(1H, dd, J=1.9 and 8.0 Hz) 8.99(1H, s) 14.12(1H, brs).

Example 32

Synthesis of ethyl 3-(4-pyridylamino)-2-(2-chloronicotinoyl)acrylate

The same reaction was carried out as in Example 1, except for using 4-aminopyridine, instead of 4-fluoroaniline, to obtain the above-identified compound (1.09 g, 94%) as a slightly yellow crystal.

MS(FAB) 307[M+1]$^+$. 1H-NMR(CDCl$_3$): δ 0.85 and 0.97 (total 3H, t, J=7.1 Hz) 4.03 and 4.07(total 2H, q. J=7.1 Hz) 7.12 and 7.17(total 2H, d, J=6.3 Hz) 7.31(1H, m) 7.61 and 7.69(total 1H, dd, J=1.8 and 7.5 Hz) 8.44(1H, dd, J=1.9 and 4.8 Hz) 8.60 and 8.63(1H, total 1H, d, J=6.1 Hz) 8.68 and 8.72(total 1H, d, J=2.7 Hz) 12.40(1H, m).

Example 33

Synthesis of ethyl 1-(4-pyridyl)-1,4-dihydro[1,8]naphthylidin-4-one-3-carboxylate The same reaction was carried out as in Example 2, except for using ethyl 3-(4-pyridylamino)-2-(2-chloronicotinoyl)acrylate, instead of ethyl 3-(4-fluoroanilino)-2-(2-chloronicotinoyl)acrylate, to obtain the above-identified compound (610 mg, 63%) as a pink crystal.

IR(KBr)cm⁻¹: 3062, 1728, 1634, 1593, 1435, 1422, 1337, 1217, 1130, 1093, 1047, 788. MS(FAB) 296[M+1]⁺. 1H-NMR(CDCl₃): δ 1.41(3H, t, J=7.1 Hz) 4.42(2H, q, J=7.1 Hz) 7.46(2H, m) 7.76–7.83(2H, m) 8.63(1H, dd, J=2.0 and 6.5 Hz) 8.67(1H, s) 8.83(1H, dd, J=1.9 and 6.1 Hz) 8.87(2H, d, J=6.1 Hz).

Example 34

Synthesis of 1-(4-pyridyl)-1,4-dihydro[1,8]naphthylidin-4-one-3-carboxylic acid

The same reaction was carried out as in Example 3, except for using ethyl 1-(4-pyridyl)-1,4-dihydro[1,8]naphthylidin-4-one-3-carboxylate, instead of ethyl 1-(4-fluorophenyl)-1,4-dihydro[1,8]naphthylidin-4-one-3-carboxylate, to obtain the above-identified compound (460 mg, 83%) as a slightly yellow crystal.

IR(KBr)cm⁻¹: 3045, 1740, 1630, 1582, 1548, 1473, 1416, 1358, 1310, 1250, 790. MS(FAB) 268[M+1]⁺. 1H-NMR (CDCl₃): δ 7.45(2H, dd, J=1.6 and 4.5 Hz) 7.62(1H, m) 8.78(1H, dd, J=1.9 and 4.5 Hz) 8.82(1H, d, J=7.88 Hz) 8.90(2H, m) 8.90(1H, dd, J=2.0 and 8.0 Hz) 8.98(1H, s) 14.06(1H, brs).

Example 35

Synthesis of ethyl 3-(2-tert-butyloxycarbonylaminopyridine-5-yl)-2-(2-chloronicotinoyl)acrylate The same reaction was carried out as in Example 1, except for using 5-amino-2-tert-butyloxycarbonylaminopyridine, instead of 4-fluoroaniline, to obtain the above-identified compound (1.47 g, 83%) as a slightly yellow crystal.

IR(KBr)cm⁻¹: 3201, 2979, 1732, 1536, 1387, 1293, 1155. MS(FAB) 447[M+1]⁺. 1H-NMR(CDCl₃): δ 0.83 and 0.97 (total 3H, t, J=7.1 Hz) 1.52(9H, s) 4.00 and 4.02(total 2H, q. J=7.1 Hz) 7.21–7.31(2H, m) 7.58–7.66(2H, m) 8.03–8.05 (1H, m) 8.19–8.20(1H, m) 8.41(1H, dd, J=1.9 and 4.8 Hz) 8.54–8.63(1H, m) 11.30–11.31(1H, m).

Example 36

Synthesis of ethyl 1-(2-tert-butyloxycarbonylaminopyridine-5-yl)-1,4-dihydro[1,8]naphthylidin-4-one-3-carboxylate The same reaction was carried out as in Example 2, except for using ethyl 3-(2-tert-butyloxycarbonylaminopyridin-5-yl)-2-(2-chloronicotinoyl)acrylate, instead of ethyl-3-(4-fluoroanilino)-2-(2-chloronicotinoyl)acrylate, to obtain the above-identified compound (1.33 g, quantitative) as a slightly yellow crystal.

IR(KBr)cm⁻¹: 2980, 1732, 1648, 1530, 1427, 1255, 1156, 1056, 789. MS(FAB) 411[M+1]⁺. 1H-NMR(CDCl₃): δ 1.41 (3H, t, J=7.1 Hz) 1.59(9H, s) 4.41(2H, q, J=7.1 Hz) 7.41–7.44(1H, m) 7.54(1H, brs) 7.76(1H, dd, J=2.6 and 8.9 Hz) 8.17–8.20(1H, m) 8.31–8.33(1H, m) 8.62(1H, dd, J=1.9 and 4.5 Hz) 8.65(1H, s) 8.82(1H, dd, J=1.9 and 7.9 Hz).

Example 37

Synthesis of 1-(2-tert-butyloxycarbonylaminopyridin-5-yl)-14-dihydro[1,8]naphthylidin-4-one-3-carboxylic acid The same reaction was carried out as in Example 3, except for using ethyl 1-(2-tert-butyloxycarbonylaminopyridin-5-yl)-1,4-dihydro[1,8]naphthylidin-4-one-3-carboxylate, instead of ethyl 1-(4-fluorophenyl)-1,4-dihydro[1,8]naphthylidin-4-one-3-carboxylate, to obtain the above-identified compound (890 mg, 87%) as a yellow crystal.

IR(KBr)cm⁻¹: 3265, 1725, 1619, 1530, 1468, 1158, 794. MS(FAB) 383[M+1]⁺. 1H-NMR(CDCl₃): δ 1.52(9H, s) 7.57–7.64(2H, m) 7.76(1H, dd, J=2.6 and 9.0 Hz) 8.20–8.23 (1H, m) 8.32–8.33(1H, m) 8.76–8.78(1H, m) 8.88(1H, dd, J=1.8 and 8.0 Hz) 8.98(1H, s) 14.20(1H, brs).

Example 38

Synthesis of ethyl 3-(2-benzyloxypyridin-5-ylamino)-2-(2-chloronicotinoyl)acrylate The same reaction was carried out as in Example 1, except for using 5-amino-2-benzyloxypyridine, instead of 4-fluoroaniline, to obtain the above-identified compound (1.81 g, 94%) as a slightly yellow crystal.

IR(KBr)cm⁻¹: 3066, 1691, 1618, 1493, 1394, 1264. MS(FAB) 438[M+1]⁺. 1H-NMR(CDCl₃): δ 0.97(3H, t, J=7.1 Hz) 4.04(2H, Q, J=7.1 Hz) 5.41(2H, s) 6.87–6.91(1H, m) 7.27–7.52(6H, m) 7.54–7.67(2H, m) 8.12–8.18(1H, m) 8.41(1H, dd, J=2.0 and 4.7 Hz) 8.52–8.60(1H, m) 11.27–12.73(1H, m).

Example 39

Synthesis of ethyl 1-(2-benzyloxypyridin-5-ylamino)-1,4-dihydro[1,8]naphthylidin-4-one-3-carboxylate The same reaction was carried out as in Example 2, except for using ethyl 3-(2-benzyloxypyridin-5-ylamino)-2-(2-chloronicotinoyl)acrylate, instead of ethyl 3-(4-fluoroanilino)-2-(2-chloronicotinoyl)acrylate, to obtain the above-identified compound (1.34 g, 86%) as a slightly yellow crystal.

IR(KBr)cm⁻¹: 2982, 1695, 1646, 1428, 1251, 790. MS(FAB) 402[M+1]⁺. 1H-NMR(CDCl₃): δ 1.41(3H, t, J=7.1 Hz) 4.41(2H, q, J=7.1 Hz) 5.47(2H, s) 6.98–7.00(1H, m) 7.35–7.50(6H, m) 7.67–7.70(1H, m) 8.25–8.26(1H, m) 8.63(1H, dd, J=1.9 and 4.5 Hz) 8.66(1H, s) 8.83(1H, dd, J=1.9 and 7.8 Hz).

Example 40

Synthesis of 1-(2-benzyloxypyridin-5-ylamino)-1,4-dihydro[1,8]naphthylidin-4-one-3-carboxylic acid The same reaction was carried out as in Example 3, except for using ethyl 1-(2-benzyloxypyridin-5-ylamino)-1,4-dihydro[1,8]naphthylidin-4-one-3-carboxylate, instead of ethyl 1-(4-fluorophenyl)-1,4-dihydro[1,8]naphthylidin-4-one-3-carboxylate, to obtain the above-identified compound (794 mg, 95%) as a colorless crystal.

IR(KBr)cm⁻¹: 3069, 1739, 1621, 1477, 1123, 790. MS(FAB) 374[M+1]⁺. 1H-NMR(CDCl₃): δ 5.48(2H, s) 6.99–7.02(1H, m) 7.33–7.44(3H, m) 7.48–7.51(2H, m) 7.56–7.60(1H, m) 7.66–7.69(1H, m) 8.25–8.27(1H, m) 8.79 (1H, dd, J=1.9 and 4.5 Hz) 8.88(1H, dd, J=1.9 and 8.1 Hz) 8.98(1H, s) 14.20(1H, brs).

Example 41

Synthesis of ethyl 1-(isoquinolin-1-yl)-1,4-dihydro[1,8]naphthylidin-4-one-3-carboxylate The same reaction was carried out as in Example 4, except for using 1-aminoisoquinoline, instead of 4-fluoroaniline, to obtain the above-identified compound (660 mg, 63%) as a yellow crystal.

IR(KBr)cm⁻¹: 3461, 3060, 2976, 1690, 1648, 1608, 1552, 1498, 1478, 1429, 1383, 1351, 1324, 1275, 1245, 1221, 1148, 1098, 1049, 1021, 838, 792. MS(FAB) 346[M+1]⁺. 1H-NMR(CDCl₃): δ 1.22(3H, t, J=7.0 Hz) 4.39(2H, q, J=7.0 Hz) 7.39(1H, m) 7.47(1H, m) 7.80 (1H, m) 7.94(1H, d, J=8.1

Hz) 8.03(1H, m) 8.44(1H, m) 8.59(1H, d, J=5.6 Hz) 8.79 (1H, s) 8.87(1H, dd, J=1.9 and 8.0 Hz).

Example 42

Synthesis of 1-(isoquinolin-1-yl)-1,4-dihydro[1,8] naphthylidin-4-one-3-carboxylic acid The same reaction was carried out as in Example 3, except for using ethyl 1-(isoquinolin-1-yl)-1,4-dihydro[1,8] naphthylidin-4-one-3-carboxylate, instead of ethyl 1-(4-fluorophenyl)-1,4-dihydro[1,8]naphthylidin-4 -one-3-carboxylate, to obtain the above-identified compound (376 mg, 68%) as a yellow crystal.

IR(KBr)cm$^{-1}$: 3418, 2920, 1734, 1612, 1548, 1456, 1430, 1343, 1308, 1274, 788. MS(FAB) 318[M+1]$^+$. 1H-NMR (CDCl$_3$): δ 7.36(1H, d, J=8.7 Hz) 7.52(1H, m) 7.58(1H, m) 7.82(1H, t, J=7.2 Hz) 7.97(1H, d, J=5.8 Hz) 8.05(1H, d, J=8.5 Hz) 8.61(2H, m) 8.90(1H, m) 9.08(1H, s) 14.21(1H, s).

Example 43

Synthesis of ethyl 1-(quinolin-8-yl)-1,4-dihydro[1,8] naphthylidin-4-one-3-carboxylate The same reaction was carried out as in Example 4, except for using 8-aminoquinoline, instead of 4-fluoroaniline, to obtain the above-identified compound (660 mg, 63%) as a yellow crystal.

IR(KBr)cm$^{-1}$: 3462, 2978, 1695, 1630, 1560, 1504, 1477, 1446, 1429, 1391, 1298, 1263, 1130, 1078, 985, 822, 795, 752. MS(FAB) 346[M+1]$^+$. 1H-NMR(CDCl$_3$): δ 0.99(3H, t, J=7.1 Hz) 4.08(2H, q, J=7.1 Hz) 7.31(1H, m) 7.53(1H, m) 7.63(1H, m) 7.70(1H, m) 7.75(1H, m) 8.21(1H, d, J=8.2 Hz) 8.41(1H, dd, J=1.8 and 4.6 Hz) 8.94(1H, S) 8.98(1H, m) 9.02(1H, m) 13.92(1H, d, J=14 Hz).

Example 44

Synthesis of 1-(quinolin-8-yl)-1,4-dihydro[1,8] naphthylidin-4-one-3-carboxylic acid The same reaction was carried out as in Example 3, except for using ethyl 1-(quinolin-8-yl)-1,4-dihydro[1,8] naphthylidin-4-one-3-carboxylate, instead of ethyl 1-(4-fluorophenyl)-1,4-dihydro[1,8]naphthylidin-4-one-3-carboxylate, to obtain the above-identified compound (381 mg, 66%) as a yellow crystal.

IR(KBr)cm$^{-1}$: 3418, 2924, 1716, 1619, 1570, 1504, 1471, 1430, 1392, 1302, 1263, 1077, 984, 822, 790, 755. MS(FAB) 318[M+1]$^+$. 1H-NMR(CDCl$_3$): δ 7.33(1H, m) 7.50(1H, m) 7.58(1H, m) 7.62(1H, m) 7.86(1H, m) 8.10(1H, dd, J=1.2 and 8.4 Hz) 8.25(1H, dd, J=1.2 and 8.4 Hz) 8.58(1H, m) 8.62(1H, dd, J=1.8 and 4.2 Hz) 8.77(1H, dd, J=1.8 and 4.2 Hz) 8.90(1H, dd, J=1.8 and 7.8 Hz) 8.97(1H, s) 14.43(1H, s).

Example 45

Synthesis of ethyl 3-(2-tert-butyloxycarbonylaminopyrimidin-5-yl)-2-(2-chloronicotinoyl)acrylate The same reaction was carried out as in Example 1, except for using 2-(tert-butyloxycarbonyl)-5-aminopyrimidine, instead of 4-fluoroaniline, to obtain the above-identified compound (850 mg, 54%) as a slightly yellow crystal.

IR(KBr)cm$^{-1}$: 3231, 2984, 1754, 1704, 1626, 1574, 1392, 1230, 1144. MS (FAB) 448[M+1]$^+$. 1H-NMR(CDCl$_3$): δ 0.98(3H, t, J=7.1 Hz) 1.56(9H, s) 4.05(2H, q, J=7.1 Hz) 7.29–7.33(1H, m) 7.49–7.52(1H, m) 7.60(1H, dd, J=1.8 and 7.5 Hz) 8.42–8.44(1H, m) 8.47–8.51 (1N, m) 8.59 (2H, s) 12.57–12.60(1H, s).

Example 46

Synthesis of ethyl 1-(2-tert-butyloxycarbonylaminopyrimidin-5-yl)-1,4-dihydro[1,8] naphthylidin-4-one-3-carboxylate The same reaction was carried out as in Example 2, except for using ethyl 3-(2-tert-butyloxycarbonylaminopyrimidin-5-yl)-2-(2-chloronicotinoyl)acrylate, instead of ethyl 3-(4-fluoroanilino)-2-(2-chloronicotinoyl)acrylate, to obtain the above-identified compound (830 mg, quantitative) as a slightly yellow crystal.

IR(KBr)cm$^{-1}$: 3232, 1736, 1625, 1508, 1444, 1265, 1145, 790. MS(FAB) 412[M+1]$^+$. 1H-NMR(CDCl$_3$) 61.41(3H, t, J=7.1 Hz) 1.58(9H, s) 4.01(2H, q, J=7.1 Hz) 7.44–7.47(1H, m) 7.65(1H, brs) 8.59–8.62(2H, m) 8.70(2H, s) 8.82(1H, dd, J=1.9 and 8.0 Hz).

Example 47

Synthesis of 1-(2-tert-butyloxycarbonylaminopyrimidin-5-yl)-1,4-dihydro[1,8]naphthylidin-4-one-3-carboxylic acid The same reaction was carried out as in Example 3, except for using ethyl 1-(2-tert-butyloxycarbonylaminopyrimidin-5-yl)-1,4-dihydro[1,8]naphthylidin-4-one-3-carboxylate, instead of ethyl 1-(4-fluorophenyl)-1,4-dihydro[1,8] naphthylidin-4-one-3-carboxylate, to obtain the above-identified compound (170 mg, 91%) as a slightly yellow crystal.

IR(KBr)cm$^{-1}$: 3312, 1732, 1619, 1511, 1442, 1144, 794. MS(FAB) 384[M+1]$^+$. 1H-NMR(CDCl$_3$): δ 1.55(9H, s) 7.59–7.63(1H, m) 7.71(1H, brs) 8.70(2H, s) 8.76(1H, dd, J=2.0 and 4.5 Hz) 8.88(1H, dd, J=2.0 and 8.1 Hz) 8.95(1H, s) 14.03(11, brs).

Example 48

Synthesis of ethyl 3-(2-thiazolyl)-2-(2-chloronicotinoyl)acrylate

The same reaction was carried out as in Example 1, except for using 2-aminothiazol, instead of 4-fluoroaniline, to obtain the above-identified compound (1.06 g, 95%) as a brown oily product.

IR(neat)cm$^{-1}$: 2928, 1698, 1626, 1574, 1395, 1257. MS(FAB) 338[M+1]$^+$. 1H-NMR(CDCl$_3$): δ 0.86 and 1.06 (total 3H, t, J=7.1 Hz) 4.05 and 4.09(total 2H, q, J=7.1 Hz) 7.01 and 7.06(total 1H, d, J=3.5 Hz) 7.29–7.33(1H, m) 7.47 and 7.52(total 1H, d, J=3.5 Hz) 7.60–7.72(1H, m) 8.42–8.44 (1H, m) 8.78–8.93(1H, m) 11.58–12.84(1H, m).

Example 49

Synthesis of ethyl 1-(2-thiazolyl)-1,4-dihydro[1,8] naphthylidin-4-one-3-carboxylate The same reaction was carried out as in Example 2, except for using ethyl 3-(2-thiazolyl)-2-(2-chloronicotinoyl) acrylate, instead of ethyl 3-(4-fluoroanilino)-2-(2-chloronicotinoyl)acrylate, to obtain the above-identified compound (310 mg, 37%) as a slightly yellow crystal.

IR(KBr)cm$^{-1}$: 3083, 1740, 1642, 1438, 1361, 1247, 1216, 789. MS(FAB) 302[M+1]$^+$. 1H-NMR(CDCl$_3$): δ 1.44(3H, t, J=7.1 Hz) 4.45(2H, q, J=7.1 Hz) 7.34(1H, d, J=3.5 Hz) 7.53–7.56(1H, m) 7.74(1H, d, J=3.5 Hz) 8.83–8.87(2H, m) 10.05(1H, s).

Example 50

Synthesis of 1–2-thiazolyl-1,4-dihydro[1,8]naphthylidin-4-one-3-carboxylic acid

The same reaction was carried out as in Example 3, except for using ethyl 1-(2-thiazolyl)-1,4-dihydro[1,8]naphthylidin-4-one-3-carboxylate, instead of ethyl 1-(4-fluorophenyl)-1,4-dihydro[1,8]naphthylidin-4-one-3-carboxylate, to obtain the above-identified compound (91 mg, 40%) as a slightly yellow crystal.

IR(KBr)cm$^{-1}$: 1736, 1611, 1460, 1326, 1234. MS(FAB) 274[M+1]$^+$. 1H-NMR (CDCl$_3$): δ 7.44(1H, d, J=3.5 Hz) 7.67–7.71(1H, m) 7.78(1H, d, J=3.5 Hz) 8.92(1H, dd, J=1.9 and 8.0 Hz) 8.99(1H, dd, J=1.8 and 4.5 Hz) 10.35(1H, s) 13.84(1H, brs).

Example 51

Synthesis of 1-(4-fluorophenyl)-1,4-dihydro[1,8]naphthylidin-4-one-3-carboxamide Thionyl chloride (13.3 μl, 0.18 mmol) was added to a tetrahydrofuran (1 ml) solution of 1-(4-fluorophenyl)-1,4-dihydro[1,8]naphthylidin-4-one-3-carboxylic acid (26 mg, 0.09 mmol) at room temperature and the solution was stirred at 75° C. for 1 hour. The solvent was distilled off under vacuum, whereby a colorless crystal as an acid chloride was obtained. Next, ammonium hydroxide (28% aqueous solution, 27.8 μl, 0.46 mmol) was added to a tetrahydrofuran (1.5 ml) solution of this acid chloride at room temperature and the solution was stirred at that temperature for 20 minutes. Next, the reaction solution was diluted with ethyl acetate (20 ml) and successively washed with water (5 ml) and saturated saline (5 ml), then dried over anhydrous sodium sulfate, then the solvent was distilled off under vacuum. The precipitated crystal was washed with diisopropyl ether, then the crystal was obtained by filtration to obtain the above-identified compound (14 mg, 54%) as a slightly brown crystal.

IR(KBr)cm$^{-1}$: 3337, 3074, 1676, 1508. MS(FAB) 284 [M+1]$^+$. 1H-NMR(CDCl$_3$): δ 5.80(1H, brs) 7.23–7.32(2H, m) 7.39–7.52(3H, m) 8.71(1H, dd, J=2.0 and 4.6 Hz) 8.84(1H, dd, J=2.0 and 7.9 Hz) 9.00(1H, s) 9.50(1H, brs).

Example 52

Synthesis of 1-(4-fluorophenyl)-N-methyl-1,4-dihydro[1,8]naphthylidin-4-one-3-carboxamide 40% methylamine ethanol solution (4 ml) was added to ethyl 1-(4-fluorophenyl)-1,4-dihydro[1,8]naphthylidin-4-one-3-carboxylate (31 mg, 0.10 mmol) at room temperature and the solution was allowed to stand overnight. The precipitated crystal was obtained by filtration and washed with ethanol to obtain the above-identified compound (26 mg, 87%) as a colorless crystal.

IR(KBr)cm$^{-1}$: 1708, 1671, 1601, 1578, 1508, 1485, 1429, 1247, 1084, 781. MS(FAB) 298[M+1]$^+$. 1H-NMR(CDCl$_3$): δ 3.03(3H, d, J=5.0 Hz) 7.24–7.31(2H, m) 7.39–7.52(3H, m) 8.69(1H, dd, J=2.0 and 4.6 Hz) *8.83(1H, dd, J=2.0 and 8.0 Hz) 8.99(1H, s) 9.66(1H, brs).

Example 53

Synthesis of 1-(4-fluorophenyl)-N-isopropyl-1,4-dihydro[1,8]naphthylidin-4-one-3-carboxamide Thionyl chloride (14.6 μl, 0.20 mmol) was added to a tetrahydrofuran (1 ml) solution of 1-(4-fluorophenyl)-1,4-dihydro[1,8]naphthylidin-4-one-3-carboxylic acid (30 mg, 0.10 mmol) at room temperature and the solution was stirred at 75° C. for 1 hour. The solvent was distilled off under vacuum to obtain a colorless crystal as an acid chloride. Next, isopropylamine (19 μl, 0.22 mmol) and triethylamine (55 μl, 0.40 mmol) were added to a dichloromethane (2 ml) solution of this acid chloride at room temperature and the solution was stirred at that temperature overnight. Next, the reaction solution was successively washed with water (5 ml) and saturated saline (5 ml), then dried over anhydrous sodium sulfate, then the solvent was distilled off under vacuum. The precipitated crystal was washed by diethyl ether, then the crystal was obtained by filtration to obtain the above-identified compound (29 mg, 42%) as a colorless crystal.

IR(KBr)cm$^{-1}$: 3251, 2983, 2965, 1668, 1608, 1547, 1508, 1482, 1432, 1210, 790. MS(FAB) 326[M+1]$^+$. 1H-NMR (CDCl$_3$): δ 1.30(6H, d, J=6.6 Hz) 7.24–7.28(2H, m) 7.41–7.52(3H, m) 8.69(1H, m) 8.82(1H, dd, J=1.8 and 7.8 Hz) 8.98(1H, s) 9.63(1H, brs).

Example 54

Synthesis of N-allyl-1-(4-fluorophenyl)-1,4-dihydro[1,8]naphthylidin-4-one-3-carboxamide The same reaction was carried out as in Example 53, except for using allylamine, instead of isopropylamine, to obtain the above-identified compound (36 mg, 55%) as a colorless crystal.

IR(KBr)cm$^{-1}$: 3248, 3080, 3049, 1668, 1603, 1547, 1508, 1481, 1427, 1216, 794. MS(FAB) 324[M+1]$^+$. 1H-NMR (CDCl$_3$): δ 4.13(2H, m) 5.17(1H, dd, J=1.3 and 10.2 Hz) 5.30(1H, d, J=17 Hz) 5.97(1H, m) 7.25–7.29(2H, m) 7.40–7.49(3H, m) 8.70(1H, d, J=4.5 Hz) 8.84(1H, dd, J=1.8 and 7.9 Hz) 8.99(1H, s) 9.87(1H, brs).

Example 55

Synthesis of 1-(4-fluorophenyl)-N-isobutyl-1,4-dihydro[1,8]naphthylidin-4-one-3-carboxamide The same reaction was carried out as in Example 53, except for using isobutylamine, instead of isopropylamine, to obtain the above-identified compound (29 mg, 57%) as a colorless crystal.

IR(KBr)cm$^{-1}$: 3234, 3043, 2959, 1664, 1603, 1551, 1508, 1480, 1426, 1347, 1321, 1250, 1214, 1156, 859, 794, 731. MS(FAB) 340[M+1]$^+$. 1H-NMR(CDCl$_3$): δ 1.02(6H, d, J=6.7 Hz) 1.94(1H, m) 3.33(2H, q, J=6.7 Hz) 7.26(2H, m) 7.40–7.48(3H, m) 8.69(1H, dd, J=1.8 and 4.4 Hz) 8.84(1H, dd, J=1.8 and 7.9 Hz) 8.99(1H, s) 9.82(1H, brs).

Example 56

Synthesis of N-cyclopropylmethyl-1-(4-fluorophenyl)-1,4-dihydro[1,8]naphthylidin-4-one-3-carboxamide The same reaction was carried out as in Example 53, except for using aminomethylcyclopropane, instead of isopropylamine, to obtain the above-identified compound (35 mg, 69%) as a colorless crystal.

IR(KBr)cm$^{-1}$: 3480, 3044, 1662, 1602, 1547, 1508, 1480, 1426, 1332, 1216, 1154, 854, 793. MS(FAB) 340[M+1]$^+$. 1H-NMR(CDCl$_3$): δ 0.31(2H, dd, J=4.8 and 10.4 Hz) 0.56 (2H, m) 1.12(1H, m) 3.36(2H, m) 7.24(2H, m) 7.40–7.48 (3H, m) 8.69(1H, dd, J=2.0 and 4.5 Hz) 8.84(1H, dd, J=1.9 and 8.0 Hz) 8.99 (1H, s) 9.83(1H, brs).

Example 57

Synthesis of N-cyclohexyl-1-(4-fluorophenyl)-1,4-dihydro[1,8]naphthylidin-4-one-3-carboxamide The same reaction was carried out as in Example 53, except for using aminocyclohexane, instead of isopropylamine, to obtain the above-identified compound (33 mg, 66%) as a colorless crystal.

IR(KBr)cm$^{-1}$: 3267, 3066, 2925, 2855, 1680, 1605, 1539, 1509, 1487, 1434, 1223, 1160, 845, 786. MS(FAB) 366[M+1]$^+$. 1H-NMR(CDCl$_3$): δ 1.25–1.63(6H, m) 1.77(2H, m) 2.02(1H, m) 4.03(2H, m) 7.39–7.52(3H, m) 8.69(1H, dd, J=1.9 and 4.5 Hz) 8.82(1H, dd, J=1.9 and 8.0 Hz) 8.98(1H, s) 9.74(1H, d, J=7.4 Hz).

Example 58

Synthesis of 1-(4-fluorophenyl)-N-(2-hydroxyethyl)-1,4-dihydro[1,8]naphthylidin-4-one-3-carboxamide The same reaction was carried out as in Example 53, except for using aminoethanol, instead of isopropylamine, to obtain the above-identified compound (77 mg, 67%) as a colorless crystal.

IR(KBr)cm$^{-1}$: 3356, 3084, 1665, 1549, 1508, 1483. MS (FAB) 328[M+1]$^+$. 1H-NMR(CDCl$_3$): δ 3.11–3.16(1H, m) 3.62–3.68(2H, m) 3.81–3.87(2H, m) 7.23–7.30(2H, m) 7.39–7.52(3H, m) 8.70(1H, dd, J=1.9 and 4.5 Hz) 8.84(1H, dd, J=1.9 and 8.0 Hz) 8.99(1H, s) 10.08–10.17(1H, m).

Example 59

Synthesis of 1-(4-fluorophenyl)-N-(2-methoxyethyl)-1,4-dihydro[1,8]naphthylidin-4-one-3-carboxamide The same reaction was carried out as in Example 53, except for using methoxyethylamine, instead of isopropylamine, to obtain the above-identified compound (91 mg, 76%) as a colorless crystal.

IR(KBr)cm$^{-1}$: 3237, 3089, 1667, 1602, 1508, 1430. MS (FAB) 342[M+1]$^+$. 1H-NMR(CDCl$_3$): δ 3.43(3H, s) 3.60 (2H, t, J=5.3 Hz) 3.67–3.73(2H, m) 7.24–7.29(2H, m) 7.39–7.48(3H, m) 8.68(1H, dd, J=1.8 and 4.5 Hz) 8.84(1H, dd, J=1.8 and 8.0 Hz) 8.98(1H, s) 9.88–9.96(1H, m).

Example 60

Synthesis of N-(2,2-dimethylaminoethyl)-1-(4-fluorophenyl)-1,4-dihydro[1,8]naphthylidin-4-one-3-carboxamide The same reaction was carried out as in Example 53, except for using dimethylaminoethylamine, instead of isopropylamine, to obtain the above-identified compound (57 mg, 46%) as a colorless crystal.

IR(KBr)cm$^{-1}$: 3226, 2768, 1660, 1602, 1508, 1426. MS (FAB) 355[M+1]$^+$. 1H-NMR(CDCl$_3$): δ 2.30–2.33(6H, m) 2.56(2H, t, J=6.5 Hz) 3.57–3.66(2H, m) 7.24–7.29(2H, m) 7.39–7.47(3H, m) 8.68(1H, dd, J=1.9 and 4.4 Hz) 8.84(1H, dd, J=1.9 and 8.0 Hz) 8.98(1H, s) 9.82–9.89(1H, m).

Example 61

Synthesis of N-benzyl-1-(4-fluorophenyl)-1,4-dihydro[1,8]naphthylidin-4-one-3-carboxamide The same reaction was carried out as in Example 53, except for using benzylamine, instead of isopropylamine, to obtain the above-identified compound (58 mg, 77%) as a colorless crystal.

IR(KBr)cm$^{-1}$: 3246, 3084, 1602, 1535, 1508, 1218, 792, 698. MS(FAB) 374[M+1]$^+$. 1H-NMR(CDCl$_3$): δ 4.70(2H, d, J=5.8 Hz) 7.20–7.50(10H, m) 8.69(1H, dd, J=1.9 and 4.5 Hz) 8.81(1H, dd, J=1.9 and 8.0 Hz) 9.02(1H, s) 10.14(1H, brs).

Example 62

Synthesis of 1-(4-fluorophenyl)-N-(2-pyridyl)methyl-1,4-dihydro[1,8]naphthylidin-4-one-3-carboxamide The same reaction was carried out as in Example 53, except for using 2-aminomethylpyridine, instead of isopropylamine, to obtain the above-identified compound (44 mg, 78%) as a colorless crystal.

IR(KBr)cm$^{-1}$: 1660, 1601, 1540, 1508, 1479, 1426, 1324, 1220, 848, 790, 750. MS (FAB) 375[M+1]$^+$. 1H-NMR (CDCl$_3$): δ 4.85(2H, d, J=7.6 Hz) 7.18(1H, m) 7.35(1H, d, J=7.9 Hz) 7.40–7.48(3H, m) 7.65(1H, dt, J=1.7 and 7.6 Hz) 8.63(1H, d, J=4.3 Hz) 8.69(1H, dd, J=1.8 and 4.5 Hz) 8.86(1H, dd, J=1.8 and 7.8 Hz) 9.02(1H, s) 10.47(1H, brs).

Example 63

Synthesis of 1-(4-fluorophenyl)-N-(3-pyridyl)methyl-1,4-dihydro[1,8]naphthylidin-4-one-3-carboxamide The same reaction was carried out as in Example 53, except for using 3-aminomethylpyridine, instead of isopropylamine, to obtain the above-identified compound (46 mg, 82%) as a colorless crystal.

IR(KBr)cm$^{-1}$: 3270, 3063, 1655, 1603, 1545, 1508, 1479, 1422, 1323, 1294, 1220, 864, 852, 782, 754, 732. MS (FAB) 375[M+1]$^+$. 1H-NMR(CDCl$_3$): δ 4.70(2H, d, J=6.0 Hz) 7.41–7.43(2H, m) 7.48(1H, m) 7.72(1H, d, J=7.8 Hz) 8.52 (1H, d, J=3.88 Hz) 8.65(1H, s) 8.70(1H, dd, J=1.9 and 4.5 Hz) 8.82(1H, dd, J=1.9 and 7.8 Hz) 9.01(1H, s) 10.22(1H, brs).

Example 64

Synthesis of 1-(4-fluorophenyl)-N-(4-pyridyl)methyl-1,4-dihydro[1,8]naphthylidin-4-one-3-carboxamide The same reaction was carried out as in Example 53, except for using 4-aminomethylpyridine, instead of isopropylamine, to obtain the above-identified compound (35 mg, 62%) as a colorless crystal.

IR(KBr)cm$^{-1}$: 3458, 3233, 1668, 1612, 1583, 1543, 1504, 1482, 1429, 1415, 1348, 1296, 1217, 1151, 1096, 843, 789, 712. MS (FAB) 375[M+1]$^+$. 1H-NMR(CDCl$_3$): δ 4.71(2H, d, J=6.0 Hz) 7.29(2H, m) 7.40–7.44(2H, m) 7.49(1H, dd, J=4.5 and 8.0 Hz) 8.56(2H, d, J=5.9 Hz) 8.72(1H, dd, J=1.8 and 4.5 Hz) 8.84(1H, dd, J=1.8 and 9.7 Hz) 9.01(1H, s) 10.29(1H, brs).

Example 65

Synthesis of 1-(4-fluorophenyl)-N-(2-phenylethyl)-1,4-dihydro[1,8]naphthylidin-4-one-3-carboxamide The same reaction was carried out as in Example 53, except for using β-phenethylamine, instead of isopropylamine, to obtain the above-identified compound (42 mg, 72%) as a slightly yellow crystal.

IR(KBr) cm$^{-1}$: 3459, 3234, 1672, 1612, 1544, 1505, 1482, 1429, 1416, 1220, 843, 787. MS (FAB) 388[M+1]$^+$. 1H-NMR(CDCl$_3$): δ 2.97(2H, t, J=7.3 Hz) 3.74(2H, q, J=7.3 Hz) 7.22–7.32(6H, m) 7.40–7.47(3H, m) 8.69(1H, dd, J=1.9 and 4.55 Hz) 8.82(1H, dd, J=1.9 and 7.8 Hz) 8.98(1H, s) 9.82 (1H, brs).

Example 66

Synthesis of 1-(4-fluorophenyl)-N-(4-phenylpiperazyl)-1,4-dihydro[1,8]naphthylidin-4-one-3-carboxamide To a methylene chloride (3 ml) solution of 1-(4-fluorophenyl)-1,4-dihydro[1,8]naphthylidin-4-one-3-carboxylic acid (42 mg, 0.15 mmol), benzotriazol-1-yloxytris(dimethylamino)phosphonium hexafluorophosphate (72 mg, 0.165. mmol), 1-hydroxybenzotriazole (24 mg, 0.15 mmol), triethylamine (42 µl, 0.30 mmol), and 4-phenylpiperazine (25 µl, 0.165 mmol) were added at room temperature, followed by stirring at the same temperature overnight. Then, the reaction mixture was successively washed with water (10 ml), saturated aqueous sodium hydrogen carboxylate solution (10 ml), saturated saline water (10 ml) and, then, dried over anhydrous sodium sulfate and the solvent was distilled off under vacuum. The residue was purified by a silica-gel chromatography to obtain the above-identified compound (57 mg, 89%) as a colorless oily material.

IR(KBr)cm$^{-1}$: 1636, 1508, 1424, 1365, 1278, 1223, 1156, 1022, 788. MS(FAB) 429[M+1]$^+$. 1H-NMR(CDCl$_3$): δ 3.29 (4H, m) 3.64(2H, m) 3.96(2H, m) 6.89(1H, t, J=7.3 Hz) 6.95 (2H, d, J=8.1 Hz) 7.23–7.31(4H, m) 7.41–7.46(3H, m) 8.24(1H, s) 8.66(1H, dd, J=1.9 and 4.5 Hz) 8.79(1H, dd, J=1.9 and 8.0H, z).

Example 67

Synthesis of N-phenyl-1-(4-fluorophenyl)-1,4-dihydro[1,8]naphthylidin-4-one-3-carboxamide Thionyl chloride (13.8 µl, 0.19 mmol) was added to a tetrahydrofuran (2 ml) solution of 1-(4-fluorophenyl)-1,4-dihydro[1,8]naphthylidin-4-one-3-carboxylic acid (27 mg, 0.095 mmol) at room temperature and the solution was refluxed for 1.5 hour. The solvent was distilled off under vacuum, whereby a colorless crystal of acid chloride was obtained. Next, triethylamine (40 µl, 0.285 mmol) and aniline (10.4 µl, 0.114 mmol) were added to a methylene chloride (2 ml) solution of this acid chloride at room temperature and the solution was stirred at that temperature for 30 minutes. This was further stirred at 50° C. for 2 hours. The reaction solution was diluted with ethyl acetate (20 ml) and successively washed with water (5 ml) and saturated saline (5 ml), then dried over anhydrous sodium sulfate, then the solvent was distilled off under vacuum. The precipitated crystal was washed with diethylether, then the crystal was obtained by filtration to obtain the above-identified compound (34 mg, quant.) as a slightly yellow crystal.

IR(KBr)cm$^{-1}$: 3054, 1686, 1606, 1508. MS(FAB) 360 [M+1]$^+$. 1H-NMR(CDCl$_3$): δ 7.08–7.16(1H, m) 7.22–7.56 (7H, m) 7.77(2H, d, J=8.1 Hz) 8.73(1H, dd, J=1.9 and 4.5 Hz) 8.89(1H, dd, J=1.9 and 8.0 Hz) 9.08(1H, s) 11.94(1H, brs

Example 68

Synthesis of N-methyl-N-phenyl-1-(4-fluorophenyl)-1,4-dihydro[1,8]naphthylidin-4-one-3-carboxamide The same reaction was carried out as in Example 67, except for using N-methylaniline, instead of aniline, to obtain the above-identified compound (40 mg, quant.) as a colorless crystal.

IR(KBr)cm$^{-1}$: 3052, 1664, 1630, 1505. MS(FAB) 374 [M+1]$^+$. 1H-NMR(CDCl$_3$): δ 3.49(3H, s) 7.12–7.32(101H, m) 7.85–7.96(1H, m) 8.52–8.63(2H, m).

Example 69

Synthesis of 1-(4-fluorophenyl)-N-(2-tolyl)-1,4-dihydro[1,8]naphthylidin-4-one-3-carboxamide The same reaction was carried out as in Example 53, except for using o-toluidine, instead of isopropylamine, to obtain the above-identified compound (61 mg, 81%) as a colorless crystal.

IR(KBr)cm$^{-1}$: 3062, 1680, 1610, 1579, 1557, 1508, 1487, 1418, 1301, 1222, 786, 754. MS(FAB) 374[M+1]$^+$. 1H-NMR(CDCl$_3$): δ 2.52(3H, s) 7.03(1H, t, J=7.3 Hz) 7.23–7.31(4H, m) 7.45(2H, m) 7.50(1H, dd, J=4.5 and 8.0 Hz) 8.31(1H, d, J=8.0 Hz) 8.73(1H, dd, J=1.8 and 4.5 Hz) 8.91(1H, dd, J=1.8 and 8.0 Hz) 9.11(1H, s) 11.80(1H, brs).

Example 70

Synthesis of 1-(4-fluorophenyl)-N-(3-tolyl)-1,4-dihydro[1,8]naphthylidin-4-one-3-carboxamide The same reaction was carried out as in Example 53, except for using m-toluidine, instead of isopropylamine, to obtain the above-identified compound (35 mg, 63%) as a colorless crystal.

IR(KBr)cm$^{-1}$: 3478, 1680, 1610, 1560, 1508, 1482, 1431, 1418, 1294, 1223, 840, 788. MS(FAB) 374[M+1]$^+$. 1—NMR(CDCl$_3$): δ 2.38(3H, s) 6.95(2H, d, J=7.6 Hz) 7.20–7.30(3H, m) 7.44(2H, dd, J=4.7 and 8.9 Hz) 7.51(1H, dd, J=4.4 and 8.0 Hz) 7.60(2H, brs) 8.72(1H, dd, J=1.7 and 4.5 Hz) 8.88(1H, dd, J=2.0 and 7.9 Hz) 9.07(1H, s) 11.87 (1H, brs).

Example 71

Synthesis of 1-(4-fluorophenyl)-N-(4-tolyl)-1,4-dihydro[1,8]naphthylidin-4-one-3-carboxamide The same reaction was carried out as in Example 53, except for using p-toluidine, instead of isopropylamine, to obtain the above-identified compound (57 mg, 76%) as a colorless crystal.

IR(KBr)cm$^{-1}$: 3068, 1683, 1608, 1547, 1507, 1482, 1428, 1416, 1310, 1222, 784. MS(FAB) 374[M+1]$^+$. 1H-NMR (CDCl$_3$): δ 2.34(3H, s) 7.17(2H, d, J=8.3 Hz) 7.30(2H, d, J=1.8 Hz) 7.45(2H, m) 7.51(1H, dd, J=4.5 and 8.0 Hz) 7.66(2H, d, J=8.4 Hz) 8.73(1H, dd, J=1.9 and 4.5 Hz) 8.88(1H, dd, J=1.8 and 8.0 Hz) 9.08(1H, s) 11.86(1H, brs).

Example 72

Synthesis of 1-(4-fluorophenyl)-N-(2.6-xylidyl)-1,4-dihydro[1,8]naphthylidin-4-one-3-carboxamide To a tetrahydrofuran (1 ml) solution of 1-(4-fluorophenyl)-1,4-dihydro[1,8]naphthylidin-4-one-3-carboxylic acid (28 mg, 0.10 mmol), oxalyl chloride (10 µl, 0.114 mmol) and N,N-dimethylformamide (10 µl) were added at a temperature of 0° C., followed by stirring at the same temperature for 1 hour. When the solvent was distilled off under vacuum, the acid chloride was obtained as a colorless crystal. 2,6-xylidine (14 µl, 0.12 mmol) was dissolved in N,N-dimethylformamide (2 ml) and sodium hydride (abt. 5.0 mg of 60% oil suspension, 0.125 mmol), followed by stirring at 70° C. for 3 hours. After allowing to cool to room temperature, the above acid chloride was added and stirred at the same temperature for 19 hours. The reaction mixture was diluted with ethyl acetate (20 ml) and was successively washed with water (5 ml), an aqueous saturated sodium hydrogen carboxylate solution (5 ml), and saturated saline water (5 ml), followed by dried over anhydrous sodium sulfate. The solvent was then distilled off under vacuum. The residue was suspended with diethylether and the precipitate was filtered to obtain the above-identified compound (17 mg, 44%) as a colorless crystal.

IR(KBr)cm$^{-1}$: 3418, 1680, 1605, 1527, 1508, 1475, 1426, 1326, 1299, 1223, 1158, 853, 787, 773. MS(FAB) 388[M+1]$^+$. 1H-NMR(CDCl$_3$): δ 2.32(6H, s) 7.44–7.52(3H, m) 8.73(2H, dd, J=1.9 and 4.4 Hz) 8.90(1H, dd, J=1.9 and 8.0 Hz) 9.908(1H, s) 11.20(1H, brs).

Example 73

Synthesis of 1-(4-fluorophenyl)-N-(2-hydroxyphenyl)-1,4-dihydro[1,8]naphthylidin-4-one-3-carboxamide The same reaction was carried out as in Example 53, except for using o-aminophenol, instead of isopropylamine, to obtain the above-identified compound (21 mg, 28%) as a colorless crystal.

IR(KBr)cm$^{-1}$: 3284, 1668, 1605, 1556, 1512, 1485, 1458, 1430, 1316, 1223, 862, 776. MS(FAB) 376[M+1]$^+$. 1H-NMR(CDCl$_3$): δ 6.91(1H, m) 7.06(1H, d, J=8.5 Hz) 7.17(2H, m) 7.30(2H, t, J=8.5 Hz) 7.46(2H, m) 7.54(1H, m) 8.76(1H, dd, J=2.0 and 4.5 Hz) 8.90(1H, dd, J=2.0 and 8.1 Hz) 9.09(1H, s) 9.78(1H, s) 12.38(1H, brs).

Example 74

Synthesis of 1-(4-fluorophenyl)-N-(3-hydroxyphenyl)-1,4-dihydro[1,8]naphthylidin-4-one-3-carboxamide The same reaction was carried out as in Example 53, except for using m-aminophenol, instead of isopropylamine, to obtain the above-identified compound (47 mg, 84%) as a colorless crystal.

IR(KBr)cm$^{-1}$: 1668, 1607, 1567, 1545, 1508, 1481, 1428, 1418, 1351, 1224, 1160, 789. MS(FAB) 376[M+1]$^+$. 1H-NMR(DMSO-d$_6$): δ 6.52(1H, dd, J=1.8 and 8.0 Hz) 7.00(1H, d, J=8.8 Hz) 7.15(1H, t, J=8.1 Hz) 7.36(1H, s) 7.46 (2H, m) 7.66–7.74(2H, m) 8.82(1H, dd, J=2.0 and 2.9 Hz) 8.86(1H, s) 9.47(1H, s) 11.97(1H, brs).

Example 75

Synthesis of 1-(4-fluorophenyl)-N-(4-hydroxyphenyl)-1,4-dihydro[1,8]naphthylidin-4-one-3-carboxamide The same reaction was carried out as in Example 53, except for using p-aminophenol, instead of isopropylamine, to obtain the above-identified compound (50 mg, 89%) as a colorless crystal.

IR(KBr)cm$^{-1}$: 3418, 1672, 1608, 1572, 1540, 1511, 1486, 1431, 1419, 1337, 1223, 856, 820, 788. MS(FAB) 376[M+1]$^+$. 1H-NMR(DMSO-d$_8$): δ 6.76(1H, d, J=8.8 Hz) 7.45(1H, t, J=8.8 Hz) 7.52(3H, d, J=8.8 Hz) 7.66–7.73(3H, min 8.81(1H, d, J=3.7 Hz) 8.85(1H, s) 9.26(1H, s) 11.79(1H, brs).

Example 76

Synthesis of 1-(4-fluorophenyl)-N-(2-methoxyphenyl)-1,4-dihydro[1,8]naphthylidin-4-one-3-carboxamide The same reaction was carried out as in Example 53, except for using o-anisidine, instead of isopropylamine, to obtain the above-identified compound (67 mg, 86%) as a colorless crystal.

IR(KBr)cm$^{-1}$: 3068, 1676, 1608, 1575, 1540, 1508, 1484; 1429, 1417, 1221, 854, 796, 755, 702. MS(FAB) 390[M+1]$^+$. 1H-NMR(CDCl$_3$): δ 4.05(3H, s) 6.95–7.02(2H, m) 7.07(1H, dd, J=1.6 and 7.8 Hz) 7.29(2H, m) 7.43–7.52(3H, m) 8.57(1H, dd, J=1.5 and 8.0 Hz) 8.71(1H, dd, J=1.9 and 4.5 Hz) 8.93(1H, dd, J=1.9 and 8.0 Hz) 9.08(1H, s) 12.15 (1H, brs).

Example 77

Synthesis of 1-(4-fluorophenyl)-N-(3-methoxyphenyl)-1,4-dihydro[1,8]naphthylidin-4-one-3-carboxamide The same reaction was carried out as in Example 53, except for using m-anisidine, instead of isopropylamine, to obtain the above-identified compound (51 mg, 91%) as a colorless crystal.

IR(KBr)cm$^{-1}$: 1679, 1599, 1560, 1508, 1482, 1426, 1334, 1297, 1223, 1156, 1034, 959, 856, 786. MS(FAB) 390[M+1]$^+$. 1H-NMR(CDCl$_3$): δ 3.84(3H, s) 7.29(4H, m) 7.45(2H, dd, J=4.7 and 8.9 Hz) 7.51(1H, dd, J=4.6 and 8.0 Hz) 8.73(1H, dd, J=1.9 and 4.5 Hz) 8.88(1H, dd, J=1.9 and 8.0 Hz) 9.08(1H, s) 11.93(1H, brs).

Example 78

Synthesis of N-(3-tert-butyldimethylsilyloxymethylphenyl)-1-(4-fluorophenyl)-1,4-dihydro[1,8]naphthylidin-4-one-3-carboxamide The same reaction was carried out as in Example 53, except for using 3-aminobenzyl-tert-butyldimethylsilyl ether, instead of isopropylamine, to obtain the above-identified compound (157 mg, 89%) as a slightly yellow crystal.

IR(KBr)cm$^{-1}$: 3078, 2927, 1682, 1616, 1507, 1417, 1222, 835. MS(FAB) 504[M+1]$^+$. 1H-NMR(CDCl$_3$) 60.12(6H, s) 0.96(9H, s) 4.76(2H, s) 7.12–7.15(1H, m) 7.25–7.36(3H, m) 7.43–7.52(3H, m) 7.66–7.68(1H, m) 7.71(1H, brs) 8.73(1H, dd, J=1.9 and 4.4 Hz) 8.89(1H, dd, J=1.9 and 8.0 Hz) 9.08(1H, s) 11.92(1H, brs).

Example 79

Synthesis of 1-(4-fluorophenyl)-N-(3-hydroxymethylphenyl)-1,4-dihydro[1,8]naphthylidin-4-one-3-carboxamide To a tetrahydrofuran (2 ml) solution of N-(3-tert-butyldimethylsilyloxymethylphenyl)-1-(4-fluorophenyl)-1,4-dihydro[1,8]naphthylidin-4-one-3-carboxamide (140 mg, 0.28 mmol), acetic acid (19 μl, 0.33 mmol) and a 1.0M solution of tetrabutylammonium fluoride in tetrahydrofuran (495 μl, 0.50 mmol) were added at room temperature, followed by stirring at the same temperature overnight. The reaction mixture was diluted with ethyl acetate (30 ml) and successively washed with an aqueous ammonium chloride (10 ml) and saturated saline water (10 ml), followed by drying over anhydrous sodium sulfate. The solvent was distilled off under vacuum. The precipitated crystal was washed with diethylether and the crystal was obtained by filtration. The crystal was further washed with a small amount of dichloromethane, followed by filtration to obtain the above-identified compound (59 mg, 55%) as a colorless crystal.

IR(KBr)cm$^{-1}$: 3408, 1680, 1610, 1568, 1508, 1223, 784. MS(FAB) 390[M+1]$^+$. 1H-NMR(DMSO-d$_6$): δ 4.51–4.53 (2H, m) 7.06–7.09(1H, m) 7.31–7.34(1H, m) 7.45–7.50(2H, m) 7.66–7.76(5H, m) 8.82–8.84(2H, m) 8.89(1H, s) 12.08 (1H, brs).

Example 80

Synthesis of N-(2-acetophenyl)-1-(4-fluorophenyl)-1,4-dihydro[1,8]naphthylidin-4-one-3-carboxamide The same reaction was carried out as in Example 53, except for using 2-aminoacetophenone instead of isopropylamine, to obtain the above-identified compound (54 mg, 68%) as a colorless crystal.

IR(KBr)cm$^{-1}$: 1672, 1604, 1574, 1507, 1482, 1448, 1429, 1247, 1220, 1160, 859, 783, 762. MS(FAB) 402[M+1]$^+$. 1H-NMR(CDCl$_3$): δ 2.71(3H, s) 7.18 (2H, t, J=7.0 Hz) 7.29(2H, m) 7.43–7.49(3H, m) 7.56(1H, m) 7.89(1N, dd, J=1.5 and 8.0 Hz) 8.71(1H, dd, J=1.9 and 4.5 Hz) 9.01(1H, m) 9.03(1H, s) 13.33(1H, brs).

Example 81

Synthesis of N-(3-acetophenyl)-1-(4-fluorophenyl)-1,4-dihydro[1,8]naphthylidin-4-one-3-carboxamide The same reaction was carried out as in Example 53, except for using 3-aminoacetophenone, instead of isopropylamine, to obtain the above-identified compound (50 mg, 83%) as a colorless crystal.

IR(KBr)cm$^{-1}$: 1684, 1610, 1560, 1540, 1508, 1482, 1416, 1299, 1220, 789. MS(FAB) 402[M+1]$^+$. 1H-NMR(CDCl$_3$): δ 2.59(3H, s) 7.28(2H, t, J=8.4 Hz) 7.46(3H, m) 7.53(1H, dd, J=4.5 and 8.0 Hz) 7.73(1H, d, J=7.7 Hz) 8.02(1H, d, J=8.1 Hz) 8.36(1H, s) 8.74 (1H, d, J=8.1 Hz) 8.89(1H, d, J=8.1 Hz) 9.09 (1H, s) 12.12(1H, brs).

Example 82

Synthesis of ethyl 2-[{[1-(4-fluorophenyl)-1,4-dihydro[1,8]naphthylidin-4-one-3-yl]carboxyl}amino]benzoate The same reaction was carried out as in Example 53, except for using ethyl 2-aminobenzoate, instead of isopropylamine, to obtain the above-identified compound (118 mg, 91%) as a colorless crystal.

IR(KBr)cm$^{-1}$: 1709, 1671, 1621, 1601, 1578, 1508, 1485, 1429, 1247, 1084, 781, 753. MS(FAB) 432[M+1]$^+$. 1H-NMR(CDCl$_3$): δ 1.43(3H, t, J=7.1 Hz) 4.53(3H, q, J=7.1 Hz) 7.15 (1H, t, J=7.5 Hz) 7.30(2H, m) 7.44–7.49(3H, m) 7.55(1H, m) 8.08(1H, dd, J=1.5 and 8.0 Hz) 8.69(1H, dd, J=2.4 and 4.3 Hz) 9.00(1H, dd, J=1.9 and 8.0 Hz) 9.05(1H, s) 13.05(1H, brs).

Example 83

Synthesis of 2-[{[1-(4-fluorophenyl)-1,4-dihydro[1,8]naphthylidin-4-one-3-yl]carbonyl}amino]benzoic acid Ethyl 2-[{[1-(4-fluorophenyl)-1,4-dihydro[1,8]naphthylidin-4-one-3-yl]carbonyl}amino]benzoate (39 mg, 0.09 mmol) was dissolved in 2 ml of ethanol and 1N sodium hydroxide (110 μl, 0.11 mmol) was added thereto, followed by heating under reflux for 8 hours. After allowing to cool, 1N hydrochloric acid (120 μl, 0.12 mmol) and water (10 ml) were added and the precipitate was obtained by filtration. Thus, the above-identified compound (37 mg, quant.) was obtained as a colorless crystal.

IR(KBr)cm$^{-1}$: 3450, 1669, 1582, 1508, 1482, 1430, 1285, 1219, 1078, 1089, 752. MS(FAB) 404[M+1]$^+$. 1H-NMR (DMSO-d$_6$): δ 7.20 (1H, t, J=7.2 Hz) 7.46 (2H, t, J=8.8 Hz) 7.58(1H, m) 7.66(1H, m) 7.72(2H, m) 7.94(1H, dd, J=1.6 and 7.9 Hz) 8.55(1H, d, J=8.4 Hz) 8.78(1H, m) 8.84(1H, s) 12.83(1H, s) 13.33(1H, brs).

Example 84

Synthesis of N-[2-(aminocarbonyl)phenyl]-1-(4-fluorophenyl)-1,4-dihydro[1,8]naphthylidin-4-one-3-yl}-3-carboxamide The same reaction was carried out as in Example 53, except for using 2-aminobenzamide, instead of isopropylamine, to obtain the above-identified compound (65 mg, quant.) as a colorless crystal.

IR(KBr)cm$^{-1}$: 3392, 1672, 1608, 1509, 1482, 1430, 1291, 1222, 792, 753. MS(FAB) 403[M+1]$^+$. 1H-NMR(DMSO-d$_8$): δ 7.15 (1N, t, J=7.5 Hz) 7.45(3H, m) 7.58(1H, d, J=7.1 Hz) 7.65(1H, dd, J=4.6 and 7.9 Hz) 7.71(2H, dd, J=4.8 and 8.7 Hz) 7.97(1H, brs) 8.39(1H, d, J=8.3 Hz) 8.76(1H, dd, J=6.8 and 7.9 Hz) 8.78(1H, s) 8.86(1H, s) 12.44(1H, brs).

Example 85

Synthesis of ethyl 3-[{[1-(4-fluorophenyl)-1,4-dihydro[1,8]naphthylidin-4-one-3-yl]carbonyl}amino]benzoate The same reaction was carried out as in Example 53, except for using ethyl 3-aminobenzoate, instead of isopropylamine, to obtain the above-identified compound (118 mg, 91%) as a colorless crystal.

IR(KBr)cm$^{-1}$: 1715, 1684, 1614, 1575, 1507, 1479, 1428, 1299, 1222, 793, 762. MS(FAB) 432[M+1]$^+$. 1H-NMR (CDCl$_3$): δ 1.41(3H, t, J=7.1 Hz) 4.41(3H, q, J=7.1 Hz) 7.29(2H, m) 7.42–7.47(3H, m) 7.53(1H, dd, J=4.5 and 8.0 Hz) 7.82(1H, dd, J=1.1 and 7.7 Hz) 8.11(1H, dd, J=1.0 and 8.0 Hz) 8.33(1H, s) 8.74(1H, dd, J=1.8 and 4.5 Hz) 8.89(1H, dd, J=1.8 and 8.0 Hz) 9.09(1H, s) 12.08(1H, brs).

Example 86

Synthesis of 3-[{[1-(4-fluorophenyl)-1,4-dihydro[1,8]naphthylidin-4-one-3-yl]carbonyl}amino]benzoic acid Ethyl 3-[{[1-(4-fluorophenyl)-1,4-dihydro[1,8]naphthylidin-4-one-3-yl]carbonyl}amino]benzoate (39 mg, 0.09 mmol) was dissolved in 1 ml of N,N-dimethyl formamide and 1N sodium hydroxide (110 μl, 0.11 mmol) was added thereto, followed by stirring at room temperature for 19 hours. 1N hydrochloric acid (120 μl, 0.12 mmol) and water (10 ml) were added and the separated precipitate was obtained by filtration. Thus, the above-identified compound (38 mg, quant.) was obtained as a colorless crystal.

IR(KBr)cm$^{-1}$: 3438, 3152, 1686, 1611, 1546, 1512, 1482, 1416, 1397, 1301, 1224, 854, 792. MS(FAB) 404[M+1]$^+$. 1H-NMR(DMSO-d$_6$): δ 7.45–7.53(3H, m) 7.68–7.75(4H, m) 7.91(1H, d, J=7.8 Hz) 8.38(1H, s) 8.86(1H, d, J=5.8 Hz) 8.90(1H, s) 12.21(1H, s) 12.99(1H, brs).

Example 87

Synthesis of N-[3-(aminocarbonyl)phenyl]-1-(4-fluorophenyl)-1,4-dihydro[1,8]naphthylidin-4-one-3-carboxamide The same reaction was carried out as in Example 53, except for using 3-aminobenzamide, instead of isopropylamine, to obtain the above-identified compound (52 mg, 87%) as a colorless crystal.

IR(KBr)cm$^{-1}$: 3365, 3486, 1684, 1612, 1568, 1508, 1479, 1425, 1348, 1222, 1154, 1098, 844, 822, 792, 687. MS(FAB) 403[M+1]$^+$. 1H-NMR(DMSO-d$_6$): δ 7.35 (1H, brs) 7.45 (3H, m) 7.61(1H, d, J=7.7 Hz) 7.70(3H, m) 8.02(2H, d, J=7.8 Hz) 8.11(1H, s) 8.82(1H, d, J=6.0 Hz) 8.89(1H, s) 12.17(1H, brs).

Example 88

Synthesis of methyl 4-[{[1-(4-fluorophenyl)-1,4-dihydro[1,8]naphthylidin-4-one-3-yl]carbonyl}amino]benzoate The same reaction was carried out as in Example 53, except for using methyl 4-aminobenzoate instead of o-aminophenol, to obtain the above-identified compound (105 mg, 84%) as a colorless crystal.

IR(KBr)cm$^{-1}$: 1705, 1683, 1602, 1558, 1506, 1480, 1418, 1281, 1224, 1176, 1113, 772. MS(FAB) 418[M+1]$^+$. 1H-NMR(DMSO-d$_6$): δ 3.85(3H, s) 7.47(2H, t, J=8.8 Hz) 7.72(3H, m) 7.89(2H, d, J=8.6 Hz) 8.02(2H, d, J=8.6 Hz) 8.82(2H, m) 8.83(1H, s) 8.90(1H, s) 12.39(1H, s).

Example 89

Synthesis of N-[4-(aminocarbonyl)phenyl]-1-(4-fluorophenyl)-1,4-dihydro[1,8]naphthylidin-4-one-3-carboxamide The same reaction was carried out as in Example 53, except for using 4-aminobenzamide, instead of isopropylamine, to obtain the above-identified compound (33 mg, 55%) as a colorless crystal.

IR(KBr)cm$^{-1}$: 3438, 3152, 1686, 1612, 1515, 1482, 1416, 1397, 1300, 1224, 854, 791. MS(FAB) 403[M+1]$^+$. 1H-NMR(DMSO-d$_6$): δ 7.44 (2H, t. J=8.7 Hz) 7.70(3H, m) 7.80(2H, d, J=8.6 Hz) 7.90(2H, d, J=8.6 Hz) 8.26(3H, s) 8.82 (2H, m) 8.91(1H, s) 12.24(1H, brs).

Example 90

Synthesis of N-(2-aminophenyl)-1-(4-fluorophenyl)-1,4-dihydro[1,8]naphthylidin-4-one-3-carboxamide The same reaction was carried out as in Example 53, except for using o-phenylenediamine, instead of isopropylamine, to obtain the above-identified compound (53 mg, 94%) as a yellow crystal.

IR(KBr)cm$^{-1}$: 3417, 3054, 1676, 1602, 1540, 1505, 1482, 1426, 1326, 1221, 1154, 856, 784, 745. MS(FAB) 375[M+1]$^+$. 1H-NMR(CDCl$_3$): δ 4.01(2H, s) 6.86(2H, m) 7.05 (1H, t, J=7.3 and 8.7 Hz) 7.28(2H, m) 7.40(2H, m) 7.5(0 (1H, m) 7.60(2H, dd, J=1.5 and 8.5 Hz) 8.73(1H, dd, J=2.0 and 4.5 Hz) 8.90(1H, dd, J=2.0 and 8.0 Hz) 9.08(1H, d, J=7.44 Hz) 11.64(1H, brs).

Example 91

Synthesis of N-(3-aminophenyl)-1-(4-fluorophenyl)-1,4-dihydro[1,8]naphthylidin-4-one-3-carboxamide The same reaction was carried out as in Example 53, except for using m-phenylenediamine, instead of isopropylamine, to obtain the above-identified compound (18 mg, 32%) as a slightly brown crystal.

IR(KBr)cm$^{-1}$: 3416, 3344, 1680, 1610, 1576, 1504, 1479, 1430, 1327, 1312, 1292, 1249, 1218, 1158, 1096, 1018, 842, 792. MS(FAB) 375[M+1]$^+$. 1H-NMR(CDCl$_3$): δ 3.71(2H, brs) 6.46(2H, dd, J=1.7 and 8.9 Hz) 7.03 (1H, d, J=8.5 Hz) 7.14(1H, t, J=7.9 Hz) 7.30(2H, m) 7.35(1H, t, J=2.0 Hz) 7.45(2H, m) 7.50(2H, dd, J=4.5 and 7.9 Hz) 8.72(1H, dd, J=1.8 and 4.4 Hz) 8.88(1H, dd, J=1.9 and 8.0 Hz) 9.06(1H, d, J=7.4 Hz) 11.84(1H, brs).

Example 92

Synthesis of N-(4-aminophenyl)-1-(4-fluorophenyl)-1,4-dihydro[1,8]naphthylidin-4-one-3-carboxamide The same reaction was carried out as in Example 53, except for using p-phenylenediamine, instead of isopropylamine, to obtain the above-identified compound (33 mg, 59%) as a yellow crystal.

IR(KBr)cm$^{-1}$: 3346, 1672, 1608, 1508, 1483, 1429, 1222, 855, 832, 789. MS(FAB) 375[M+1]$^+$. 1H-NMR(CDCl$_3$): δ 3.61(2H, brs) 6.70(2H, d, J=8.77 Hz) 7.30(2H, m) 7.44(2H, m) 7.50(2H, dd, J=4.5 and 8.0 Hz) 7.56(2H, d, J=8.65 Hz) 8.72(1H, dd, J=1.9 and 4.4 Hz) 8.87(1H, dd, J=1.9 and 8.0 Hz) 9.06(1H, d, J=7.4 Hz) 11.70(1H, s).

Example 93

Synthesis of 1-(4-fluorophenyl)-N-(2-nitrophenyl)-1,4-dihydro[1,8]naphthylidin-4-one-3-carboxamide The same reaction was carried out as in Example 53, except for using o-nitroaniline, instead of isopropylamine, to obtain the above-identified compound (32 mg, 52%) as a yellow crystal.

IR(KBr)cm$^{-1}$: 3430, 1677, 1608, 1578, 1508, 1346, 1270, 1217, 790, 742. MS(FAB) 405[M+1]$^+$. 1H-NMR(CDCl$_3$): δ 7.21–7.32(3H, m) 7.46(2H, m) 7.51(2H, dd, J=4.5 and 8.0 Hz) 7.64(1H, dt, J=1.3 and 8.4 Hz) 8.17 (1H, dd, J=1.5 and 8.3 Hz) 8.72(1H, m) 8.74(1H, m) 8.98 (1H, dd, J=2.0 and 8.0 Hz) 9.04(1H, s) 13.23(1H, s).

Example 94

Synthesis of 1-(4-fluorohenyl)-N-(3-nitrophenyl)-1,4-dihydro[1,8]naphthylidin-4-one-3-carboxamide The same reaction was carried out as in Example 53, except for using m-nitroaniline, instead of isopropylamine, to obtain the above-identified compound (43 mg, 70%) as a colorless crystal.

IR(KBr)cm$^{-1}$: 1684, 1609, 1534, 1507, 1482, 1417, 1349, 1220, 789, 736. MS(FAB) 405[M+1]$^+$. 1H-NMR(CDCl$_3$): δ 7.30(2H, m) 7.45(2H, m) 7.54(2H, m) 7.98(1H, m) 8.08(1H, m) 8.73(1H, m) 8.75(1H, dd, J=1.8 and 4.4 Hz) 8.89 (1H, dd, J=2.0 and 8.0 Hz) 9.08(1H, s) 13.32(1H, s).

Example 95

Synthesis of 1-(4-fluorophenyl)-N-(4-nitrophenyl)-1,4-dihydro[1,8]naphthylidin-4-one-3-carboxamide The same reaction was carried out as in Example 53, except for using p-nitroaniline, instead of isopropylamine, to obtain the above-identified compound (50 mg, 82%) as a colorless crystal.

IR(KBr)cm$^{-1}$: 3480, 1695, 1613, 1567, 1508, 1482, 1418, 1344, 1219, 853, 786. MS(FAB) 405[M+1]$^+$. 1H-NMR (CDCl$_3$): δ 7.30(2H, m) 7.45(2H, dd, J=41.6 and 8.9 Hz) 7.55(1H, m) 7.94(2H, d, J=9.1 Hz) 8.26(1H, d, J=9.1 Hz) 8.75(1H, m) 8.88(1H, d, J=8.1 Hz) 9.07(1H, s) 12.46(1H, s).

Example 96

Synthesis of N-(tert-butyloxycarbonylbenzamidin-3-yl)-1-(4-fluorophenyl)-1,4-dihydro[1,8]naphthylidin-4-one-3-carboxamide The same reaction was carried out as in Example 53, except for using 3-(tert-butyloxycarbonyl)aminobenzamide, instead of isopropylamine, to obtain the above-identified compound (163 mg, 93%) as a slightly yellow crystal.

IR(KBr)cm$^{-1}$: 3232, 1754, 1704, 1626, 1574, 1230, 1144. MS(FAB) 502[M+1]$^+$. 1H-NMR(CDCl$_3$): δ 1.53(9H, s) 7.27–7.31(2H, m) 7.42–7.47(3H, m) 7.51–7.54(1H; m) 7.67–7.69(1H, m) 7.93–7.95(1H, m) 8.26(1H, brs) 8.73(1H, dd, J=1.9 and 4.5 Hz) 8.89(1H, dd, J=1.9 and 8.00 Hz) 9.06(1H, s) 12.11(1H, brs).

Example 97

Synthesis of N-(benzamidin-3-yl)-1-(4-fluorophenyl)-1,4-dihydro[1,8]naphthylidin-4-one-3-carboxamide hydrochloride To a dichloromethane (0.5 ml) solution of N-(tert-butyloxycarbonylbenzamidin-3-yl)-1-($^4$-fluorophenyl)-1,4-dihydro[1,8]naphthylidin-4-one-3-carboxamide (20 mg, 0.04 mol), 4N hydrochloric acid-dioxane (2 ml, 8 mmol) was added at room temperature, followed by stirring for 48 hours. The solvent was distilled off under vacuum. The precipitated crystal was washed with diethyl ether to obtain the above-identified compound (16 mg, 94%) by filtration as a slightly yellow crystal.

IR(KBr)cm$^{-1}$: 3048, 1699, 1614, 1563, 1510, 1472, 820. MS(FAB) 402[M+1]$^+$. 1H-NMR(MeOH): δ 7.35–7.39(2H, m) 7.51–7.66(5H, m) 7.97–8.00(1H, m) 8.29(1H, brs) 8.74–8.77(1H, m) 8.88–8.92(1H, m) 9.05–10.07(1H, m).

Example 98

Synthesis of 1,N-bis-(4-fluorophenyl)-1,4-dihydro[1,8]naphthylidin-4-one-3-carboxamide The same reaction was carried out as in Example 53, except for using 4-fluoroaniline instead of isopropylamine, to obtain the above-identified compound (61 mg, 92%) as a colorless crystal.

IR(KBr)cm$^{-1}$: 3084, 1684, 1611, 1567, 1508, 1484, 1418, 1296, 1222, 1155, 1101, 827, 785. MS(FAB) 378[M+1]$^+$. 1H-NMR(CDCl$_3$): δ 7.06(2H, t, J=7.0 Hz) 7.29(2H, m) 7.43–7.47(2H, m) 7.52(1H, dd, J=4.5 and 7.9 Hz) 7.73(2H, m) 8.74(1H, dd, J=1.9 and 4.5 Hz) 8.88(1H, dd, J=2.0 and 8.0 Hz) 9.07(1H, s) 11.94(1H, brs).

Example 99

Synthesis of N-(2.6-dichlorophenyl)-1-(4-fluorophenyl)-1,4-dihydro[1,8]naphthylidin-4-one-3-carboxamide The same reaction was carried out as in Example 67, except for using 2,6-dichloroaniline instead of aniline, to obtain the above-identified compound (17 mg, 56%) as a colorless crystal.

IR(KBr)cm$^{-1}$: 3076, 1686, 1615, 1508. MS(FAB) 430 [M+1]$^+$. 1H-NMR(CDCl$_3$)5: 7.18–7.23(1H, m) 7.28–7.33 (2H, m) 7.40–7.50(4H, m) 7.51 (1H, dd, J=4.4 and 8.0 Hz) 8.73(1H, dd, J=1.9 and 4.4 Hz) 8.91(1H, dd, J=1.9 and 8.0 Hz) 9.07(1H, s) 11.60(1H, brs).

Example 100

Synthesis of N-(2-biphenyl)-1-(4-fluorophenyl)-1,4-dihydro[1,8]naphthylidin-4-one-3-carboxamide The same reaction was carried out as in Example 53, except for using 2-aminobiphenyl, instead of isopropylamine, to obtain the above-identified compound (41 mg, 39%) as a colorless crystal.

IR(KBr)cm$^{-1}$: 3068, 1676, 1608, 1575, 1540, 1508, 1484, 1429, 1417, 1350, 1331, 1300, 1221, 1156, 854, 796, 755, 702. MS(FAB) 436[M+1]$^+$. 1H-NMR(CDCl$_3$): δ 7.19–7.29 (4H, m) 7.32(1H, dd, J=1.6 and 7.6 Hz) 7.37–7.45(4H, m) 7.49(4H, d, J=4.44 Hz) 8.36(1H, d, J=7.8 Hz) 8.65(1H, dd, J=1.9 and 4.5 Hz) 8.70(1H, dd, J=1.9 and 8.0 Hz) 9.00(1H, s) 11.57(1H, brs).

Example 101

Synthesis of 1-(4-fluorophenyl)-N-(2-pyridyl)-1,4-dihydro[1,8]naphthylidin-4-one-3-carboxamide The same reaction was carried out as in Example 67, except for using 2-aminopyridine, instead of aniline, to obtain the above-identified compound (32 mg, 32%) as a colorless crystal.

IR(KBr)cm$^{-1}$: 1686, 1607, 1530, 1508, 1490, 1338, 1228, 1213, 1110, 970, 882, 829, 786. MS(FAB) 361[M+1]$^+$. 1H-NMR(CDCl$_3$): δ 6.70(1H, dd, J=4.7 and 7.9 Hz) 7.03–7.10(2H, m) 7.32–7.38(1H, m) 7.64–7.71(2H, m) 7.83 (1H, d, J=8.9 Hz) 7.90–8.00(2H, m) 8.39(1H, dd, J=1.9 and 4.7 Hz) 8.64(1H, s) 9.24(1H, d, J=7.1 Hz) 10.87(1H, brs).

Example 102

Synthesis of 1-(4-fluorophenyl)-N-(3-pyridyl)-1,4-dihydro[1,8]naphthylidin-4-one-3-carboxamide The same reaction was carried out as in Example 67, except for using 3-aminopyridine instead of aniline, to obtain the above-identified compound (70 mg, 69%) as a colorless crystal.

IR(KBr)cm$^{-1}$: 3045, 1680, 1608, 1556, 1508, 1480, 1224, 1020, 790. MS(FAB) 361[M+1]$^+$. 1H-NMR(CDCl$_3$): δ 7.25–7.32(2H, m) 7.42–7.47(2H, m) 7.53 (1H, dd, J=4.5 and 8.0 Hz) 8.27–8.32(1H, m) 8.37(1H, dd, J=1.4 and 4.8 Hz) 8.74(1H, dd, J=1.9 and 4.5 Hz) 8.88–8.91(2H, m) 9.07(1H, s) 12.1(1H, brs).

Example 103

Synthesis of 1-(4-fluorophenyl)-N-(4-pyridyl)-1,4-dihydro[1,8]naphthylidin-4-one-3-carboxamide The same reaction was carried out as in Example 67, except for using 4-aminopyridine, instead of aniline, to obtain the above-identified compound (17 mg, 67%) as a colorless crystal.

IR(KBr)cm$^{-1}$: 3019, 1690, 1613, 1534, 1508. MS(FAB) 361[M+1]$^+$. 1H-NMR (CDCl$_3$): δ 7.25–7.32(2H, m) 7.45 (2H, dd, J=4.6 and 8.8 Hz) 7.54(1H, dd, J=4.5 and 8.0 Hz) 7.66–7.72(2H, m) 8.52–8.57(2H, m) 8.74(1H, dd, J=1.8 and 4.5 Hz) 8.88(1H, dd, J=1.8 and 8.0 Hz) 9.06(1H, s).

Example 104

Synthesis of 1-(4-fluorophenyl)-N-(3-methylpyridin-4-yl)-1,4-dihydro[1,8]naphthylidin-4-one-3-carboxamide The same reaction was carried out as in Example 53, except for using 4-amino-3-picoline, instead of isopropylamine, to obtain the above-identified compound (32 mg, 86%) as a colorless crystal.

IR(KBr)cm$^{-1}$: 3424, 1691, 1611, 1572, 1534, 1508, 1482, 1426, 1296, 1223, 788. MS(FAB) 375[M+1]$^+$. 1H-NMR (CDCl$_3$): δ 2.50(3H, s) 7.30(1H, m) 7.46(2H, m) 7.53(1H, dd, J=4.4 and 8.1 Hz) 8.42(3H, m) 8.75(1H, dd, J=1.9 and 4.5 Hz) 8.91(1H, dd, J=1.9 and 8.0 Hz) 9.09(1H, s) 12.14 (1H, brs).

Example 105

Synthesis of N-(2-chloropyridin-3-yl)-1-(4-fluorophenyl)-1,4-dihydro[1,8]naphthylidin-4-one-3-carboxamide The same reaction was carried out as in Example 53, except for using 3-amino-2-chloropyridine, instead of isopropylamine, to obtain the above-identified compound (49 mg, 83%) as a colorless crystal.

IR(KBr)cm$^{-1}$: 3450, 1684, 1615, 1540, 1508, 1482, 1428, 1396, 1332, 1221, 788. MS(FAB) 395[M+1]$^+$. 1H-NMR (CDCl$_3$): δ 7.28–7.32(3H, m) 7.46(2H, m) 7.53(1H, dd, J=4.5 and 8.0 Hz) 8.14(1H, dd, J=1.5 and 4.5 Hz) 8.74(1H, dd, J=1.8 and 4.5 Hz) 8.94(1H, m) 9.05(1H, s) 12.47(1H, brs).

Example 106

Synthesis of N-(3.5-dichloropyridin-4-yl)-1-(4-fluorophenyl)-1,4-dihydro[1,8]naphthylidin-4-one-3-carboxamide Thionyl chloride (54 41, 0.74 mmol) was added to a tetrahydrofuran (2 ml) solution of 1-(4-fluorophenyl)-1,4-dihydro[1,8]naphthylidin-4-one-3-carboxylic acid (70 mg, 0.25 mmol) at room temperature and the solution was refluxed for 1 hour. The solvent was distilled off under vacuum, whereby a colorless crystal of acid chloride was obtained. Next, triethylamine (103 μl, 0.74 mmol), 4-amino-3,5-dichloropyridine (44 mg, 0.271 mmol), and N,N-dimethylaminopyridine (2 mg) were added to a methylene chloride (2 ml) solution of this acid chloride at room temperature and the solution was stirred at that temperature for 19 hours. The reaction solution was diluted with ethyl acetate (20 ml) and successively washed with water (5 ml) and saturated saline (5 ml), then dried over anhydrous sodium sulfate, then the solvent was distilled off under vacuum. The residue was purified by silica gel column chromatography (hexane/ethyl acetate=1.5/1) to obtain the above-identified compound (52 mg, 49%) as a colorless crystal.

IR(KBr)cm$^{-1}$: 3068, 1692, 1619, 1546, 1506, 1482, 1417, 1327, 1222, 1790. MS(FAB) 428[M+1]$^+$. 1H-NMR (CDCl$_3$): δ 7.26–7.31(2H, m) 7.44–7.47(2H, m) 7.53(1H, dd, J=4.5 and 8.1 Hz) 8.57(2H, s) 8.74(1H, dd, J=2.0 and 4.5 Hz) 8.92(1H, dd, J=2.0 and 7.9 Hz) 9.07(1H, s) 12.0(1H, brs).

Example 107

Synthesis of 1-(4-fluorophenyl)-N-(4-pyrimidyl)-1,4-dihydro[1,8]naphthylidin-4-one-3-carboxamide The same reaction was carried out as in Example 53, except for using 4-aminopyrimidine, instead of isopropylamine, to obtain the above-identified compound (38 mg, 70%) as a slightly yellow crystal.

IR(KBr)cm$^{-1}$: 3468, 1691, 1618, 1568, 1508, 1481, 1418, 1310, 1223, 934, 890. MS(FAB) 362[M+1]$^+$. 1H-NMR (CDCl$_3$): δ 7.30(2H, m) 7.45(2H, dd, J=4.5 and 8.7 Hz) 7.53(2H, dd, J=4.5 and 8.0 Hz) 8.27(1H, d, J=5.77 Hz) 8.64(1H, d, J=5.9 Hz) 8.74(1H, m) 8.91(1H, m) 8.97(1H, s) 9.02(1H, s) 12.57(1H, brs).

Example 108

Synthesis of 1-(4-fluorophenyl)-N-(4,6-dichloropyrimidin-5-yl)-1,4-dihydro[1,8]naphthylidin-4-one-3-carboxamide The same reaction was carried out as in Example 106, except for using 5-amino-4,6-dichloropyrimidine, instead of 4-amino-3,5-dichloropyridine, to obtain the above-identified compound (14 mg, 16%) as a colorless crystal.

IR(KBr)cm$^{-1}$: 3480, 1692, 1621, 1505, 1482, 1428, 1411, 1348, 1327, 1222, 858, 792; MS(FAB) 430[M+1]$^+$. 1H-NMR(CDCl$_3$): δ 7.30(2H, m) 7.45(1H, d, J=4.5 Hz) 7.47(1H, m) 7.54(1H, m) 8.71(1H, s) 8.76(1H, dd, J=1.7 and 4.5 Hz) 8.91(1H, dd, J=1.8 and 7.8 Hz) 9.06(1H, s) 11.97 (1H, s).

Example 109

Synthesis of 1-(4-fluorophenyl)-N-pyrazinyl-1,4-dihydro[1,8]naphthylidin-4-one-3-carboxamide Thionyl chloride (51 μl, 0.70 mmol) was added to a toluene (2 ml) solution of 1-(4-fluorophenyl)-1,4-dihydro[1,8]naphthylidin-4-one-3-carboxylic acid (80 mg, 0.28 mmol) at room temperature and the solution was heated at 95° C. for 1.5 hours. The solvent was distilled off under vacuum, whereby a colorless crystal of acid chloride was obtained. Next, N,N-dimethylaminopyridine (2 mg) and aminopyrazine (29.4 mg, 0.31 mmol) were added to a pyridine (2 ml) solution of this acid chloride at room temperature and the solution was stirred at 60° C. for 3 hours. The reaction solution was diluted with water (10 ml), whereupon the crystal precipitated. The precipitated crystal was obtained by filtration and the crystal was washed with diethyl ether to obtain the above-identified compound (70 mg, 69%) as a colorless crystal.

IR(KBr)cm$^{-1}$: 3078, 1688, 1619, 1540, 1508, 1482, 1413, 1296, 1209, 1009, 834, 787. MS(FAB) 362 [M+1]$^+$. 1H-NMR(CDCl$_3$): δ 7.26–7.32(1H, m) 7.42–7.48(2H, m) 7.50–7.56(1H, m) 8.35(2H, d, J=1.4 Hz) 8.73(1H, dd, J=1.9 and 4.5 Hz) 8.91(1H, dd, J=1.9 and 8.0 Hz) 9.08(1H, s) 9.65(1H, d, J=1.9 Hz) 12.49(1H, brs).

Example 110

Synthesis of 1-(4-fluorophenyl)-N-(1-isoquinolyl)-1,4-dihydro[1,8]naphthylidin-4-one-3-carboxamide The same reaction was carried out as in Example 53, except for using 1-aminoisoquinoline, instead of isopropylamine, to obtain the above-mentioned compound (43 mg, 69%) as a yellow crystal.

IR(KBr)cm$^{-1}$: 3476, 1672, 1611, 1503, 1413, 1260, 1218, 1118, 822, 792, 762. MS(FAB) 411[M+1]$^+$. 1H-NMR (CDCl$_3$): δ 6.72(1H, dd, J=4.7 and 7.8Hz) 7.06(1H, t, J=8.7 Hz) 7.47(1H, d, J=7.7 Hz) 7.69(2H, dd, J=4.8 and 8.9 Hz) 7.84(2H, m) 7.94(2H, m) 8.40(1H, dd, J=1.8 and 4.8 Hz) 8.64(1H, s) 8.53 (1H, d, J=7.65 Hz) 9.13(1H, d, J=8.2 Hz) 10.92(1H, brs).

Example 111

Synthesis of 1-(4-fluorophenyl)-N-(2-quinolyl)-1,4-dihydro[1,8]naphthylidin-4-one-3-carboxamide The same reaction was carried out as in Example 53, except for using 2-aminoquinoline, instead of isopropylamine, to obtain the above-identified compound (58 mg, 71%) as a colorless crystal.

IR(KBr)cm$^{-1}$: 1686, 1602, 1574, 1508, 1500, 1428, 1324, 1224, 1158, 786. MS(FAB) 411[M+1]$^+$. 1H-NMR(CDCl$_3$): δ 7.27–7.33(2H, m) 7.43–7.48(3H, m) 7.52(1H, m) 7.67(1H, dt, J=1.4 and 7.0 Hz) 7.78(1H, d, J=8.0 Hz) 7.98(1H, d, J=8.5 Hz) 8.18(1H, d, J=8.9 Hz) 8.53(1H, d, J=8.9 Hz) 8.73(1H, dd, J=1.8 and 4.5 Hz) 8.95(1H, dd, J=2.0 and 8.1 Hz) 9.09(1H, s) 12.61(1H, brs).

Example 112

Synthesis of 1-(4-fluorophenyl)-N-(3-quinolyl)-1,4-dihydro[1,8]naphthylidin-4-one-3-carboxamide The same reaction was carried out as in Example 53, except for using 3-aminoquinoline, instead of isopropylamine, to obtain the above-identified compound (60 mg, 73%) as a colorless crystal.

IR(KBr)cm$^{-1}$: 1677, 1604, 1557, 1508, 1480, 1430, 1342, 1228, 1158, 900, 858, 820, 788, 748. MS(FAB) 411[M+1]$^+$. 1H-NMR(CDCl$_3$): δ 7.30(1H, m) 7.47(2H, m) 7.54(2H, m) 7.63(1H, m) 7.83(1H, d, J=8.2 Hz) 8.07(1H, d, J=8.3 Hz) 8.75(1H, dd, J=1.8 and 4.4 Hz) 8.90(1H, d, J=1.8 Hz) 8.92(1H, dd, J=1.9 and 7.8 Hz) 9.05(1H, d, J=2.5 Hz) 9.12(1H, s) 12.35(1H, brs).

Example 113

Synthesis of 1-(4-fluorophenyl)-N-(5-quinolyl)-1,4-dihydro[1,8]naphthylidin-4-one-3-carboxamide The same reaction was carried out as in Example 53, except for using 5-aminoquinoline, instead of isopropylamine, to obtain the above-identified compound (57 mg, 92%) as a yellow crystal.

IR(KBr)cm$^{-1}$: 3458, 3062, 1684, 1608, 1566, 1508, 1485, 1418, 1319, 1226, 803, 783. MS(FAB) 411[M+1]$^+$. 1H-NMR(CDCl$_3$): δ 7.31(2H, t, J=8.5 Hz) 7.47–7.52(2H, m) 7.56(1H, dd, J=4.5 and 8.0 Hz) 7.65(1H, t. J=7.9 Hz) 7.78(1H, d, J=8.1 Hz) 8.19(1H, d, J=6.1 Hz) 8.69(1H, d, J=6.1 Hz) 8.75–8.78(3H, m) 8.99(1H, dd, J=2.0 and 7.9 Hz) 9.15(1H, s) 9.28(1H, s) 12.73(1H, brs).

Example 114

Synthesis of 1-(4-fluorophenyl)-N-(5-isoquinolyl)-1,4-dihydro[1,8]naphthylidin-4-one-3-carboxamide The same reaction was carried out as in Example 53, except for using 5-aminoisoquinoline, instead of isopropylamine, to obtain the above-identified compound (49 mg, 79%) as a colorless crystal.

IR(KBr)cm$^{-1}$: 3457, 1684, 1615, 1568, 1508, 1418, 1326, 1224, 790. MS(FAB) 411[M+1]$^+$. 1H-NMR(CDCl$_3$): δ 7.31 (2H, m) 7.48(2H, dd, J=4.6 and 8.83 Hz) 7.55(2H, dd, J=4.5 and 8.2 Hz) 7.76(1H, t, J=8.2 Hz) 7.94(1H, d, J=8.14 Hz) 8.52(1H, d, J=7.8 Hz) 8.75(1H, d, J=8.6 Hz) 8.77(1H, dd, J=1.5 and 4.2 Hz) 8.96(1H, m) 8.98(1H, s) 9.16(1H, s) 12.67(1H, brs).

Example 115

Synthesis of 1-(4-fluorophenyl)-N-(5-quinolyl)-1,4-dihydro[1,8]naphthylidin-4-one-3-carboxamide The same reaction was carried out as in Example 53, except for using 8-aminoquinoline, instead of isopropylamine, to obtain the above-identified compound (54 mg, 87%) as a colorless crystal.

IR(KBr)cm$^{-1}$: 1673, 1596, 1543, 1509, 1481, 1418, 1323, 1221, 1156, 820, 785. MS(FAB) 411[M+1]$^+$. 1H-NMR (CDCl$_3$): δ 7.28–7.33(2H, m) 7.47–7.52(4H, m) 7.57(2H, m) 8.19(1H, dd, J=1.7 and 8.3 Hz) 8.72(1H, dd, J=1.9 and 5.5 Hz) 9.00–9.06(2H, m) 9.12(1H, dd, J=1.7 and 4.2 Hz) 9.14(1H, s) 13.54(1H, brs).

Example 116

Synthesis of 1-(4-fluorophenyl)-N-(2-thiazolyl)-1,4-dihydro[1,8]naphthylidin-4-one-3-carboxamide The same reaction was carried out as in Example 53, except for using 2-aminothiazole, instead of isopropylamine, to obtain the above-identified compound (45 mg, 82%) as a yellow crystal.

IR(KBr)cm$^{-1}$: 3080, 1672, 1616, 1544, 1508, 1480, 1428, 1317, 1219, 1165, 858, 842, 792. MS(FAB) 367[M+1]$^+$. 1H-NMR(CDCl$_3$): δ 7.01(1H, d, J=3.4 Hz) 7.28(2H, m) 7.44(2H, m) 7.52(1H, m) 7.54(1H, d, J=2.6 Hz) 8.73(1H, m) 8.91(1H, d, J=8.0 Hz) 9.06(1H, s) 13.10(1H, brs).

Example 117

Synthesis of 1-(4-fluorophenyl)-N-(2-benzimidazolyl)-1,4-dihydro[1,8]naphthylidin-4-one-3-carboxamide The same reaction was carried out as in Example 53, except for using 2-aminobenzimidazole, instead of isopropylamine, to obtain the above-identified compound (32 mg, 52%) as a yellow crystal.

IR(KBr)cm$^{-1}$: 3068, 1676, 1602, 1540, 1508, 1475, 1429, 1329, 1263, 1221, 1196, 883, 794, 751. MS(FAB) 417[M+1]$^+$. 1H-NMR(CDCl$_3$): δ 7.28–7.33(3H, m) 7.43–7.47(3H, m) 7.52(1H, m) 7.54(1H, dd, J=4.4 and 7.9 Hz) 7.83(1H, d, J=7.7 Hz) 7.87(1H, d, J=8.22 Hz) 8.73(H, dd, J=1.8 and 4.4 Hz) 8.92(1H, dd, J=1.8 and 8.0 Hz) 9.08(1H, s) 13.27(1H, brs).

Example 118

Synthesis of N-(3,5-dichloropyridin-4-yl)-1-phenyl-1,4-dihydro[1,8]naphthylidin-4-one-3-carboxamide To a tetrahydrofuran (1 ml) solution of 1-phenyl-1,4-dihydro[1,8]naphthylidin-4-one-3-carboxylic acid (27 mg, 0.10 mmol), thionyl chloride (15 µl, 0.20 mmol) and N,N-dimethyl formamide (10 µl) were added, followed by stirring on heating under reflux for 1 hour. The solvent was distilled off to obtain the acid chloride as a colorless crystal. 4-amino-3,5-dichloropyridine (18 mg, 0.11 mmol) was dissolved in N,N-dimethyl formamide (2 ml) and sodium hydride (abt. 60% oil suspension 5.0 mg, 0.125 mmol) was added thereto, followed by stirring at room temperature for 30 minutes. The above acid chloride was added thereto, followed by stirring at the same temperature for 19 hours. The reaction mixture was diluted with ethyl acetate (20 ml) and successively washed with water (5 ml), an aqueous saturated sodium hydrogen carboxylate solution (5 ml) and saturated saline water (5 ml), and dried over anhydrous sodium sulfate, followed by distilling off the solvent under vacuum. The residue was suspended in ether to obtain the above-identified compound (30 mg, 73%) by filtration as a colorless crystal.

IR(KBr)cm$^{-1}$: 1699, 1617, 1544, 1512, 1486, 1424, 1326, 1237, 1196, 1096, 1056, 950, 877, 786, 700. MS(FAB) 411[M+1]$^+$. 1H-NMR(CDCl$_3$): δ 7.47(2H, m) 7.53(1H, dd, J=4.5 and 8.0 Hz) 7.58–7.64(3H, m) 8.57(2H, s) 8.76(1FI, dd, J=1.9 and 4.4 Hz) 8.92(1H, dd, J=1.9 and 8.0 Hz) 9.10(1H, s) 2.08(1I, s).

Example 119

Synthesis of 1-phenyl-N-[2-(4-pyridyl)ethyl]-1,4-dihydro[1,8]naphthylidin-4-one-3-carboxamide The same reaction was carried out as in Example 53, except for using 1-phenyl-1,4-dihydro[1,89 naphthylidin-4-one-3-carboxylic acid instead of 1-(4-fluorophenyl)-1,4-dihydro[1,8]naphthylidin-4-one-3-carboxylic acid and also using 4-aminoethylpyridine instead of isopropylamine to obtain the above-identified compound (9 mg, 28%) as a colorless crystal.

IR(KBr)cm$^{-1}$: 3182, 3046, 1661, 1608, 1540, 1500, 1447, 1365, 1259, 1130, 993, 805. MS(FAB) 337[M+1]$^+$ MS(FAB) 417[M+1]$^+$. 1H-NMR(CDCl$_3$): δ 1.50 (3H, t, J=7.2 Hz) 2.69(2H, t, J=7.2 Hz) 3.78(2H, q, J=7.2 Hz) 7.21(2H, m) 7.29(1H, d, J=8.2 Hz) 8.52(21. d, J=1.5 Hz) 8.62(1H, d, J=8.2 Hz) 8.89(1H, s) 10.04(1H, brs).

Example 120

Synthesis of N-(4-pyridyl)-1-(4-tolyl)-1,4-dihydro[1,8]naphthylidin-4-one-3-carboxamide The same reaction was carried out as in Example 53, except for using 1-($^4$-tolyl)-1,4-dihydro[1,8]naphthylidin-4-one-3-carboxylic acid instead of 1-(4-fluorophenyl)-1,4-dihydro[1,8]naphthylidin-4-one-3-carboxylic acid and also using 4-aminopyridine instead of isopropylamine to obtain the above-identified compound (162 mg, 85%) as a colorless crystal.

IR(KBr)cm$^{-1}$: 2976, 1690, 1604, 1532, 1482, 1426, 1326. MS(FAB) 357[M 1]$^+$. 1H-NMR(CDCl$_3$): δ 2.49(3H, s) 7.32–7.42(4H, m) 7.50–7.54(1H, m) 7.69–7.70(2H, m) 8.53–8.55(2H, m) 8.76(1H, dd, J=1.9 and 4.5 Hz) 8.88(1H, dd, J=1.9 and 7.9 Hz) 9.08(1H, s) 12.26(1H, brs).

Example 121

Synthesis of N-(3,5-dichloropyridin-4-yl)-1-(4-tolyl)-1,4-dihydro[1,8]naphthylidin-4-one-3-carboxamide The same reaction was carried out as in Example 118, except for using 1-(4-tolyl)-1,4-dihydro[1,8]naphthylidin-4-one-3-carboxylic acid instead of 1-phenyl-1,4-dihydro[1,8]naphthylidin-4-one-3-carboxylic acid to obtain the above-identified compound (186 mg, 82%) as a colorless crystal.

IR(KBr)cm$^{-1}$: 3034, 1691, 1618, 1560, 1508, 1425, 791. MS(FAB) 425[M+1]$^+$. 1H-NMR(CDCl$_3$): δ 2.49(3H, s) 7.33–7.41(4H, m) 7.50–7.53(1H, m) 8.57 (2H, s) 8.76(1H, dd, J=1.7 and 4.4H) 8.91(1H, dd, J=1.7 and 8.0 Hz) 9.08 (1H, s) 12.09(1H, brs).

Example 122

Synthesis of 1-(4-methoxyphenyl)-N-(4-pyridyl)-1,4-dihydro[1,8]naphthylidin-4-one-3-carboxamide The same reaction was carried out as in Example 53, except for using 1-(4-methoxyphenyl)-1,4-dihydro[1,8]naphthylidin-4-one-3-carboxylic acid instead of 1-(4-fluorophenyl)-1,4-dihydro[1,8]naphthylidin-4-one-3-carboxylic acid and also using 4-aminopyridine instead of isopropylamine to obtain the above-identified compound (163 mg, 86%) as a colorless crystal.

IR(KBr)cm$^{-1}$: 2990, 1688, 1594, 1511, 1418, 1238; 784. MS(FAB) 373[M+1]$^+$. 1H-NMR(CDCl$_3$): δ 3.91(3H, s) 7.08–7.10(2H, m) 7.35–7.38(2H, m) 7.50–7.54(1H, m) 7.68–7.70(2H, m) 8.53–8.55(2H, m) 8.77(1H, dd, J=1.9 and 4.5 Hz) 8.88(1H, dd, J=1.9 and 7.9 Hz) 9.08(1H, s) 12.26 (1H, brs).

Example 123

Synthesis of N-(3,5-dichloropyridin-4-yl)-1-(4-methoxyphenyl)-1,4-dihydro[1,8]naphthyldin-4-one-3-carboxamide The same reaction was carried out as in Example 118, except for using 1-(4-methoxyphenyl)-1,4-dihydro[1,8]naphthylidin-4-one-3-carboxylic acid, instead of 1-phenyl-1,4-dihydro[1,8]naphthylidin-4-one-3-carboxylic acid, to obtain the above-identified compound (120 mg, 54%) as a slightly yellow crystal.

IR(KBr)cm$^{-1}$: 2936, 1686, 1618, 1546, 1479, 1421, 791. MS(FAB) 441[M+1]$^+$. 1H-NMR(CDCl$_3$): δ 3.91(3H, s) 7.07–7.10(2H, m) 7.36–7.39(2H, m) 7.50–7.54(1H, m) 8.57 (2H, s) 8.77(1H, dd, J=1.9 and 4.5 Hz) 8.91(1H, dd, J=1.9 and 7.9 Hz) 9.08(1H, s) 12.10(1H, brs).

Example 124

Synthesis of 1-(4-chlorophenyl)-N-(4-pyridyl)-1,4-dihydro[1,8]naphthylidin-4-one-3-carboxamide The same reaction was carried out as in Example 53, except for using 1-(4-chlorophenyl)-1,4-dihydro[1,8]naphthylidin-4-one-3-carboxylic acid instead of 1-(4-fluorophenyl)-1,4-dihydro[1,8]naphthylidin-4-one-3-carboxylic acid and also using 4-aminopyridine instead of isopropyl amine to obtain the above-identified compound (230 mg, 92%) as a slightly yellow crystal.

IR(KBr)cm$^{-1}$: 2980, 1686, 1611, 1530, 1492, 1426, 784. MS(FAB) 377[M+1]$^+$. 1H-NMR(CDCl$_3$): δ 7.40–7.43(2H, m) 7.52–7.60(3H, m) 7.68–7.70(2H, m) 8.53–8.55(2H, m) 8.75(1H, dd, J=1.9 and 4.5 Hz) 8.88(1H, dd, J=0.9 and E1.0 Hz) 9.05(1H, s) 12.18(1H, brs).

Example 125

Synthesis of 1-(4-chlorophenyl)-N-(3,5-dichloropyridin-4-yl)-1,4-dihydro[1,8]naphthylidin-4-one-3-carboxamide The same reaction was carried out as in Example 118, except for using 1-(4-chlorophenyl)-1,4-dihydro[1,8]naphthylidin-4-one-3-carboxylic acid, instead of 1-phenyl-1,4-dihydro[1,8]naphthylidin-4-one-3-carboxylic acid, to obtain the above-identified compound (230 mg, 78%) as a colorless crystal.

IR(KBr)cm$^{-1}$: 3045, 1684, 1618, 1546, 1482, 1425, 788. MS(FAB) 445[M+1]$^+$. 1H-NMR(CDCl$_3$): δ 7.41–7.43(2H, m) 7.52–7.60(3H, m) 8.57(2H, s) 8.74–8.76(1H, m) 8.92 (1H, dd, J=1.9 and 7.9 Hz) 9.06(1H, s) 12.01(1H, brs).

Example 126

Synthesis of 1-(3-tert-butyldimethylsilyloxymethylphenyl)-N-(4-pyridyl)-1,4-dihydro[1,8]naphthylidin-4-one-3-carboxamide To a dichloromethane (12 ml) solution of 1-(3-tert-butyldimethylsilyloxymethylphenyl)-1,4-dihydro[1,8]naphthylidin-4-one-3-carboxylic acid (250 mg, 0.61 mmol), 4-aminopyridine (69 mg, 0.73 mmol), triethylamine (212 μl, 1.52 mmol), and 2-chloro-1,3-dimethylimidazolynium chloride (134 mg, 0.79 mmol) were added at room temperature, followed by stirring at the same temperature for 1 hour. The reaction mixture was diluted with dichloromethane (40 ml) and successively washed with saturated aqueous sodium hydrogen sulfate solution (10 ml) and water (10 ml) and dried over anhydrous sodium sulfate, followed by distilling off the solvent under vacuum. The precipitated crystal was washed with diethyl ether and the crystal is filtered to obtain the above-identified compound (138 mg, 47%) as a colorless crystal.

IR(KBr)cm$^{-1}$: 2930, 1686, 1586, 1534, 1421, 790. MS(FAB) 487[M+1]$^+$. 1H-NMR(CDCl$_3$): δ 0.13(6H, s) 0.94(9H, s) 4.85(2H, s) 7.42–7.59(5H, m) 7.69–7.71(2H, m) 8.53–8.55(2H, m) 8.73–8.75(1H, m) 8.87–8.89(1H, m) 9.09(] H, s) 12.27(1H, brs).

Example 127

Synthesis of 1-(3-hydroxymethylphenyl)-N-(4-pyridyl)-1,4-dihydro[1,8]naphthylidin-4-one-3-carboxamide To a tetrahydrofuran (2 ml) solution of 1-(3-tert-butyldimethylsilyloxymethylphenyl)-N-(4-pyridyl)-1,4-dihydro[1,8]naphthylidin-4-one-3-carboxamide (120 mg, 0.25 mmol), acetic acid (17 μl, 0.30 mmol) and a 1.0M tetrahydrofuran solution (370 μl, 0.37 mmol) of tetrabutylammonium fluoride were added at room temperature and stirred at the same temperature for 5 hours. Further, N,N-dimethyl formamide (2 ml) and a 1.0M tetrahydrofuran solution of tetrabutylammonium fluoride (185 μl, 0.19 mmol) were added thereto at the same temperature, followed by stirring overnight. The solvent was distilled off under vacuum and the resultant crystal was washed with diethyl ether and the crystal was recovered by filtration. The crystal was further washed with ethyl acetate and the crystal was filtered to obtain the above-identified compound (76 mg, 83%) as a colorless crystal.

IR(KBr)cm$^{-1}$: 2925, 1688, 1601, 1538, 1478, 1422, 790. MS(FAB) 373[M+1]$^+$. 1H-NMR(DMSO-d$_6$): δ 4.50–4.52 (2H, m) 7.39–7.50(4H, m) 7.58–7.63(3H, m) 8.38–8.40(2H, m) 8.70–8.77(3H, m) 12.20(1H, brs).

Example 128

Synthesis of N-(2,6-dichlorophenyl)-1-(3-nitrophenyl)-1,4-dihydro[1,8]naphthylidin-4-one-3-carboxamide The same reaction was carried out as in Example 67, except for using 1-(3-nitrophenyl)-1,4-dihydro[1,8]naphthylidin-4-one-3-carboxylic acid, instead of 1-(4-fluorophenyl)-1,4-dihydro[1,8]naphthylidin-4-one-3-carboxylic acid, and using 2,6-dichloroaniline, instead of aniline, to obtain the above-identified compound (11 mg, 24%) as a colorless crystal.

IR(KBr)cm$^{-1}$: 3064, 1690, 1622, 1582, 1531, 1414, 1315, 1246, 820, 738. MS(FAB) 344[M+1]$^+$. 1H-NMR(CDCl$_3$): δ

7.49(2H, dd, J=1.5 and 4.6 Hz) 7.59(1H, dd, J=3.5 and 7.9 Hz) 7.69(2H, dd, J=1.5 and 4.8 Hz) 8.55(2H, dd, J=1.5 and 4.8 Hz) 8.75(1H, dd, J=2.0 and 4.5 Hz) 8.88–8.92(3H, m) 9.07(1H, s) 2.14(1H, brs).

Example 129

Synthesis of 1-(tert-butyloxycarbonylbenzamidin-3-yl)-N-(4-pyridyl)-1,4-dihydro[1,8]naphthylidin-4-one-3-carboxamide The same reaction was carried out as in Example 126 except for using 1-(tert-butyloxycarbonylbenzamidin-3-yl)-1,4-dihydro[1,8]naphthylidin-4-one-3-carboxylic acid, instead of 1-(3-tert-butyldimethylsilyloxymethylphenyl)-1,4-dihydro[1,8]naphthylidin-4-one-3-carboxylic acid, to obtain the above-identified compound (69 mg, 58%) as a colorless crystal.

IR(KBr)cm$^{-1}$: 1689, 1600, 1534, 1290, 1166, 790. MS(FAB) 485[M+1]$^+$. 1H-NMR(DMSO-d$_6$): δ 1.43(9H, s) 7.69–7.75(4H, m) 7.82–7.77(1H, m) 8.13–8.19(2H, m) 8.49–8.51(2H, m) 8.82–8.84(2H, m) 8.96(1H, s) 12.30(1H, brs).

Example 130

Synthesis of 1-(benzamidin-3-yl)-N-(4-pyridyl)-1,4-dihydro[1,8]naphthylidin-4-one-3-carboxamide The same reaction was carried out as in Example 97, except for using 1-(tert-butyloxycarbonylbenzamidin-3-yl)-N-(4-pyridyl)-1,4-dihydro[1,8]naphthylidin-4-one-3-carboxamide, instead of N-(tert-butyloxycarbonyl benzamidin-3-yl)-1-(4-fluorophenyl)-1,4-dihydro[1,8]naphthylidin-4-one-3-carboxamide to obtain the above-identified compound (44 mg, 94%) as a colorless crystal.

IR(KBr)cm$^{-1}$: 3055, 1700, 1614, 1563, 1511, 1473. MS(FAB) 385[M+1]$^+$. 1H-NMR(DMSO-d$_6$): δ 7.75–7.89 (2H, m) 8.02–8.14(3H, m) 8.30–8.33(2H, m) 8.78–8.86(4H, m) 9.11(1H, s) 9.30(2H, brs) 9.55(2H, brs) 12.99(1H, brs).

Example 131

Synthesis of 1-(2-pyridyl)-N-(3-pyridyl)-1,4-dihydro[1,8]naphthylidin-4-one-3-carboxamide The same reaction was carried out as in Example 66, except for using 1-(2-pyridyl)-1,4-dihydro[1,8]naphthylidin-4-one-3-carboxylic acid, instead of 1-(4-fluorophenyl)-1,4-dihydro[1,8]naphthylidin-4-one-3-carboxylic acid and also using 3-aminopyridine, instead of 4-phenylpiperazine to obtain the above-identified compound (20 mg, 29%) as a colorless crystal.

IR(KBr)cm$^{-1}$: 1697, 1606, 1544, 1483, 1466, 1426, 1324, 1240, 790, 704. MS(FAB) 344[M+1]$^+$. 1H-NMR(DMSO-d$_6$): δ 7.43(1H, dd, J=4.5 and 8.1 Hz) 7.66 (1H, dd, J=5.0 and 7.5 Hz) 7.74(1H, dd, J=4.7 and 7.9 Hz) 7.88(1H, d, J=8.0 Hz) 8.13(1H, m) 8.22(1H, m) 8.34(1H, m) 8.72(1H, d, J=3.7 Hz) 8.84(2H, m) 8.91(1H, d, J=2.4 Hz) 9.20(1H, s) 12.04(1H, brs).

Example 132

Synthesis of N-(4-pyridyl)-1-(2-pyridyl)-1,4-dihydro[1,8]naphthylidin-4-one-3-carboxamide The same reaction was carried out as in Example 53, except for using 1-(2-pyridyl)-1,4-dihydro[1,8]naphthylidin-4-one-3-carboxylic acid, instead of 1-(4-fluorophenyl)-1,4-dihydro[1,8]naphthylidin-4-one-3-carboxylic acid and also using 4-aminopyridine, instead of isopropylamine to obtain the above-identified compound (54 mg, 65%) as a colorless crystal.

IR(KBr)cm$^{-1}$: 3074, 1702, 1619, 1599, 1578, 1535, 1426. MS (FAB) 344[M+1]$^+$. 1H-NMR(CDCl$_3$): δ 7.49–7.58(2H, m) 7.68–7.73(3H, m) 7.96–8.02(1H, m) 8.52–8.56(2H, m) 8.68–8.72(1H, m) 8.75–8.78(1H, m) 8.88–8.92(1H, m) 9.39 (1H, s) 12.17(1H, brs).

Example 133

Synthesis of N-(3.5-dichloropyridin-4-yl)-1-(2-pyridyl)-1,4-dihydro[1,8]naphthylidin-4-one-3-carboxamide The same reaction was carried out as in Example 118, except for using 1-(2-pyridyl)-1,4-dihydro[1,8] naphthylidin-4-one-3-carboxylic acid, instead of 1-phenyl-1,4-dihydro[1,8]naphthylidin-4-one-3-carboxylic acid to obtain the above-identified compound (19 mg, 19%) as a colorless crystal.

IR(KBr)cm$^{-1}$: 3034, 1687, 1606, 1579, 1530, 1418. MS (FAB) 358[M+1]$^+$. 1H-NMR(CDCl$_3$): δ 7.48–7.57(2H, m) 7.68–7.72(1H, m) 7.92–8.01(1H, m) 8.56(2H, s) 8.66–8.71 (1H, m) 8.72–8.76(1H, m) 8.88–8.94(1H, m) 9.38(1H, s) 11.98(1H, brs).

Example 134

Synthesis of 1,N-bis-(3-pyridyl)-1,4-dihydro[1,8] naphthylidin-4-one-3-carboxamide The same reaction was carried out as in Example 66, except for using 1-(3-pyridyl)-1,4-dihydro[1,8] naphthylidin-4-one-3-carboxylic acid, instead of 1-(4-fluorophenyl)-1,4-dihydro[1,8]naphthylidin-4-one-3-carboxylic acid and also using 3-aminopyridine, instead of 4-phenylpiperazin to obtain the above-identified compound (9 mg, 13%) as a colorless crystal.

IR(KBr)cm$^{-1}$: 3055, 1687, 1606, 1574, 1542, 1484, 1423, 1326, 1298, 1252, 1193, 1030, 852, 796, 718, 705. MS(FAB) 344[M+1]$^+$. 1H-NMR(DMSO-d$_6$): δ 7.43(1H, dd, J=5.5 and 8.2 Hz) 7.67–7.74(3H, m) 8.14(1H, m) 8.23(1H, m) 8.33 (1H, m) 8.77(1H, d, J=5.1 Hz) 8.82–8.87(2H, m) 8.92(1H, d, J=2.6 Hz) 9.00(1H, s) 12.11(1H, brs).

Example 135

Synthesis of 1-(3-pyridyl)-N-(4-pyridyl)-1,4-dihydro[1,8] naphthylidin-4-one-3-carboxamide The same reaction was carried out as in Example 66, except for using 1-(3-pyridyl)-1,4-dihydro[1,8] naphthylidin-4-one-3-carboxylic acid, instead of 1-(4-fluorophenyl)-1,4-dihydro[1,8]naphthylidin-4-one-3-carboxylic acid and also using 4-aminopyridine, instead of phenylpiperazine to obtain the above-identified compound (20 mg, 29%) as a colorless crystal.

IR(KBr)cm$^{-1}$: 3030, 1697, 1596, 1574, 1536, 1478, 1422, 1352, 1322, 1296, 1250, 1205, 1030, 795, 714. MS(FAB) 344[M+1]$^+$. 1H-NMR(CDCl$_3$): δ 7.70(2H, m) 7.74(2H, d, J=7.6 Hz) 8.14(1H, d, J=8.1 Hz) 8.50(2H, d, J=5.2 Hz) 8.77(1H, d, J=4.4 Hz) 8.82–8.86(3H, m) 9.00(1H, s) 12.27 (1H, brs).

Example 136

Synthesis of N-(3,5-dichloropyridin-4-yl)-1-(3-pyridyl)-1,4-dihydro[1,8]naphthylidin-4-one-3-carboxamide The same reaction was carried out as in Example 118, except for using 1-(4-pyridyl)-1,4-dihydro[1,8] naphthylidin-4-one-3-carboxylic acid, instead of 1-phenyl-1,4-dihydro[1,8]naphthylidin-4-one-3-carboxylic acid to obtain the above-identified compound (30 mg, 24%) as a colorless crystal.

IR(KBr)cm$^{-1}$: 3021, 1706, 1626, 1548, 1478, 1422, 1326, 788. MS(FAB) 412[M+1]$^+$. 1H-NMR(CDCl$_3$): δ 7.52–7.59 (2H, m) 7.83–7.86(2H, m) 8.57(1H, s) 8.74(1H, dd, J=1.9 and 4.5 Hz) 8.78–8.79(1H, m) 8.82(1H, dd, J=1.3 and 4.7 Hz) 8.93(1H, dd, J=1.9 and 8.0 Hz) 9.07(1H, s) 11.96 (1H, brs).

Example 137

Synthesis of N-(2,6-dichlorophenyl)-1-(4-pyridyl)-1,4-dihydro[1,8]naphthylidin-4-one-3-carboxamide The same reaction was carried out as in Example 118, except for using 1-(4-pyridyl)-1,4-dihydro[1,8] naphthylidin-4-one-3-carboxylic acid, instead of 1-phenyl-1,4-dihydro[1,8]naphthylidin-4-one-3-carboxylic acid and also using 2,6-dichloroaniline, instead of 4-amino-3,5-dichloropyridine to obtain the above-identified compound (12 mg, 10%) as a colorless crystal.

IR(KBr)cm$^{-1}$: 3060, 1684, 1586, 1480, 1428, 1320, 790. MS(FAB) 411[M+1]$^+$. 1H-NMR(CDCl$_3$): δ 7.19–7.23(1H, m) 7.41–7.43(2H, m) 7.49–7.50(2H, m) 7.55–7.58(1H, m) 8.73–8.75(1H, m) 8.88–8.90(2H, m) 8.93(1H, dd, J=2.0 and 8.0 Hz) 9.09(1H, s) 11.52(1H, brs).

Example 138

Synthesis of N-(3-pyridyl)-1-(4-pyridyl)-1,4-dihydro[1,8]naphthylidin-4-one-3-carboxamide The same reaction was carried out as in Example 66, except for using 1-(4-pyridyl)-1,4-dihydro[1,8] naphthylidin-4-one-3-carboxylic acid, instead of 1-(4-fluorophenyl)-1,4-dihydro[1,8]naphthylidin-4-one-3-carboxylic acid and also using 3-aminopyridine, instead of 4-phenylpiperazine to obtain the above-identified compound (137 mg, 40%) as a colorless crystal.

IR(KBr)cm$^{-1}$: 3055, 1684, 1605, 1582, 1556, 1501, 1479, 1414, 1354, 1320, 1294, 1244, 1220, 1019, 850, 790, 702. MS(FAB) 344[M+1]$^+$. 1H-NMR(CDCl$_3$): δ 7.31(1H, m) 7.49(2H, dd, J=1.5 and 4.6 Hz) 7.57(1H, dd, J=4.5 and 3.0 Hz) 8.30(1H, m) 8.38(1H, dd, J=1.2 and 4.7 Hz) 8.74(1H, dd, J=1.9 and 4.4 Hz) 8.88–8.91(3H, m) 9.08(1H, s) 11.99 (1H, brs).

Example 139

Synthesis of 1,N-bis-(4-pyridyl)-1,4-dihydro[1,8] naphthylidin-4-one-3-carboxamide The same reaction was carried out as in Example 67, except for using 1-(4-pyridyl)-1,4-dihydro[1,8] naphthylidin-4-one-3-carboxylic acid, instead of 1-(4-fluorophenyl)-1,4-dihydro[1,8]naphthylidin-4-one-3-carboxylic acid, and also using 4-aminopyridine, instead of aniline, to obtain the above-identified compound (55 mg, 53%) as a colorless crystal.

IR(KBr)cm$^{-1}$: 3078, 1702, 1603, 1570, 1533. MS(FAB) 344[M+1]$^+$. 1H-NMR(CDCl$_3$): δ 7.10–7.17(2H, m) 7.44 (2H, d, J=8.1 Hz) 7.76–7.82(3H, m) 8.35–8.46 (2H, m) 8.53–8.56(1H, m) 8.91 (1H, s) 16.1 (1H, brs).

Example 140

Synthesis of N-(3-methylpyridin-4-yl)-1-(4-pyridyl)-1,4-dihydro[1,8]naphthylidin-4-one-3-carboxamide The same reaction was carried out as in Example 53, except for using 1-(4-pyridyl)-1,4-dihydro[1,8] naphthylidin-4-one-3-carboxylic acid, instead of 1-(4-fluorophenyl)-1,4-dihydro[1,8]naphthylidin-4-one-3-carboxylic acid and also using 4-amino-3-methylpyridine, instead of isopropylamine to obtain the above-identified compound (64 mg, 60%) as a slightly yellow crystal.

IR(KBr)cm$^{-1}$: 3080, 1706, 1630, 1609, 1545, 1427. MS (FAB) 412[M+1]$^+$. 1H-NMR(CDCl$_3$): δ 2.50(3H, s) 7.49 (2H, dd, J=1.6 and 4.6 Hz) 7.57(1H, dd, J=4.5 and 8.1 Hz) 8.37–8.44(3H, m) 8.73–8.76(1H, m) 8.87–8.92(3H, m) 9.09 (1H, s) 12.05(1H, brs).

Example 141

Synthesis of N-(3.5-dichloropyridin-4-yl)-1-(4-pyridyl)-1,4-dihydro[1,8]naphthylidin-4-one-3-carboxamide The same reaction was carried out as in Example 118, except for using 1-(4-pyridyl)-1,4-dihydro[1,8] naphthylidin-4-one-3-carboxylic acid, instead of 1-phenyl-1,4-dihydro[1,8]naphthylidin-4-one-3-carboxylic acid, to obtain the above-identified compound (83 mg, 59%) as a colorless crystal.

IR(KBr)cm$^{-1}$: 2924, 1704, 1628, 1548, 1480, 1413, 788. MS(FAB) 412[M+1]$^+$. 1H-NMR(CDCl$_3$): δ 7.48–7.72(3H, m) 8.58(2H, s) 8.75(1H, dd, J=2.0 and 4.5 Hz) 8.89–8.94 (3H, m) 9.07(1H, s) 11.91(1H, brs).

Example 142

Synthesis of 1-(2-tert-butyloxycarbonylaminopyridin-5-yl)-N-(4-pyridyl)-1,4-dihydro[1,8]naphthylidin-4-one-3-carboxamide The same reaction was carried out as in Example 126, except for using 1-(2-tert-butyloxycarbonylaminopyridin-5-yl)-1,4-dihydro[1,8]naphthylidin-4-one-3-carboxylic acid, instead of 1-(3-tert-butyldimethylsilyloxymethylphenyl)-1, 4-dihydro[1,8]naphthylidin-4-one-3-carboxylic acid, to obtain the above-identified compound (20 mg, 23%) as a colorless crystal.

IR(KBr)cm$^{-1}$: 2973, 1726, 1687, 1593, 1534, 1480, 1427, 1162. MS(FAB) 459[M+1]$^+$. 1H-NMR(CDCl$_3$): δ 1.55(9H, s) 7.48(1H, brs) 7.52–7.56(1H, m) 7.69(1H, dd, J=1.5 and 4.8 Hz) 7.76–7.79(1H, m) 8.57(1H, s) 8.20–8.23(1H, m) 8.34–8.35(1H, m) 8.53–8.55(1H, m) 8.72–8.74(1H, m) 8.87 (1H, dd, J=1.9 and 7.9 Hz) 9.05(1H, s) 12.17(1H, brs).

Example 143

Synthesis of 1-(2-aminopyridin-5-yl)-N-(4-pyridyl)-1,4-dihydro[1,8]naphthylidin-4-one-3-carboxamide hydrochloride The same reaction was carried out as in Example 97, except for using 1-(2-tert-butyloxycarbonylaminopyridin-5-yl)-N-(4-pyridyl)-1,4-dihydro[1,8]naphthylidin-4-one-3-carboxamide, instead of N-(tert-butyloxycarbonylbenzamidin-3-yl-1-(4-fluorophenyl)-1,4-dihydro[1,8]naphthylidin-4-one-3-carboxamide to obtain the above-identified compound (8 mg, 53%) as a colorless crystal.

IR(KBr)cm$^{-1}$: 3318, 1683, 1610, 1540, 1507, 1425, 794. MS(FAB) 359[M+1]$^+$. 1H-NMR(MeOH): δ 7.05–7.16(1H, m) 7.68–7.70(1H, m) 8.28–8.37(3H, m) 8.65–8.68(3H, m) 8.81–8.83(1H, m) 8.90–8.93(1H, m) 9.19(1H, s).

Example 144

Synthesis of 1-(2-benzyloxypyridin-5-yl)-N-(4-pyridyl)-1,4-dihydro[1,8]naphthylidin-4-one-3-carboxamide The same reaction was carried out as in Example 53, except for using 1-(2-benzyloxypyridin-5-yl)-1,4-dihydro[1,8]naphthylidin-4-one-3-carboxylic acid, instead of 1-(4-fluorophenyl)-1,4-dihydro[1,8]naphthylidin-4-one-3- carboxylic acid and also using 4-aminopyridine, instead of isopropylamine, to obtain the above-identified compound (193 mg, 80%) as a slightly orange crystal.

IR(KBr)cm$^{-1}$: 3031, 1690, 1610, 1487, 785. MS(FAB) 450[M+1]$^+$. 1H-NMR (CDCl$_3$): δ 5.49(2H, s) 7.00–7.02 (1H, m) 7.35–7.56(6H, m) 7.68–7.71 (3H, m) 8.28–8.29(1H, m) 8.53–8.55(2H, m) 8.75(1H, dd, J=1.8 and 4.4 Hz) 8.88(1H, dd, J=1.8 and 8.0 Hz) 9.05(1H, s) 12.17(1H, brs).

Example 145

Synthesis of 1-(2-hydroxypyridin-5-yl)-N-(4-pyridyl)-1,4-dihydro[1,8]naphthylidin-4-one-3-carboxamide To a mixed solution of 1-(2-benzyloxypyridin-5-yl)-N-(4-pyridyl)-1,4-dihydro[1,8]naphthylidin-4-one-3-carboxamide (120 mg, 0.27 mmol), ethanol (13 ml) and tetrahydrofuran (7 ml), 10% Pd-C (50 mg) was added and stirred at room temperature for 44 hours under a hydrogen gas atmosphere. The reaction mixture was filtered and the solvent was distilled off under vacuum from the filtrate. Thereafter, the precipitated crystal was washed with diethyl ether and the crystal was filtered to obtain the above-identified compound (75 mg, 78%) as a slightly green crystal.

IR(KBr)cm$^{-1}$: 1686, 1609, 1535, 1481, 1422, 788. MS(FAB) 360[M+1]$^+$. 1H-NMR(DMSO-d$_6$): δ 6.45–6.48 (1H, m) 7.63–7.74(4H, m) 7.89(1H, brs) 8.49–8.51(2H, m) 8.80(1H, dd, J=1.8 and 7.9 Hz) 8.88(1H, dd, J=1.8 and 4.5 Hz) 8.96(1H, s) 12.27(1H, brs).

Example 146

Synthesis of 1-(2-benzyloxypyridin-5-yl)-N-(3,5-dichloropyridin-4-yl)-1,4-dihydro[1,8]naphthylidin-4-one-3-carboxamide The same reaction was carried out as in Example 118, except for using 1-(2-benzyloxypyridin-5-yl)-1,4-dihydro[1,8]naphthylidin-4-one-3-carboxylic acid, instead of 1-(4-fluorophenyl)-1,4-dihydro[1,8]naphthylidin-4-one-3-carboxylic acid, to obtain the above-identified compound (339 mg, 81%) as a slightly yellow crystal.

IR(KBr)cm$^{-1}$: 1706, 1629, 1550, 1491, 1425, 788. MS(FAB) 518[M+1]$^+$. 1H-NMR(CDCl$_3$): δ 5.48(2H, s) 7.00(1H, m) 7.35–7.43(3H, m) 7.48–7.56(3H, m) 7.68–7.17 (1H, m) 8.29–8.30(1H, m) 8.57(2H, s) 8.75(1H, dd, J=1.9 and 4.5 Hz) 8.92(1H, dd, J=1.9 and 8.0 Hz) 9.06(1H, s) 11.20(1H, brs).

Example 147

Synthesis of N-(3,5-dichloropyridin-4-yl)-1-(2-hydroxypyridin-5-yl)-1,4-dihydro[1,8]naphthylidin-4-one-3-carboxamide The same reaction was carried out as in Example 145, except for using N-(3,5-dichloropyridin-4-yl)-1-(2-benzyloxypyridin-5-yl)-1,4-dihydro[1,8]naphthylidin-4-one-3-carboxamide, instead of 1-(2-benzyloxypyridin-5-yl)-N-(4-pyridyl)-1,4-dihydro[1,8]naphthylidin-4-one-3-carboxamide, to obtain the above-identified compound (170 mg, 89%) as a colorless crystal.

IR(KBr)cm$^{-1}$: 3039, 1669, 1608, 1542, 1482, 1428, 783. MS(FAB) 428[M+1]$^+$. 1H-NMR(DMSO-d$_6$): δ 6.44–6.59 (1H, m) 7.67–7.69(1H, m) 7.70(1H, dd, J=4.5 and 8.0 Hz) 7.90(1H, brs) 8.72(2H, s) 8.80(1H, dd, J=1.8 and 8.0 Hz) 8.89(1H, dd, J=1.8 and 4.5 Hz) 8.94(1H, s) 12.02(1H, brs).

Example 148

Synthesis of 1-(1-isoquinonyl)-N-(4-pyridyl)-1,4-dihydro[1,8]naphthylidin-4-one-3-carboxamide The same reaction was carried out as in Example 53, except for using 1-(1-isoquinonyl)-1,4-dihydro[1,8]naphthylidin-4-one-3-carboxylic acid, instead of 1-(4-fluorophenyl)-1,4-dihydro[1,8]naphthylidin-4-one-3-carboxylic acid and also using 4-aminopyridine, instead of isopropylamine, to obtain the above-identified compound (21 mg, 54%) as a slightly yellow crystal.

IR(KBr)cm$^{-1}$: 3568, 3026, 1688, 1593, 1534, 1481, 1427, 1386, 1344, 1297, 1270, 1242, 1204, 1054, 991, 820, 789. MS(FAB) 394[M+1]$^+$. 1H-NMR(CDCl$_3$): δ 7.40(1H, d, J=8.5 Hz) 7.51(1H, dd, J=3.3 and 7.9 Hz) 7.57(1H, t, J=7.2 Hz) 7.70(2H, d, J=5.0 Hz) 7.81(1H, t, J=7.6 Hz) 7.97(1H, d, J=5.6 Hz) 8.04(1H, d, J=8.6 Hz) 8.54(1H, brs) 8.57(1H, d, J=1.7 Hz) 8.58(1H, d, J=1.9 Hz) 8.60(1H, d, J=5.7 Hz) 8.91 (1H, dd, J=1.9 and 8.1 Hz) 9.17(1H, s) 12.2 (1H, brs).

Example 149

Synthesis of 1-(8-quinonyl)-N-(4-pyridyl)-1,4-dihydro[1,8]naphthylidin-4-one-3-carboxamide The same reaction was carried out as in Example 53, except for using 1-(8-quinonyl)-1,4-dihydro[1,8]naphthylidin-4-one-3-carboxylic acid, instead of 1-(4-fluorophenyl)-1,4-dihydro[1,8]naphthylidin-4-one-3-carboxylic acid and also using 4-aminopyridine instead of isopropylamine to obtain the above-identified compound (20 mg, 51%) as an orange crystal.

IR(KBr)cm$^{-1}$: 3500, 1681, 1612, 1537, 1500, 1480, 1425, 1329, 1254, 1196, 787. MS(FAB) 394[M+1]$^+$. 1H-NMR (CDCl$_3$): δ 7.46–7.52(2H, m) 7.71(2H, m) 7.77(1H, m) 7.88(1H, d, J=7.1 Hz) 8.10(1H, d, J=8.22 Hz) 8.31(1H, dd, J=1.6 and 8.4 Hz) 8.52(2H, d, J=8.2 Hz) 8.58(1H, m) 8.78(1H, m) 8.90(1H, dd, J=1.9 and 7.9 Hz) 9.08(1H, s) 12.37(1H, brs).

Example 150

Synthesis of 1-(2-tert-butyloxycarbonylaminopyrimidin-5-yl)-N-(4-pyridyl)-1,4-dihydro[1,8]naphthylidin-4-one-3-carboxamide The same reaction was carried out as in Example 126, except for using 1-(2-tert-butyloxycarbonylaminopyrimidin-5-yl)-1,4-dihydro[1,8]naphthylidin-4-one-3-carboxylic acid, instead of 1-(3-tert-butyldimethylsilyloxymethylphenyl)-1,4-dihydro[1,8]naphthylidin-4-one-3-carboxylic acid, to obtain the above-identified compound (42 mg, 29%) as a slightly yellow crystal.

IR(KBr)cm$^{-1}$: 3068, 1748, 1687, 1604, 1517, 1480, 1161. MS(FAB) 460[M+1]$^+$. 1H-NMR(DMSO-d$_6$): δ 1.51(9H, s) 7.72–7.76(3H, m) 8.50–8.52(2H, m) 8.82–8.86(2H, m) 8.88 (2H, s) 9.13(1H, s) 10.45(1H, brs) 12.25(1H, s).

Example 151

Synthesis of N-(4-pyridyl)-1-(2-aminopyrimidin-5-yl)-1,4-dihydro[1,8]naphthylidin-4-one-3-carboxamide hydrochloride The same reaction was carried out as in Example 97, except for using 1-(2-tert-butyloxycarbonylaminopyrimidin-5-yl)-N-(4-pyridyl)-1,4-dihydro[1,8]naphthylidin-4-one-3-carboxamide, instead of N-(tert-butyloxycarbonylbenzamidin-3-yl)-1-(4-fluorophenyl)-1,4-dihydro[1,8]naphthylidin-4-one-3- carboxamide, to obtain the above-identified compound (16 mg, 88%) as a colorless crystal.

IR(KBr)cm$^{-1}$: 3062, 1686, 1608, 1342, 1475, 1191, 794. MS(FAB) 360[M+1]$^+$. 1H-NMR(DMSO-d$_6$): δ 7.73–7.77 (1H, m) 8.30–8.33(2H, m) 8.47(2H, s) 8.76–8.79(2H, m) 8.82(1H, dd, J=1.8 and 8.0 Hz) 8.90(1H, d, J=1.8 and 4.4 Hz). 9.08(1H, s) 13.03(1H, brs).

Example 152

Synthesis of N-(3,5-dichloropyridin-4-yl)-1-(2-thiazolyl)-1,4-dihydro[1,8]naphthylidin-4-one-3-carboxamide The same reaction was carried out as in Example 118, except for using 1-(2-thiazolyl)-1,4-dihydro[1,8]naphthylidin-4-one-3-carboxylic acid, instead of 1-(4-fluorophenyl)-1,4-dihydro[1,8]naphthylidin-4-one-3-carboxylic acid, to obtain the above-identified compound (37 mg, 34%) as a slightly yellow crystal.

IR(KBr)cm$^{-1}$: 3072, 1697, 1633, 1558, 1506, 1430, 1238. MS(FAB) 418[M+1]$^+$. 1H-NMR(CDCl$_3$): δ 7.41(1H, d, J=3.5 Hz) 7.64–7.67(1H, m) 7.78(1H, d, J=3.5 Hz) 8.58(2H, s) 8.94–8.97(2H, n) 10.41(1H, s) 11.78(1H, brs).

Example 153

Synthesis of 1-(4-fluorophenyl)-N-(3-hydroxypropyl)-1,4-dihydro[1,8]naphthylidin-4-one-3-carboxamide The same reaction was carried out as in Example 53, except for using 3-amino-1-propanol, instead of isopropylamine, to obtain the above-identified compound (190 mg, 79%) as a colorless crystal.

IR(KBr)cm$^{-1}$: 3340, 1669, 1540, 1511, 1430, 1216, 797. MS(FAB) 342[M+1]$^+$. 1H-NMR(CDCl$_3$): δ 1.79–1.83(2H, m) 3.60–3.68(5H, m) 7.25–7.29(2H, m) 7.40–7.44(2H, m) 7.48(1H, dd, J=4.5 and 8.0 Hz) 8.71(1H, dd, J=1.9 and 4.5 Hz) 8.83(1H, dd, J=1.9 and 8.0 Hz) 8.90(1H, s) 9.94(1H, brs).

Example 154

Synthesis of 1-(4-fluorophenyl)-N-[(R)-2-hydroxypropyl]-1,4-dihydro[1,8]naphthylidin-4-one-3-carboxamide The same reaction was carried out as in Example 53, except for using (R)-(–)-1-amino-2-propanol, instead of isopropylamine, to obtain the above-identified compound (166 mg, 86%) as a colorless crystal.

IR(KBr)cm$^{-1}$: 3422, 1657, 1509, 1482, 1429, 783. MS(FAB) 342[M+1]$^+$. 1H-NMR(CDCl$_3$): δ 1.26(3H, d, J=6.3 Hz) 3.24–3.25(1H, m) 3.43–3.64(2H, m) 4.05–4.08 (1H, m) 7.25–7.29(2H, m) 7.40–7.44(2H, m) 7.48(1H, dd, J=4.5 and 8.0 Hz) 8.70(1H, dd, J=1.8 and 4.5 Hz) 8.84(1H, dd, J=1.8 and 8.0 Hz) 8.99 (1H, s) 10.10(1H, brs).

Example 155

Synthesis of 1-(4-fluorophenyl)-N-f(S)-2-hydroxypropyl]-1,4-dihydro[1,8]naphthylidin-4-one-3-carboxamide The same reaction was carried out as in Example 53, except for using (S)-(+)-1-amino-2-propanol, instead of isopropylamine, to obtain the above-identified compound (153 mg, 80%) as a slightly yellow crystal.

IR(KBr)cm$^{-1}$: 3422, 1658, 1538, 1482, 1428, 783. MS(FAB) 342[M+1]$^+$. 1H-NMR(CDCl$_3$): δ 1.26(3H, d, J=6.3 Hz) 3.21–3.23(1H, m) 3.42–3.64(2H, m) 4.05–4.08 (1H, m) 7.25–7.29(2H, m) 7.40–7.44(2H, m) 7.48(1H, dd, J=4.5 and 8.0 Hz) 8.70(1H, dd, J=1.9 and 4.5 Hz) 8.84(1H, dd, J=1.9 and 8.0 Hz) 8.99 (1H, s) 10.10(1H, brs).

Example 156

Synthesis of 1-(4-fluorophenyl)-N-(4-hydroxybutyl)-1,4-dihydro[1,8]naphthylidin-4-one-3-carboxamide The same reaction was carried out as in Example 53, except for using 4-amino-1-butanol, instead of isopropylamine, to obtain the above-identified compound (189 mg, 95%) as a colorless crystal.

IR(KBr)cm$^{-1}$: 3246, 3058, 1664, 1613, 1546, 1508, 1223. MS(FAB) 356[M+1]$^+$. 1H-NMR(CDCl$_3$): δ 1.67–1.76(4H, m) 3.52–3.57(2H, m) 3.7J=3.75(2H, m) 7.24–7.29(2H, m) 7.39–7.43(2H, m) 7.46(1H, dd, J=4.5 and 8.0 Hz) 8.70(1H, dd, J=1.9 and 4.5 Hz) 8.83(1H, dd, J=1.9 and 8.0 Hz) 8.98(1H, s) 9.81(1H, brs).

Example 157

Synthesis of 1-(4-fluorophenyl)-N-(3-methoxypropyl)-1,4-dihydro[1,8]naphthylidin-4-one-3-carboxamide The same reaction was carried out as in Example 53, except for using 3-methoxypropylamine, instead of isopropylamine, to obtain the above-identified compound (189 mg, 95%) as a colorless crystal.

IR(KBr)cm$^{-1}$: 3384, 1668, 1558, 1506, 1428, 1221, 796. MS(FAB) 356[M+1]$^+$. 1H-NMR(CDCl$_3$): δ 1.91–1.96(2H, m) 3.39(3H, s) 3.52(2H, t, J=6.3 Hz) 3.55–3.61(2H, m) 7.24–7.29(2H, m) 7.39–7.44(2H, m) 7.47(1H, dd, J=4.5 and 7.9 Hz) 8.69(1H, dd, J=1.9 and 4.5 Hz) 8.83(1H, dd, J=1.9 and 7.9 Hz) 8.98(1H, s) 9.83(1H, brs).

Example 158

Synthesis of N-(3-chloropyridin-4-yl)-1-(4-fluorophenyl)-1,4-dihydro[1,8]naphthylidin-4-one-3-carboxamide The same reaction was carried out as in Example 53, except for using 4-amino-3-chloropyridine, instead of isopropylamine, to obtain the above-identified compound (235 mg, 85%) as a colorless crystal.

IR(KBr)cm$^{-1}$: 1684, 1616, 1564, 1506, 1424, 789. MS(FAB) 395[M+1]$^+$. 1H-NMR(CDCl$_3$): δ 7.25–7.33(2H, m) 7.44–7.48(2H, m) 7.53(1H, dd, J=4.5 and 8.0 Hz) 8.43–8.44(1H, m) 8.58–8.59(1H, m) 8.60(1H, s) 8.74(1H, dd, J=1.9 and 4.5 Hz) 8.94(1H, dd, J=1.9 and 8.0 Hz) 9.06(1H, s) 12.64(1H, brs).

Example 159

Synthesis of N-(3-chloropyridin-4-yl)-1-(4-methoxyphenyl)-1,4-dihydro[1,8]naphthylidin-4-one-3-carboxamide The same reaction was carried out as in Example 53, except for using 4-amino-3-chloropyridine, instead of isopropylamine, to obtain the above-identified compound (207 mg, 75%) as a colorless crystal.

IR(KBr)cm$^{-1}$: 2954, 1688, 1576, 1508, 1421, 1241, 787. MS(FAB) 407[M+1]$^+$. 1H-NMR(CDCl$_3$): δ 3.91(3H, s) 7.09–7.11(2H, m) 7.36–7.39(2H, m) 7.52 (1H, dd, J=4.5 and 8.0 Hz) 8.42–8.44(1H, m) 8.58–8.59(1H, m) 8.60(1H, s) 8.76(1H, dd, J=1.9 and 4.5 Hz) 8.94(1H, dd, J=1.9 and 8.0 Hz) 9.08(1H, s) 12.71(1H, brs).

Industrial Applicability

As explained above, the 1-aryl-1,8-naphthylidin-4-one derivatives and the salts and solvates thereof according to the present invention have type IV phosphodiesterase inhibiting action, and therefore, are effective as a pharmaceutical composition for the prevention or treatment of respiratory diseases, diseases relating to abnormalities of the nervous system, diseases relating to mental abnormalities, inflammatory diseases, joint diseases, various cytokine related diseases, etc.

What is claimed is:

1. A 1-aryl-1,8-naphthylidin-4-one compound having the formula (I'):

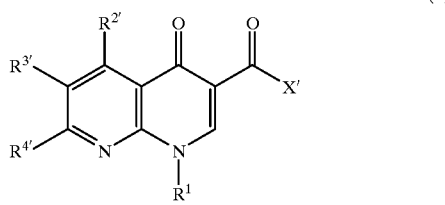

wherein $R^1$ indicates a substituted or unsubstituted aryl group or a substituted or unsubstituted heteroaryl group, $R^{2'}$, $R^{3'}$, and $R^{4'}$ independently are a hydrogen atom, or a substituted or unsubstituted lower alkyl group, X' is the group $NR^5R^6$, $R^5$ and $R^6$ independently are a hydrogen atom, a substituted or unsubstituted lower alkyl group, a substituted or unsubstituted cycloalkyl group, a substituted or unsubstituted aryl group, or a substituted or unsubstituted heteroaryl group, or salt or solvate thereof.

2. A 1-aryl-1,8-naphthylidin-4-one compound or a salt or solvate thereof as claimed in claim 1, wherein all of $R^{2'}$, $R^{3'}$, and $R^{4'}$ in the formula (I') are hydrogen atoms.

3. A 1-aryl-1,8-naphthylidin-4-one compound or a salt or solvate thereof as claimed in claim 1, wherein $R^1$ in the formula (I') is a phenyl group.

4. A 1-aryl-1,8-naphthylidin-4-one compound or a salt or solvate thereof as claimed in claim 1, wherein $R^1$ in the formula (I') is a phenyl group substituted with a lower alkyl group.

5. A 1-aryl-1,8-naphthylidin-4-one compound or a salt or solvate thereof as claimed in claim 1, wherein $R^1$ in the formula (I') is a phenyl group substituted with a lower alkoxy group.

6. A 1-aryl-1,8-naphthylidin-4-one compound or a salt or solvate thereof as claimed in claim 1, wherein $R^1$ in the formula (I') is a phenyl group substituted with a halogen atom.

7. A 1-aryl-1,8-naphthylidin-4-one compound or a salt or solvate thereof as claimed in claim 1, wherein $R^1$ in the formula (I') is a phenyl group substituted with a nitro group.

8. A 1-aryl-1,8-naphthylidin-4-one compound or a salt or solvate thereof as claimed in claim 1, wherein $R^1$ in the formula (I') is a substituted or unsubstituted pyridyl group.

9. A 1-aryl-1,8-naphthylidin-4-one compound or a salt or solvate thereof as claimed in claim 1, wherein $R^1$ in the formula (I') is a substituted or unsubstituted pyrazinyl group.

10. A 1-aryl-1,8-naphthylidin-4-one compound or a salt or solvate thereof as claimed in claim 1, wherein $R^1$ in the formula (I') is a substituted or unsubstituted thiazolyl group.

11. A 1-aryl-1,8-naphthylidin-4-one compound or a salt or solvate thereof as claimed in claim 1, wherein one of $R^5$ or $R^6$ in the formula (I') is a hydrogen atom.

12. A 1-aryl-1,8-naphthylidin-4-one compound or a salt or solvate thereof as claimed in claim 1, wherein one of $R^5$ or $R^6$ in the formula (I') is a substituted or unsubstituted phenyl group and the other is a hydrogen atom.

13. A 1-aryl-1,8-naphthyldin-4-one compound or a salt or solvate thereof as claimed in claim 1, wherein one of $R^5$ or $R^6$ in the formula (I') is a substituted or unsubstituted pyridyl group and the other is a hydrogen atom.

14. A 1-aryl-1,8-naphthylidin-4-one compound or a salt or solvate thereof as claimed in claim 1, wherein one of $R^5$ or $R^6$ in the formula (I') is a 2,6-dichlorophenyl group and the other is a hydrogen atom.

15. A 1-aryl-1,8-naphthylidin-4-one compound or a salt or solvate thereof as claimed in claim 1, wherein one of $R^5$ or $R^6$ in the formula (I') is a 3,5-dichloropyridine-4-yl group and the other is a hydrogen atom.

16. A 1-aryl-1,8-naphthylidin-4-one compound or a salt or solvate thereof, as claimed in claim 1, wherein one of $R^5$ or $R^6$ in the formula (I') is a 4-pyridyl group and the other is a hydrogen atom.

17. A pharmaceutical composition comprising a 1-aryl-1, 8-naphthylidin-4-one compound having the formula (I'):

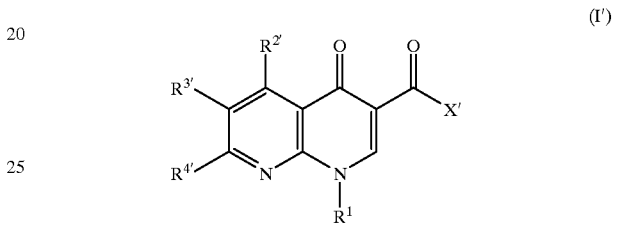

wherein $R^1$ is a substituted or unsubstituted aryl group or a substituted or unsubstituted heteroaryl group, $R^{2'}$, $R^{3'}$, and $R^{4'}$ independently are a hydrogen atom, or a substituted or unsubstituted lower alkyl group, X' is a group $NR^5R^6$, wherein $R^1$ and $R^6$ independently are a hydrogen atom, a substituted or unsubstituted lower alkyl group, a substituted or unsubstituted cycloalkyl group, a substituted or unsubstituted aryl group, or a substituted or unsubstituted heteroaryl group, or a salt or solvate thereof.

18. A pharmaceutical composition comprising a 1-aryl-1, 8-naphthylidin-4-one compound having the formula (I):

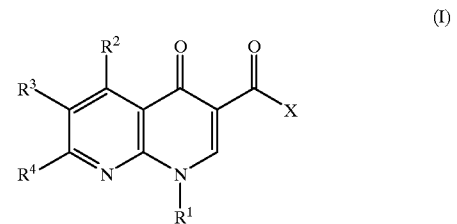

wherein $R^1$ is a substituted or unsubstituted aryl group or a substituted or unsubstituted heteroaryl group, $R^2$, $R^3$, and $R^4$ independently are a hydrogen atom, a substituted or unsubstituted lower alkyl group, X is a group $NR^5R^6$, wherein $R^5$ and $R^6$ independently are a hydrogen atom, a substituted or unsubstituted lower alkyl group, a substituted or unsubstituted cycloalkyl group, a substituted or unsubstituted aryl group, or a substituted or unsubstituted heteroaryl group.

19. A method for inhibiting type IV phosphodiesterase comprising administering, to a patient in need thereof, an effective amount of a 1-aryl-1,8-naphthylidin-4-one compound according to claim 1.

20. A method for inhibiting production of TNF-α comprising administering, to a patient in need thereof, an effective amount of a 1-aryl-1,8-naphthylidin-4-one compound according to claim 1.

21. A method for inhibiting type IV phosphodiesterase comprising administering, to a patient in need thereof, an effective amount of a 1-aryl-1,8-naphthylidine-4-one compound having the formula (I):

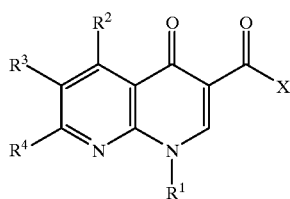

(I)

wherein $R^1$ is a substituted or unsubstituted aryl group or a substituted or unsubstituted heteroaryl group, $R^2$, $R^3$, and $R^4$ independently are a hydrogen atom, a substituted or unsubstituted lower alkyl group, or a halogen atom, X is a group $NR^5R^6$ or a group $OR^7$, wherein $R^5$ and $R^6$ independently are a hydrogen atom, a substituted or unsubstituted lower alkyl group, a substituted or unsubstituted cycloalkyl group, a substituted or unsubstituted aryl group, or a substituted or unsubstituted heteroaryl group, and $R^7$ is a hydrogen atom, a substituted or unsubstituted lower alkyl group, or a substituted or unsubstituted cycloalkyl group or a salt or solvate thereof.

22. A method for inhibiting production of TNF-α comprising administering, to a patient in need thereof, an effective amount of a 1-aryl-1,8-naphthylidine-4-one compound having the formula (I):

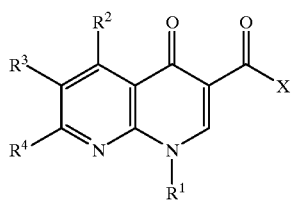

(I)

wherein $R^1$ is a substituted or unsubstituted aryl group or a substituted or unsubstituted heteroaryl group, $R^2$, $R^3$, and $R^4$ independently are a hydrogen atom, a substituted or unsubstituted lower alkyl group, or a halogen atom, X is a group $NR^5$, $R^6$ or a group $OR^7$, wherein $R^5$ and $R^6$ independently are a hydrogen atom, a substituted or unsubstituted lower alkyl group, a substituted or unsubstituted cycloalkyl group, a substituted or unsubstituted aryl group, or a substituted or unsubstituted heteroaryl group, and $R^7$ is a hydrogen atom, a substituted or unsubstituted lower alkyl group, or a substituted or unsubstituted cycloalkyl group or a salt or solvate thereof.

23. A pharmaceutical composition as claimed in claim 18, wherein all of $R^2$, $R^3$, and $R^4$ in the formula (I) are hydrogen atoms.

24. A pharmaceutical composition as claimed in claim 18, wherein $R^1$ in the formula (I) is a phenyl group.

25. A pharmaceutical composition as claimed in claim 18, wherein $R^1$ in the formula (I) is a phenyl group substituted with at least one substituent selected from the group consisting of lower alkyl groups, lower alkoxy groups, halogen atoms and a nitro group.

26. A pharmaceutical composition as claimed in claim 18, wherein $R^1$ in the formula (I) is a substituted or unsubstituted pyridyl group.

27. A pharmaceutical composition as claimed in claim 18, wherein $R^1$ in the formula (I) is a substituted or unsubstituted pyrazinyl group.

28. A pharmaceutical composition as claimed in claim 18, wherein $R^1$ in the formula (I) is a substituted or unsubstituted thiazolyl group.

29. A pharmaceutical composition as claimed in claim 18, wherein one of $R^5$ or $R^6$ in the formula (I) is a hydrogen atom.

30. A pharmaceutical composition as claimed in claim 18, wherein one of $R^5$ or $R^6$ in the formula (I) is a substituted or unsubstituted phenyl group and the other is a hydrogen atom.

31. A pharmaceutical composition as claimed in claim 18, wherein one of $R^5$ or $R^6$ in the formula (I) is a substituted or unsubstituted pyridyl group and the other is a hydrogen group.

32. A pharmaceutical composition as claimed in claim 18, wherein one of $R^5$ or $R^6$ in the formula (I) is a 2,6-dichlorophenyl group and the other is a hydrogen atom.

33. A pharmaceutical composition as claimed in claim 18, wherein one of RI or $R^6$ in the formula (I) is a 3,5-dichloropyridin-4-yl group and the other is a hydrogen atom.

34. A pharmaceutical composition as claimed in claim 18, wherein one of $R^5$ or $R^6$ in the formula (I) is a 4-pyridyl group and the other is a hydrogen atom.

* * * * *